(12) United States Patent
Datta

(10) Patent No.: US 9,511,219 B1
(45) Date of Patent: *Dec. 6, 2016

(54) DUAL VACUUM DEVICE FOR MEDICAL FIXTURE PLACEMENT INCLUDING FOR THORACOSCOPIC LEFT VENTRICULAR LEAD PLACEMENT

(71) Applicant: Subhajit Datta, Delaware, OH (US)

(72) Inventor: Subhajit Datta, Delaware, OH (US)

( * ) Notice: Subject to any disclaimer, the term of this patent is extended or adjusted under 35 U.S.C. 154(b) by 317 days.

This patent is subject to a terminal disclaimer.

(21) Appl. No.: 14/223,562

(22) Filed: Mar. 24, 2014

(51) Int. Cl.
  *A61B 1/05* (2006.01)
  *A61N 1/05* (2006.01)
  *A61B 18/14* (2006.01)
  *A61B 18/00* (2006.01)

(52) U.S. Cl.
  CPC .............. *A61N 1/059* (2013.01); *A61B 18/14* (2013.01); *A61B 2018/00595* (2013.01); *A61B 2018/1412* (2013.01)

(58) Field of Classification Search
  CPC .... A61N 1/0587; A61N 1/0592; A61N 1/059; A61N 1/057
  See application file for complete search history.

(56) References Cited

U.S. PATENT DOCUMENTS

| | | | |
|---|---|---|---|
| 4,146,037 A | 3/1979 | Flynn et al. | |
| 4,271,846 A | 6/1981 | Little | |
| 4,972,847 A | 11/1990 | Dutcher et al. | |
| 5,139,033 A | 8/1992 | Everett et al. | |
| 5,203,772 A | 4/1993 | Hammerslag et al. | |
| 5,342,413 A | 8/1994 | Hirschberg et al. | |
| 5,582,580 A * | 12/1996 | Buckman, Jr. ...... | A61M 1/1068 601/107 |
| 5,882,333 A | 3/1999 | Schaer et al. | |
| 5,902,331 A | 5/1999 | Bonner et al. | |
| 5,972,013 A | 10/1999 | Schmidt | |
| 6,132,456 A | 10/2000 | Sommer et al. | |
| 6,193,652 B1 * | 2/2001 | Berky .................... | A61B 17/02 600/201 |
| 6,697,677 B2 | 2/2004 | Dahl et al. | |
| 6,868,291 B1 | 3/2005 | Bonner et al. | |
| 6,875,171 B2 * | 4/2005 | Paolitto .................. | A61B 17/02 600/205 |

(Continued)

FOREIGN PATENT DOCUMENTS

| | | |
|---|---|---|
| WO | WO 99/06104 | 2/1999 |
| WO | WO 2004/058326 | 7/2004 |
| WO | WO 2008/058265 | 5/2008 |

*Primary Examiner* — Jocelyn D Ram
(74) *Attorney, Agent, or Firm* — Roger A. Gilcrest

(57) ABSTRACT

The present invention includes devices and methods for lead, conduit or other medical fixture placement in tissues or organs. The device is configured to permit the placement foot, such as a suction foot, to articulate to a desired position with respect to the target tissue, while the lead, conduit or other medical fixture is releasably attached to the placement foot to permit it to be released from the placement foot after stabilization on the target tissue site. In a preferred embodiment, the invention features an articulating dual suction foot device, an inner lead conduit or guide and foot contained within an outer lead conduit or guide and foot, with the inner conduit or guide configured to extend from the outer conduit or guide, and to be further articulated once extended.

26 Claims, 42 Drawing Sheets

(56) References Cited

U.S. PATENT DOCUMENTS

| | | | |
|---|---|---|---|
| 7,270,669 B1 * | 9/2007 | Sra | A61N 1/0587 600/375 |
| 7,479,104 B2 * | 1/2009 | Lau | A61B 17/0206 600/37 |
| 7,526,342 B2 * | 4/2009 | Chin | A61B 17/00008 607/119 |
| 7,544,197 B2 | 6/2009 | Kelsch et al. | |
| 7,890,192 B1 | 2/2011 | Kelsch et al. | |
| 7,930,040 B1 | 4/2011 | Kelsch et al. | |
| 2003/0187461 A1 * | 10/2003 | Chin | A61B 17/00008 606/129 |
| 2003/0212446 A1 * | 11/2003 | Kaplan | A61N 1/0587 607/129 |
| 2004/0088035 A1 * | 5/2004 | W. Guenst | A61N 1/0587 607/131 |
| 2004/0153098 A1 | 8/2004 | Chin et al. | |
| 2004/0215139 A1 | 10/2004 | Cohen | |
| 2005/0004644 A1 | 1/2005 | Kelsch et al. | |
| 2005/0288666 A1 * | 12/2005 | Bertolero | A61B 1/12 606/41 |
| 2006/0009827 A1 * | 1/2006 | Kurth | A61N 1/0573 607/119 |
| 2006/0015165 A1 * | 1/2006 | Bertolero | A61B 1/12 607/119 |
| 2006/0161238 A1 | 7/2006 | Hall | |
| 2007/0123748 A1 * | 5/2007 | Meglan | A61B 1/00149 600/104 |
| 2007/0255375 A1 * | 11/2007 | Michels | A61N 1/0587 607/119 |
| 2009/0182347 A1 | 7/2009 | Ransbury et al. | |
| 2009/0198251 A1 | 8/2009 | Ransbury et al. | |
| 2010/0069849 A1 * | 3/2010 | Kassab | A61B 17/00491 604/176 |
| 2010/0312256 A1 | 12/2010 | Kassab et al. | |
| 2011/0071524 A1 * | 3/2011 | Keller | A61F 9/00736 606/45 |
| 2013/0296879 A1 * | 11/2013 | Lazeroms | A61B 17/3468 606/129 |

* cited by examiner

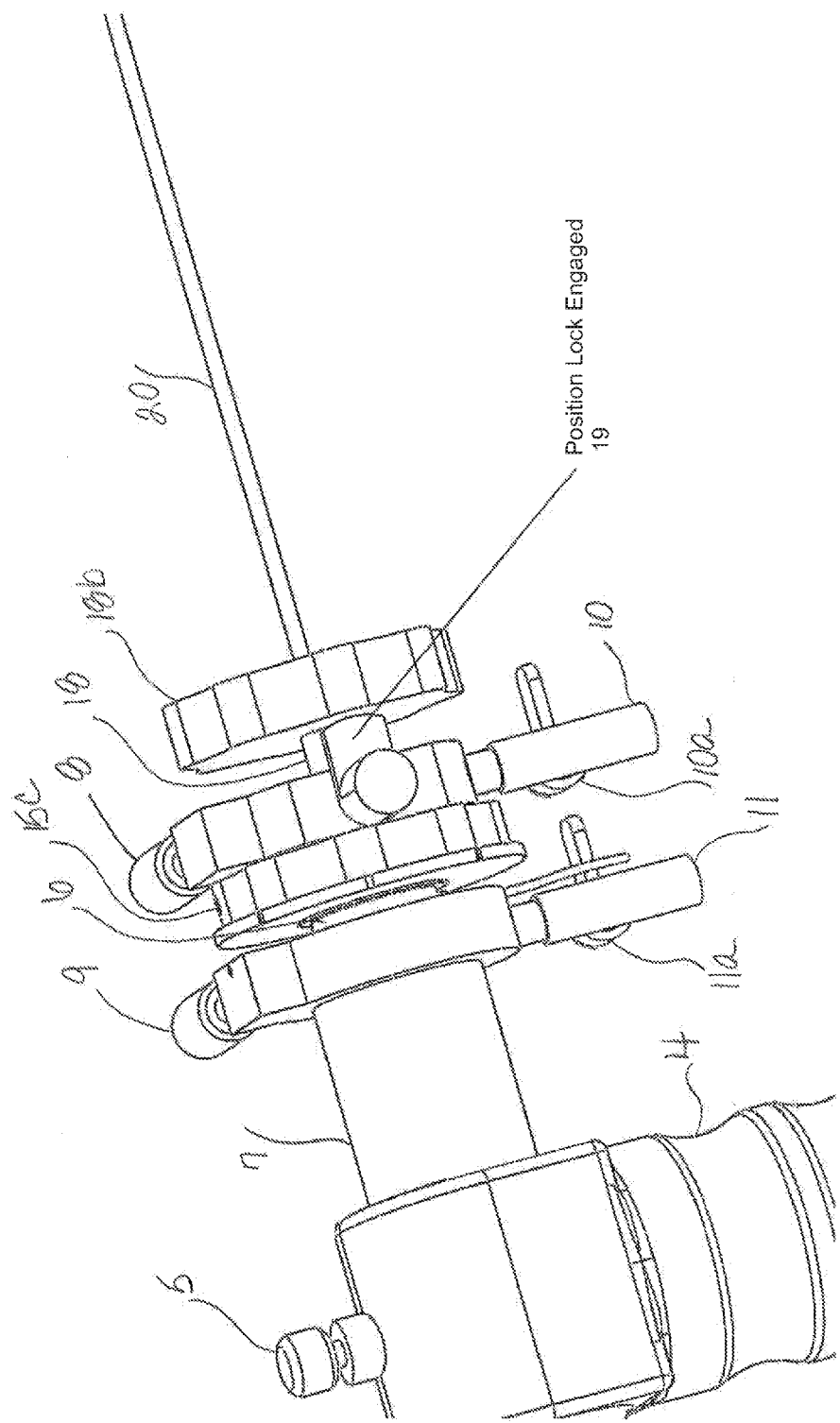

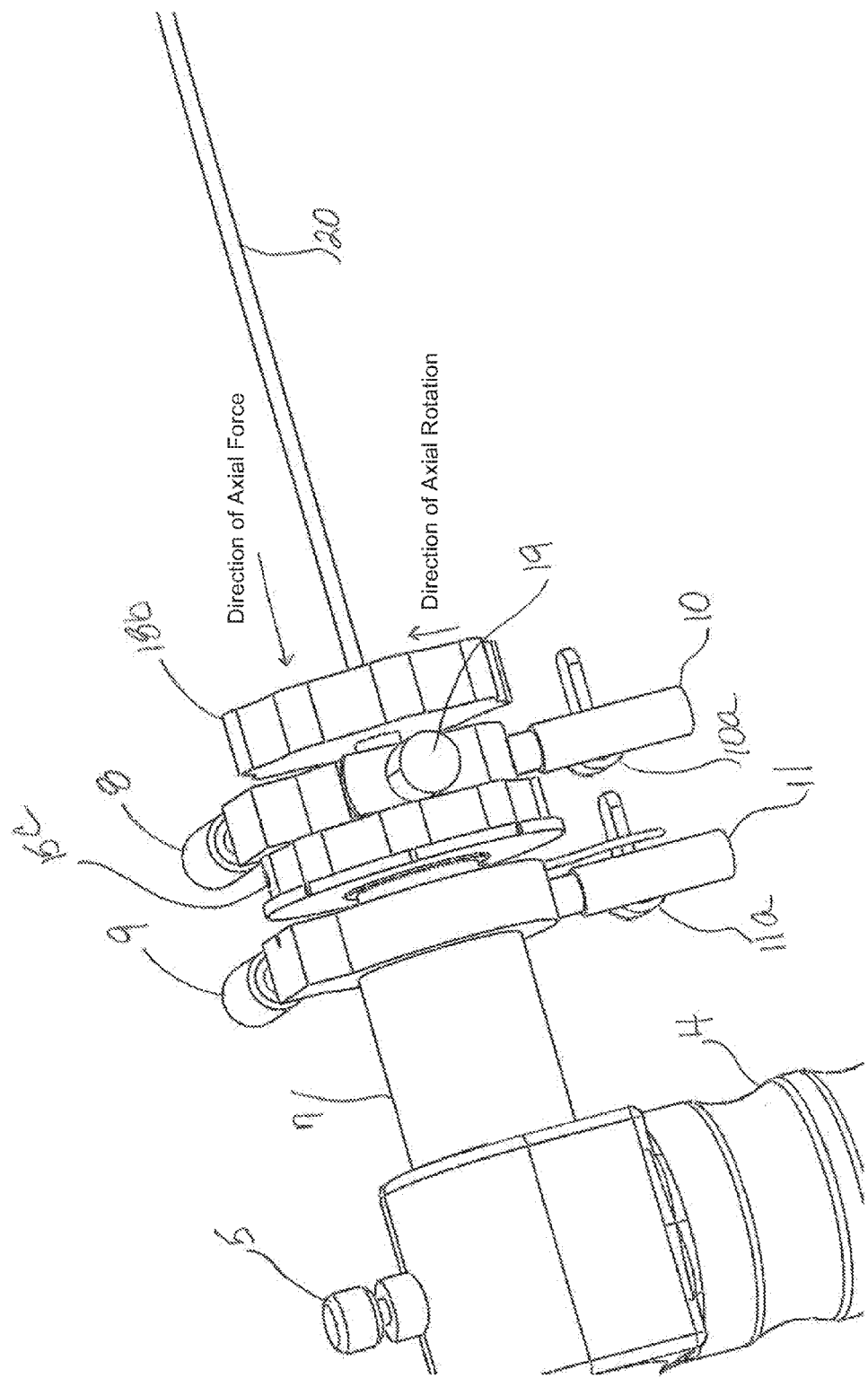

DUAL VACUUM DEVICE FOR MEDICAL FIXTURE PLACEMENT INCLUDING FOR THORACOSCOPIC LEFT VENTRICULAR LEAD PLACEMENT

RELATED APPLICATION DATA

None.

FIELD OF THE INVENTION

The present invention relates to devices and techniques used in thoracoscopic lead placement, and in similar surgical techniques.

BACKGROUND OF THE INVENTION

According to a CDC statistical brief, nearly 5.8 million people in the United States have congestive heart failure. See Lloyd-Jones D, et al. Heart Disease and Stroke Statistics-2010 Update. A Report from The American Heart Association Statistics Committee And Stroke Statistics Subcommittee. Circulation. 2010; 121:E1-E170. About 670,000 people are diagnosed with it each year. Heart failure was a contributing cause of 282,754 deaths in 2006. In 2010, heart failure cost the United States an estimated $39.2 billion. This total includes the cost of health care services, medications, and lost productivity.

Heart failure is a condition in which the heart's pumping power is weaker than normal. With heart failure, blood moves through the heart and body at a slower rate, and pressure in the heart increases. A delay between the contraction of the right and left ventricles often occurs with heart failure, so the walls of the left ventricle are unable to contract synchronously.

Approximately 25-50% of heart failure patients have ventricles that contract asynchronously, and are therefore candidates for biventricular pacing (between 1.5 and 3 million potential patients).

Biventricular pacing, also known as cardiac resynchronization therapy (CRT) utilizes a type of pacemaker that can pace both the septal and lateral walls of the left ventricle.[1] By pacing both the right and left ventricles, the pacemaker can resynchronize a heart.

[1] Pavia S V, Wilkoff B L. Biventricular pacing for heart failure. Cardiol Clin. 2001 November; 19(4):637-51.

Candidates for CRT include patients with severe or moderately severe heart failure symptoms, delayed electrical activation of the heart (such as intraventricular conduction delay or bundle branch block), or those with a history of cardiac arrest or risk factors for cardiac arrest.

CRT improves symptoms of heart failure in about one third of patients who have been treated maximally with medications but still have severe or moderately severe heart failure symptoms. Another third of patients see an improvement in ejection fraction without any major change in symptoms and the last third of the patient population are not responsive to CRT. CRT improves survival, quality of life, heart function, the ability to exercise, and helps decrease hospitalizations in select patients with severe or moderately severe heart failure. CRT can help improve ejection fraction (volume of blood pumped out of the left ventricle) and when combined with an implantable cardiac defibrillator, it can help protect against dangerous, fast heart rhythms.[2] Both CRT pacemakers and CRT defibrillators use a left ventricular pacing lead.

[2] Bristow M, et al. Cardiac-resynchronization therapy with or without an implantable defibrillator in advanced chronic heart failure. 2004. N Engl J Med 350 (21): 2140-50.

The CRT device and its leads can be implanted using an endocardial (transvenous) or epicardial (surgical) approach. The endocardial approach is the most common method. A local anesthetic is given to numb the area. The leads are inserted through an incision in the chest and into a vein. Two leads are guided to the right atrium and right ventricle of the heart, while the third lead is guided through the coronary sinus (the venous system of the heart) to the left ventricle. The lead tips are attached to the heart muscle, while the other ends of the leads are attached to the pacemaker placed in a pocket created under the skin in the upper chest. When the endocardial approach is used, the hospital recovery time is generally 24 hours. The endocardial technique is technically challenging. In some cases, this technique may not be successful due to the size, shape or location of the vein(s). If the endocardial approach cannot be used or is unsuccessful, the epicardial approach is then attempted.

The epicardial approach is a less common method in adults, but more common in children. The leads are placed under general anesthesia. The locations of lead placement are identical to the endocardial approach. The pulse generator is placed in a pocket created under the skin in the abdomen or chest. Although recovery with the epicardial approach is longer than that of the transvenous approach (generally about 3 to 5 days), minimally invasive techniques have enabled shorter hospital stays and recovery times.

There are several complications and costs associated with conventional pacing that may occur during biventricular pacing, including: (a) localized/skin infection, (b) systemic infection secondary to infected pacing box or lead, (c) bleeding, (d) hematoma, (e) lead displacement, (f) equipment failure, i.e. fractured pacing wire, faulty pacing box and (g) pneumothorax.

Standard predictors of operative complications apply, those being degree of heart failure, the surgical environment, diabetes and the duration of the procedure. Although with experience the procedure times reduce, even in the best hands implantation of the left ventricular lead may be time consuming, contributing to an increased infection risk.[3]

[3] Alonso, C, et al. Six year experience of transvenous left ventricular lead implantation for permanent biventricular pacing in patients with advanced heart failure: technical aspects. Heart. 2001:86(4):405-410.

In the initial studies of biventricular pacing, the right atrial and right ventricular leads were inserted via the standard transvenous approach, but the epicardial left ventricular lead was placed surgically via thoracotomy or thoracoscopically. These approaches required a larger incision and general anaesthetic, consequently carrying a significant morbidity and mortality.

In 1998, the preferred method of left ventricular lead insertion using the transvenous approach was introduced.[4] The precise location of the lead is ideally the mid left ventricular cavity in a lateral or posterolateral vein.[5] The use of guiding catheters within the coronary sinus and the use of purpose-designed leads have increased success rates and ability to reach the target vessel. Some of these procedures may require the use of multiple types of catheters and guidewires, adding cost to this procedure. The requirement to position a lead in a branch of the coronary sinus and the techniques required to achieve this account for the additional complications and significant failure rate seen with biventricular pacing. A suitable vein may not be present in the lateral or posterolateral position, prompting placement of left ventricular lead in another ineffective suboptimal location. Thoracoscopic placement of left ventricular lead is not dependent on cardiac venous anatomy. Trans-cardiac-venous placement of left ventricular lead occasionally will cause disturbing phrenic nerve stimulation, causing uncomfortable diaphragmatic twitching and necessitate relocation to suboptimal sites. Thoracoscopic placement visualizes the phrenic nerve and thus placement away from the nerve can be accomplished at the outset.

[4] Daubert, J C, et al. Permanent left ventricular pacing with transvenous leads inserted into the coronary veins. Pacing clin. Electrophysiol. 1998; 21(1 pt 2):239-245.
[5] Auricchio, A, et al. The pacing therapies for congestive heart failure (path-chf) study: rationale, design, and endpoints of a prospective randomized multicenter study. Am. J. Cardiol. 1999; 83(5b):130d-135d.

Although devices of various types have been developed for the endocardial approach, there remains a need for a device that is relatively simple to construct and use that permits firm and accurate lead or conduit placement in tissue, including cardiac tissue. There also are applications relating to a variety of operations and procedures involving the placement of a variety of leads or conduits in a variety of tissues that likewise would benefit from the device and methods of the present invention.

SUMMARY OF THE INVENTION

The present invention is an additional embodiment of the devices and methods described in Application Ser. No. 61/774,406, filed Mar. 7, 2013, and application Ser. No. 14/186,532, filed Feb. 21, 2014, which are hereby incorporated herein by reference, and whose features may be incorporated independently into the present invention.

The present invention includes devices and methods directed to the placement of foreign objects into organs and other body parts, especially where the body parts are in motion, and are described in the context of the placement of a cardiac lead (i.e., the object) into the heart (i.e., as an example of an organ and other body part). The invention may be used for lead on other fixture placement in humans or non-humans, and may also include a kit comprising the individual, separable parts of the device of the invention. The devices and methods are particularly adapted for such operations where there is a requirement or some benefit in the articulation of the instrument to facilitate better approach to the target site, as well as where there is a requirement or some benefit to the excision of tissue in advance of the object placement and attachment to a moving organ or tissue before precise placement of a lead or probe. The present invention may be summarized as follows:

The present invention generally includes a lead or conduit placement device that is configured to permit the placement foot, such as a suction foot, to articulate to a desired position with respect to the target tissue, while the lead is releasably attached to the placement foot to permit it to be released from the placement foot after fixing the lead or conduit in the tissue.

Another aspect of the present invention is to arrange and configure the inner suction foot portion with the lead (or lead-placing head portion) releasably attached to the inner suction foot portion while allowing the articulating movement of the inner suction foot portion, while being releasable through hand force to permit the lead to be separated from the inner suction foot portion after fixing the lead or conduit in the tissue.

The lead placement device of the present invention features dual suction feet provided with a vacuum through cooperating lead conduits or guides extending through the device. The device also preferably includes actuators that transmit movement to the inner and outer lead conduits or guides, so as to bring about articulation of the dual suction feet. There are several optional and preferred arrangements of the present invention that are described in its many embodiments.

In general terms, the device of the present invention is adapted for the thoracoscopic placement of a lead or other medical fixture at a target site on an epicardial surface of a heart, and comprises: (a) an inner tubular lead conduit or guide having an inner lead conduit or guide distal end comprising an inner suction foot portion, the inner tubular lead conduit or guide having a flexible distal end and adapted to conduct a vacuum to the inner suction foot portion; (b) a lead drive having a flexible distal end and inserted within the inner tubular lead conduit or guide so as to extend to the inner tubular lead conduit or guide distal end; (c) a lead extending through the lead drive and having a lead distal end portion, the lead distal end portion extending from the distal end of the lead drive for contact with the epicardial surface of the heart; (d) an outer tubular lead conduit or guide having an outer lead conduit or guide distal end comprising an outer suction foot portion, the outer tubular lead conduit or guide having a flexible distal end and adapted to conduct a vacuum to the outer suction foot portion while being adapted to slidingly conduct the inner tubular lead conduit, so as to permit the inner tubular lead conduit or guide to be extended from the outer lead conduit or guide distal end; (e) an elongated sheath body having a longitudinal axis, a proximal end portion and a distal end portion, and having a proximal inlet and a distal lead outlet for extending the inner and outer lead conduits or guides therethrough, the elongated sheath body comprising a lead receiving passageway for receiving and conducting the inner and outer lead conduits or guides between the proximal inlet and the distal lead outlet; the lead drive adapted to releasably engage the lead distal end portion such that the lead drive may be released from the lead distal end portion once the lead is attached to the epicardial surface of a heart (the sheath preferably provided with a set screw to hold the outer tubular lead conduit or guide with its contents in a set position); (f) a first actuator adapted to articulate the inner suction foot portion and the outer suction foot portion while the inner suction foot portion is disposed within the outer suction foot portion; and (g) a second actuator adapted to articulate the inner suction foot portion when the inner suction foot portion is extended from the outer suction foot portion. As may be appreciated from consideration of the construction of the preferred embodiment, the actuators may be any arrangement adapted to exert an articulating force through or around the inner and outer tubular lead conduit or guide to being about articulation of the inner and outer suction feet.

The arrangement of the present invention permits the separate functionality of the inner and outer tubular lead conduits or guides, including independent articulation of the two tubular lead conduits or guides, such as in two separate planes at right angles to each other.

The inner and outer tubular lead conduits or guides may be made flexible on their distal ends for instance through the use of a relatively thin portion of its tubular structure at the distal end as compared to the balance of its structure, through the use of a flexible material with tension cords incorporated into the balance of the tubular structure, and/or through the use of laminate or corrugated structures or flat spiral coils permitting the distal end to flex and thereby articulate. The inner and outer tubular lead conduits or guides may be of any material appropriate for medical use, such as disposable plastics or sterilizable metals. The inner and outer tubular lead conduits or guides may be or any configuration or cross-section not inconsistent with the described function, such as those of circular, ovoid, polygonal or even arcuate cross-section; and they may be made with telescoping portions where desirable. Accordingly, as used herein the term "conduit or guide" should be understood as including the structures in the device with articulating distal ends and that serve to provide a course through which the lead may be extended to the desired attachment site while conducting vacuum suction therethrough.

The elongated body may be of any length, but typically will have a lead receiving passageway that has a length in the range of 10 cm to 40 cm for manual devices, and preferably about 15 cm in length.

It is preferred that the elongated body sheath be provided with a handle portion extending laterally therefrom for ease of manual use, though it will be appreciated that the invention may be adapted for robotic use. The handle portion, such as a handle extending laterally from the elongated body, allows the operator to advance the device into the surgical site, and further articulate the inner and outer tubular vacuum guides allowing ultimately for the lead drive to insert the cardiac lead through operation of the lead placement device, as described herein.

The device in its preferred embodiment will comprise a hand-driven actuator, such as a knob, to permit the outer lead conduit or guide to be extended from the elongated body by hand, and to be articulated once extended therefrom while containing the inner lead conduit.

The device preferably includes a first actuator, such as preferably comprising a knob adapted to articulate the inner suction foot portion and the outer suction foot portion while the inner suction foot portion is disposed within the outer suction foot portion, as well as a second actuator, such as preferably comprising a knob adapted to articulate the inner suction foot portion when the inner suction foot portion is extended beyond the outer suction foot portion. The device thus also will preferably include a hand-driven actuator, such as a knob or other manually operable arrangement, to permit the inner lead conduit or guide to be articulated once extended from the elongated body by hand, to articulate the lead drive it guides through articulation of its inner suction foot. This may be done by providing the inner suction foot portion with an engagement aperture, and wherein the lead head portion is adapted to releasably engage the engagement aperture, and extend therefrom once the lead is placed.

It is preferred that the lead distal end is held by the lead drive so as to extend from the distal end of the lead drive, such as with a lead drive fixture at the distal end thereof. The lead drive preferably will have a flexible distal end portion to be able to follow the articulation of the inner and outer tubular lead conduits or guides during operation as described herein. The lead drive may be made flexible on its end for instance through the use of a flexible coil or through the use of a flexible material incorporated into the balance of the tubular structure.

The device in its preferred embodiment also includes an electrocautery blade extending from between the inner and outer suction foot portions. It is also preferred that the inner and/or outer suction foot portion(s) comprise(s) a plurality of cups connected to air channels, so as to be capable of providing suction to the suction foot portion(s), and it is preferred that the inner suction foot portion comprises a plurality of cups connected to air channels, so as to be capable of providing suction to the inner suction foot portion to stabilize the device prior to lead testing and/or insertion.

As to the lead distal end, it is preferred that the lead drive presents the lead distal end such that it extends from the distal side of the lead drive (typically for about 1-2 mm in the preferred embodiment), i.e., and also from the distal side of the inner suction foot portion holding the lead drive head in place.

The device of the present invention thus provides actuators such as in the form of knob portions disposed on the proximal end portion, the knobs adapted to move respective actuators within the elongated body so as to articulate the outer and inner suction foot portions, including articulating the inner suction foot portion once extended from within the distal portion of the outer tubular lead conduit. The actuators may be in the form of tension cords attached to respective knob portions disposed on the proximal end portion, the knobs adapted to move the tension cords within inner and outer lead conduits or guides held by the elongated body so as to articulate the respective inner and outer suction foot portions. In a preferred embodiment, the inner and outer lead conduits or guides each comprise a "flat coil" or equivalent mechanical arrangement permitting the rotation action of the knob (or other hand movement) to be translated into an articulating movement of the distal portion of the inner and outer lead conduits or guides such as by hand force transmitted from the knobs as described herein.

The device of the present invention additionally comprises a source of vacuum suction in fluid communication with the inner and outer lead conduit or guide suction foot portions, the source of vacuum suction selected from the group consisting of a hand pump, or a syringe attached to the elongated body, or a motorized pump supplying vacuum suction to the respective inner and outer lead conduit suction foot portions which in turn may be connected to the proximal, operator end of inner tubular lead conduit or guide, and regulated by any appropriate fluid control device or valve, including stop-cocks.

In its preferred embodiment, the device of the present invention additionally comprises a removable spacer adapted to maintain the position of the inner suction foot portion with respect to the outer suction foot portion in which case the inner lead conduit or guide is longer that the outer lead conduit, such as described in the Figures.

Also preferred is that the distal end portion of the elongated sheath body additionally comprises a moveable cover, such as a closure lid adapted to reversibly open and close the distal lead outlet.

The invention may also be understood as being a device adapted for the thoracoscopic placement of a lead on an epicardial surface of a heart (or other medical fixture at a target site on an organ or other body part), and comprises: (a) an inner tubular lead conduit having an inner lead conduit distal end comprising an inner suction foot portion, the inner tubular lead conduit being flexible (variable distal end flexible and rest proximal portion rigid) and adapted to conduct a vacuum to the inner suction foot portion; (b) a lead with lead drive insertable through the inner tubular lead conduit proximal end; (c) a lead extending through the lead head portion and having a lead distal end portion, the lead distal end portion extending from the distal end of the inner tubular lead conduit or guide for contact with the epicardial surface of the heart; (d) an outer tubular lead conduit or guide having an outer lead conduit or guide distal end comprising an outer suction foot portion, the outer tubular lead conduit or guide being flexible (preferably the variable distal end being relatively flexible, and balance of the lead conduit; i.e., the proximal portion, being relatively rigid), and adapted to conduct a vacuum to the outer suction foot portion while being adapted to slidingly conduct the inner tubular lead conduit, so as to permit the inner tubular lead conduit or guide to be extended from the outer lead conduit or guide distal end (allowing the longitudinal movement of the former with respect to the latter, and the independent articulation of the two tubular lead conduits or guides both when co-terminal within one another, and when the inner tubular lead conduit or guide is extended from the outer tubular lead conduit); (e) an elongated sheath body having a longitudinal axis, a proximal end portion and a distal end portion, and having a proximal inlet and a distal lead outlet for extending the inner and outer lead conduits or guides therethrough, the elongated sheath body comprising a lead receiving passageway for receiving and conducting the inner and outer lead conduits or guides between the proximal inlet and the distal lead outlet; the lead head portion adapted to releasably engage the inner suction foot portion such that such engagement is of sufficient strength to maintain the position of the lead distal end portion as it engages the epicardial surface of a heart, and sufficiently releasable such that the lead head portion may be released from the inner suction foot portion once the lead is attached (i.e., preferably screwed into the heart muscle) to the epicardial surface of a heart; and (f) a first actuator extending from the proximal end portion to the distal end portion and adapted to articulate the outer suction foot portion; and (g) a second actuator extending from the proximal end portion to the distal end portion and adapted to articulate the inner suction foot portion.

The present invention also includes a method of cardiac lead placement with articulating suction foot and releasable cardiac lead. The present invention in general terms comprises a method for the thoracoscopic placement of a lead at a target site on an epicardial surface beyond pericardium tissue of a heart of a human or animal, the method comprising: (a) extending into the pericardial region a device comprising: (1) an inner tubular lead conduit or guide having an inner lead conduit or guide distal end comprising an inner suction foot portion, the inner tubular lead conduit or guide being flexible and adapted to conduct a vacuum to the inner suction foot portion; (2) a lead head portion connected to the inner tubular lead guide distal end; (3) a lead extending through the lead head portion and having a lead distal end portion, the lead distal end portion extending from the inner tubular lead conduit or guide distal end for contact with the epicardial surface of the heart; (4) an outer tubular lead conduit or guide having an outer lead conduit or guide distal end comprising an outer suction foot portion, the outer tubular lead conduit or guide being flexible and adapted to conduct a vacuum to the outer suction foot portion while being adapted to slidingly conduct the inner tubular lead conduit, so as to permit the inner tubular lead conduit or guide to be extended from the outer lead conduit or guide distal end; (5) an elongated sheath body having a longitudinal axis, a proximal end portion and a distal end portion, and having a proximal inlet and a distal lead outlet for extending the inner and outer lead conduits or guides therethrough, the elongated sheath body comprising a lead receiving passageway for receiving and conducting the inner and outer lead conduits or guides between the proximal inlet and the distal lead outlet, the lead head portion adapted to releasably engage the inner suction foot portion such that such engagement is of sufficient strength to maintain the position of the lead distal end portion as it engages the epicardial surface of a heart, and sufficiently releasable such that the lead head portion may be released from the inner suction foot portion once the lead is attached to the epicardial surface of a heart; and (6) a first actuator extending from the proximal end portion to the distal end portion and adapted to articulate the outer suction foot portion; and (7) a second actuator extending from the proximal end portion to the distal end portion and adapted to articulate the inner suction foot portion; (8) an electrocautery blade extendable from between the outer and the inner tubular lead conduits or guides; and (b) positioning the inner and outer suction foot portions upon the pericardium tissue, the inner and outer suction foot portions being maintained substantially co-planar to one another; (c) applying suction through the inner and outer tubular lead conduits or guides so as to stabilize the inner and outer suction foot portions against the pericardium tissue; (d) cutting a portion of the pericardium tissue while securing the portion of the pericardium tissue to the inner suction foot portion; (e) withdrawing the inner tubular lead conduit or guide from the outer tubular lead conduit or guide so as to remove the portion of the pericardium tissue from the pericardial region; (f) after loading the lead with lead drive into the inner tubular lead conduit, (extending the inner suction foot portion beyond the plane of the outer suction foot portion); (g) inserting the lead distal end portion into the epicardial surface; (h) disengaging the lead head portion from the inner suction foot portion; and (i) releasing the lead from the lead drive; and (j) withdrawing the device from the pericardial region, whereby to leave the lead attached to the epicardial surface.

Also in the most preferred embodiment described herein, the inner and outer suction foot portions may be of any shape, such as presenting a round, polygonal, star or ovoid foot print, though it is preferred that it have a round or other radially symmetric footprint shape, and may comprise a plurality of air channels in fluid contact with the respective inner and outer tubular lead conduits or guides, so as to be capable of providing suction to the respective suction foot portions.

It will be appreciated that the lead itself may be incorporated into supplementary structure for ancillary purposes such as electrical insulation and to be able to mechanically cooperate with the balance of the device and consistent with its function as described herein (such as by providing sleeves and flanges, etc.) One such arrangement involves having the lead distal end being held by a lead head portion (typically of a polymeric material) so as to extend from the distal side of the lead head portion.

The device may also additionally comprise an interferant release collar attached to the inner tubular lead guide distal end portion and disposed on the distal side of the inner guide suction foot portion, the interferant release collar being larger than the aperture. This allows more precise and oriented lead placement through advancement of the lead head portion distally from the inner tubular lead guide, while preventing accidental or premature retraction of the lead head portion, as described herein.

The actuator of the preferred embodiment of the present invention may comprise a flexible member connecting the suction foot portion to the elongated body. This flexible member may be any part of sufficient flexibility and resilience to permit the suction foot to articulate as described herein. For instance the flexible member may be in the form of a metal or plastic spring or coil, or equivalent metal or plastic structure.

In the preferred embodiment the actuators are in turn attached to respective knobs disposed on the proximal end portion thereof, the knobs adapted to move the actuators within the inner and outer tubular lead guides (once extended from the elongated body), so as to articulate the inner and outer suction feet at their respective ends in unison (prior to the extension of the inner tubular lead guide from within the outer tubular lead guide), as well as to articulate the inner tubular lead guide independently (and thereby the inner suction foot, to provide an articulated path along which the distal end of the lead drive advances as described herein), once extended from the outer tubular lead guide.

The actuator(s) may be any part of sufficient flexibility and resilience to facilitate the movement of the suction feet to articulate as described herein. For instance, it is preferred that each actuator comprise one or more tension cords attached to a knob portion disposed on the proximal end portion, the knob adapted to move the inner and outer lead guides within the elongated body so as to articulate the suction foot.

With respect to the lead guides and vacuum source for use in the invention in its many embodiments, the device may additionally comprise a source of vacuum suction in fluid communication with the lead guides. The source of vacuum suction in fluid communication with the lead guides may be any source sufficient for operation of the device, and typically may be selected from the group consisting of a hand pump, or a syringe attached to the elongated body, or a motorized pump supplying vacuum suction to the lead guides. The device of the present invention may optionally include a plurality of tubular structures extending through the lead guides and extending between the proximal inlet and the distal outlet. In the preferred embodiment, in both the inner and outer lead conduits or guides, the vacuum or negative pressure traverses through the shell of the relatively rigid, proximal portion of the tubes, and then through a relatively flexible tube to the suction foot in the articulating distal portion of the tubes, as shown in the diagrams.

The device of the present invention may also include a supplementary test lead extending from any effective portion of the device, such as from the lead head portion and through the elongated body.

Another aspect of the present invention is a lead placement device with an articulating suction foot as represented, for instance, by the preferred embodiments described herein. It will be appreciated that this aspect of the invention may be constructed and used in other devices beyond that described in the preferred embodiment herein.

This aspect of the present invention may be described as a device adapted for the thoracoscopic placement of a lead at a target site on an epicardial surface of a heart (though it may also be used with other tissues and other purposes, such as biopsy, stent or tubule placement, etc. by substituting the cardiac lead with an alternative with the desired biopsy needle, stent or tubule placement arrangement, as desired). The device comprises in general terms, (a) dual hollow lead guides, one inside the other, i.e., the inner lead guide contained to be extended from within the outer lead guide, each having a lead distal end portion and a respective suction foot in fluid communication with the respective hollow lead guide; (b) a lead with the lead drive extending through the inner hollow lead guide, the lead having a lead distal end portion; (c) an elongated body having a longitudinal axis, a proximal end portion and a distal end portion, and having a proximal inlet and a distal lead outlet; the inner lead guide comprises a lead receiving passageway for receiving and conducting the lead distal end to the inner lead guide distal lead outlet; (d) an inner lead guide suction foot portion releasably attached to the lead distal end portion, and being in fluid communication with the inner lead guide, the inner lead guide suction foot portion articulatably attached to the inner lead guide distal end portion such that the suction foot may be articulated with respect to the longitudinal axis (the lead adapted to releasably engage the suction foot portion such that such engagement is of sufficient strength to maintain the position of the lead distal end portion as it engages the epicardial surface of a heart, and sufficiently releasable such that the lead may be released from the suction foot portion once the lead is attached to the epicardial surface of a heart); and (e) an actuator extending from the proximal end portion to the distal end portion and adapted to articulate the suction foot portion with respect to the longitudinal axis both while contained within the outer lead guide and once extended therefrom.

Still another aspect of the present invention is a lead placement device with suction foot and releasable lead head and lead, wherein the device may be adapted for use with any tissue type and for the placement of any conduit type (such as conduit of electrical current or signals, or gas or liquid fluids conduits) for any medical or veterinary purpose.

Other features and embodiments of the device of the present invention may include a device adapted for the thoracoscopic placement of a lead at a target site on an epicardial surface of a heart, the device comprising: (a) an inner tubular lead guide having an inner lead guide distal end comprising an inner suction foot portion, the inner tubular lead guide having a flexible distal end and adapted to conduct a vacuum to the inner suction foot portion; (b) an outer tubular lead guide having an outer lead guide distal end comprising an outer suction foot portion, the outer tubular lead guide having a flexible distal end and adapted to conduct a vacuum to the outer suction foot portion while being adapted to slidingly conduct the inner tubular lead guide, so as to permit the inner tubular lead guide to be extended from the outer lead guide distal end; (c) a locking mechanism adapted to restrict the axial movement of the inner tubular lead guide with respect to the outer tubular lead guide; (d) an elongated sheath body having a longitudinal axis, a proximal end portion and a distal end portion, and having a proximal inlet and a distal lead outlet for extending the inner and outer lead guides therethrough, the elongated sheath body comprising a lead receiving passageway for receiving and conducting the inner and outer lead guides between the proximal inlet and the distal lead outlet; the lead guide configured so as to permit the lead drive to releasably engage the lead distal end portion, the engagement is releasable such that the lead drive may be released from the lead distal end portion once the lead is attached to the epicardial surface of a heart; (e) a first actuator adapted to articulate the inner suction foot portion and the outer suction foot portion while the inner suction foot portion is disposed within the outer suction foot portion; and (f) a second actuator adapted to articulate the inner suction foot portion when the inner suction foot portion is extended from the outer suction foot portion. This device variant may additionally comprise a lead drive having a flexible distal end and inserted within the inner tubular lead guide so as to extend to the inner tubular lead guide distal end, the flexible distal end bearing a lead, preferably extending through a lead head portion, and having a lead distal end portion, the lead distal end portion extending from the distal end of the lead drive for contact with the epicardial surface of the heart.

Preferably, where the inner tubular lead guide is longer than the outer tubular lead guide, the device may additionally comprise a spacer adapted to maintain the inner suction foot portion within the outer suction foot portion until the inner tubular lead guide is ready to be extended further inside the chest.

This device variant may also preferably include an electrocautery blade extending from between the inner and outer suction foot portions.

Another device variant is one adapted for the thoracoscopic placement of a lead at a target site on an epicardial surface of a heart, the device comprising: (a) an inner tubular lead guide having an inner lead guide distal end comprising an inner suction foot portion, the inner tubular lead guide having a flexible distal end and adapted to conduct a vacuum to the inner suction foot portion; (b) an outer tubular lead guide having an outer lead guide distal end comprising an outer suction foot portion, the outer tubular lead guide having a flexible distal end and adapted to conduct a vacuum to the outer suction foot portion while being adapted to slidingly conduct the inner tubular lead guide, so as to permit the inner tubular lead guide to be extended from the outer lead guide distal end and so as to be moveable a first position wherein the inner suction foot portion is substantially coplanar with the outer suction foot portion to a second position wherein the inner suction foot portion extends beyond the plane of the outer suction foot portion; (c) an elongated sheath body having a longitudinal axis, a proximal end portion and a distal end portion, and having a proximal inlet and a distal lead outlet for extending the inner and outer lead guides therethrough, the elongated sheath body comprising a passageway for receiving and conducting the inner and outer lead guides between the proximal inlet and the distal lead outlet (and ultimately to receive and conduct a lead with lead drive); (d) a first actuator adapted to articulate the inner suction foot portion and the outer suction foot portion while the inner suction foot portion is disposed within the outer suction foot portion; and (e) a second actuator adapted to articulate the inner suction foot portion when the inner suction foot portion is extended from the outer suction foot portion. This variation may also include a lead drive having a flexible distal end and inserted within the inner tubular lead guide so as to extend to the inner tubular lead guide distal end, the flexible distal end bearing a lead extending through the lead drive head and having a lead distal end portion, the lead distal end portion extending from the distal end of the lead drive (and urged beyond the distal end of the inner tubular lead guide) for contact with the epicardial surface of the heart. It preferably also includes an electrocautery blade extending from between the inner and outer suction foot portions.

The device of the present invention also may be appreciated as being adapted for the placement of a conduit at a target site on a tissue surface, the device comprising: (a) dual hollow conduit guides, one inside the other, i.e., the inner conduit guide contained to be extended from within the outer conduit guide, each having a conduit distal end portion and a respective suction foot in fluid communication with the respective hollow conduit guide; (b) a conduit extending through the inner hollow conduit guide, the conduit having a conduit distal end portion; (c) an elongated body having a longitudinal axis, a proximal end portion and a distal end portion, and having a proximal inlet and a distal conduit outlet; the inner conduit guide comprises a conduit receiving passageway for receiving and conducting the conduit with the conduit drive distal end to the inner conduit guide distal conduit outlet; (d) an inner conduit guide suction foot portion releasably attached to the conduit distal end portion, and being in fluid communication with the inner conduit guide, the inner conduit guide suction foot portion articulatably attached to the inner conduit guide distal end portion such that the suction foot may be articulated with respect to the longitudinal axis (the conduit with the conduit drive adapted to releasably engage the suction foot portion such that such engagement is of sufficient strength to maintain the position of the conduit distal end portion as it engages the epicardial surface of a heart or other organ, and sufficiently releasable such that the conduit may be released from the suction foot portion once the conduit is attached to the epicardial surface of a heart or other organ); and (e) an actuator extending from the proximal end portion to the distal end portion and adapted to articulate the suction foot portion with respect to the longitudinal axis both while contained within the outer conduit guide and once extended therefrom.

The conduit may be selected from the group consisting of liquid and gas conduits, such as conductive materials such as wires or fluid-conductive tubules, such conduits adapted to be placed into tissues for electrical or fluid assay and/or biopsy, electrical or fluid testing, electrical actuation, or otherwise to bring about electrical or fluid influence or to determine the level of same. Preferably, such conduits will include coiled plastic or metal tubules.

This device may be provided with a handle portion extending laterally from the elongated body for manual operation, but otherwise may be adapted for robotic use in association with a robotic arm to which it may be readily adapted.

The flexible member in this embodiment, and its nature and operation, may be the same or equivalent to that described above with respect to other embodiments described above. Likewise, the actuator portion, and its nature and operation may be the same or equivalent to that described above with respect to other embodiments described above.

The source of vacuum suction and its cooperation variants with respect to the fluid communication with the conduit guides similarly may be the same or equivalent to that described above with respect to other embodiments described above.

It will be appreciated that in another variation of the invention, that a flexible and resilient conduit portion may extend from the distal end of the hollow conduit guide and thereby also serve as a flexible attachment permitting the suction feet to be articulated while still being of sufficient strength to steer the feet.

The present invention also includes several optional variants including the use of a flexible tip incorporated into the body of the elongated body, such that the device may be adapted for the thoracoscopic placement of a lead at a target site on an epicardial surface of a heart (or the placement of any other conduit into any other type of tissue as described herein).

Other aspects of the device of the present invention and which may be used with the foregoing embodiments include the following:

The device of the present invention may include a suction foot portion that is collapsible and is adapted to be reversibly moved from a stored position within the elongated body to a deployed position outside the elongated body. The collapsible suction foot portion may comprise an array of collapsible fronds adapted to form into a point when in the stored position.

The device of the present invention may include, on the elongated body, a closure lid adapted to reversibly open and close the distal lead outlet.

The foregoing and other objects, features, and advantages of this invention will become more readily apparent from the following detailed description of a preferred embodiment which proceeds with reference to the accompanying drawings, wherein the preferred embodiment of the invention is shown and described, simply by way of illustration of the best mode contemplated of carrying out the invention.

As will be realized, the invention is capable of other and different embodiments, and its several details are capable of modifications in various obvious respects, all without departing from the invention. Accordingly, the drawings and description are to be regarded as illustrative in nature, and not as restrictive. It will also be appreciated that the detailed description represents the preferred embodiment of the invention, and that individual steps of the process of the invention may be practiced independently so as to achieve similar results.

BRIEF DESCRIPTION OF THE DRAWINGS

FIGS. 10A, 10B and 10C are progressive detailed views showing the operation of a device in accordance with one embodiment of the present invention, showing a detailed view of the operation of the device for lead placement. FIG. 10C further shows the position lock of the lead drive disengaged so that the lead drive with lead may be extended in for placement.

DETAILED DESCRIPTION OF THE PREFERRED EMBODIMENTS

In accordance with the foregoing summary, the following provides a detailed description of the preferred embodiment, which is presently considered to be the best mode thereof.

As used herein the distal end refers to the working end or patient end, while the proximal end refers to the operator end or actuator end from which the device of the present invention may be operated. The handle as shown in the described embodiment is on the side of the device referred to as the bottom side or the ventral aspect. The side opposite the bottom side is referred to as the top side or dorsal aspect. The right side is the side on the right hand when looking from the operator end, end-on. Conversely, the left side is the side on the left hand when looking from the operator end, end-on.

Figure 1:
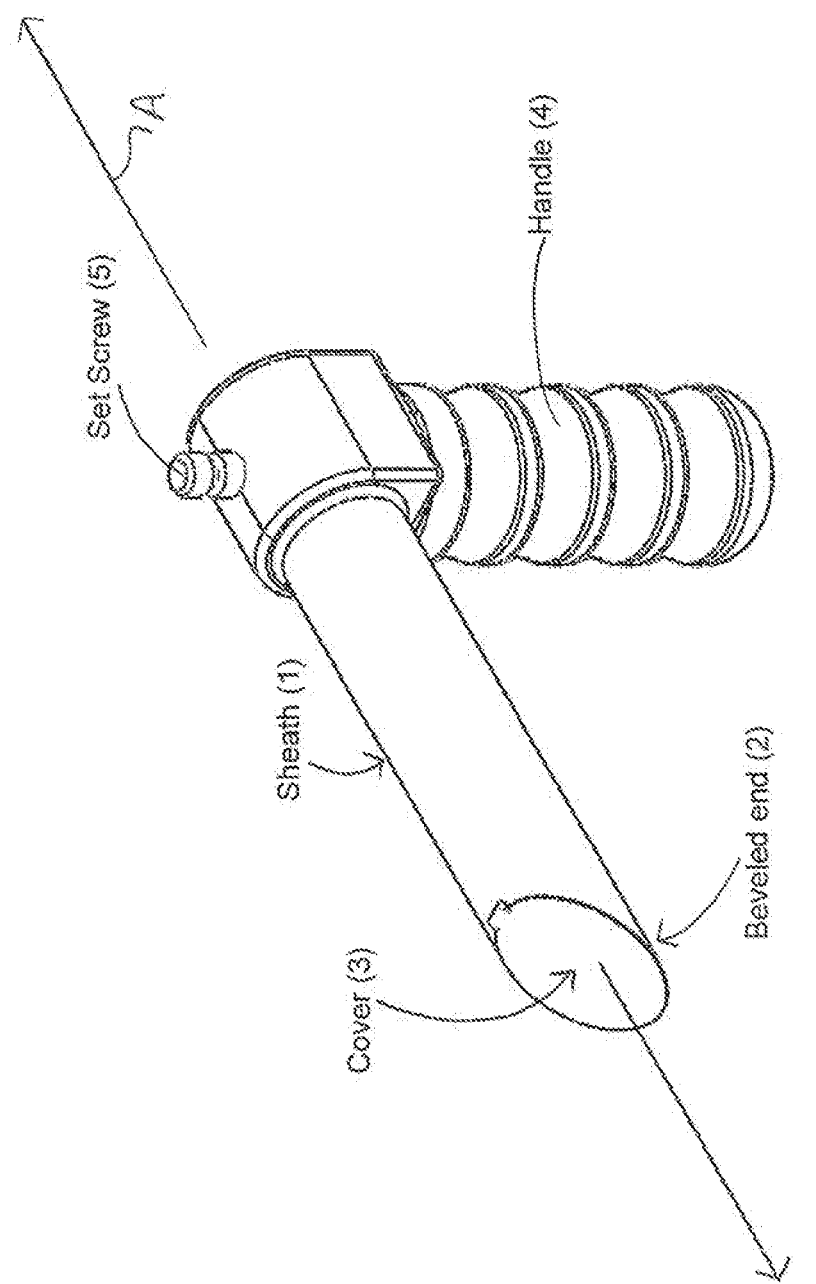
FIG. 1 is a first side lateral perspective view of an elongated sheath body for a device in accordance with one embodiment of the present invention.

FIG. 1 is a first side lateral perspective view of an elongated sheath body 1 for a device in accordance with one embodiment of the present invention, having longitudinal axis A extending from the proximal to distal end. In the preferred embodiment, the sheath 1 is about 15 cms long, and forms a hollow probe made of solid unyielding material such as metal or hard plastic, to gain access into the chest cavity through the access incision in between the ribs. It has a beveled distal end 2 with a spring biased door or cover 3. It has a handle 4 to grasp. It also has a set screw 5 on the top surface of the operator end. This set screw when tightened will hold the outer vacuum tube in a set position (see FIG. 2).

Figure 2:
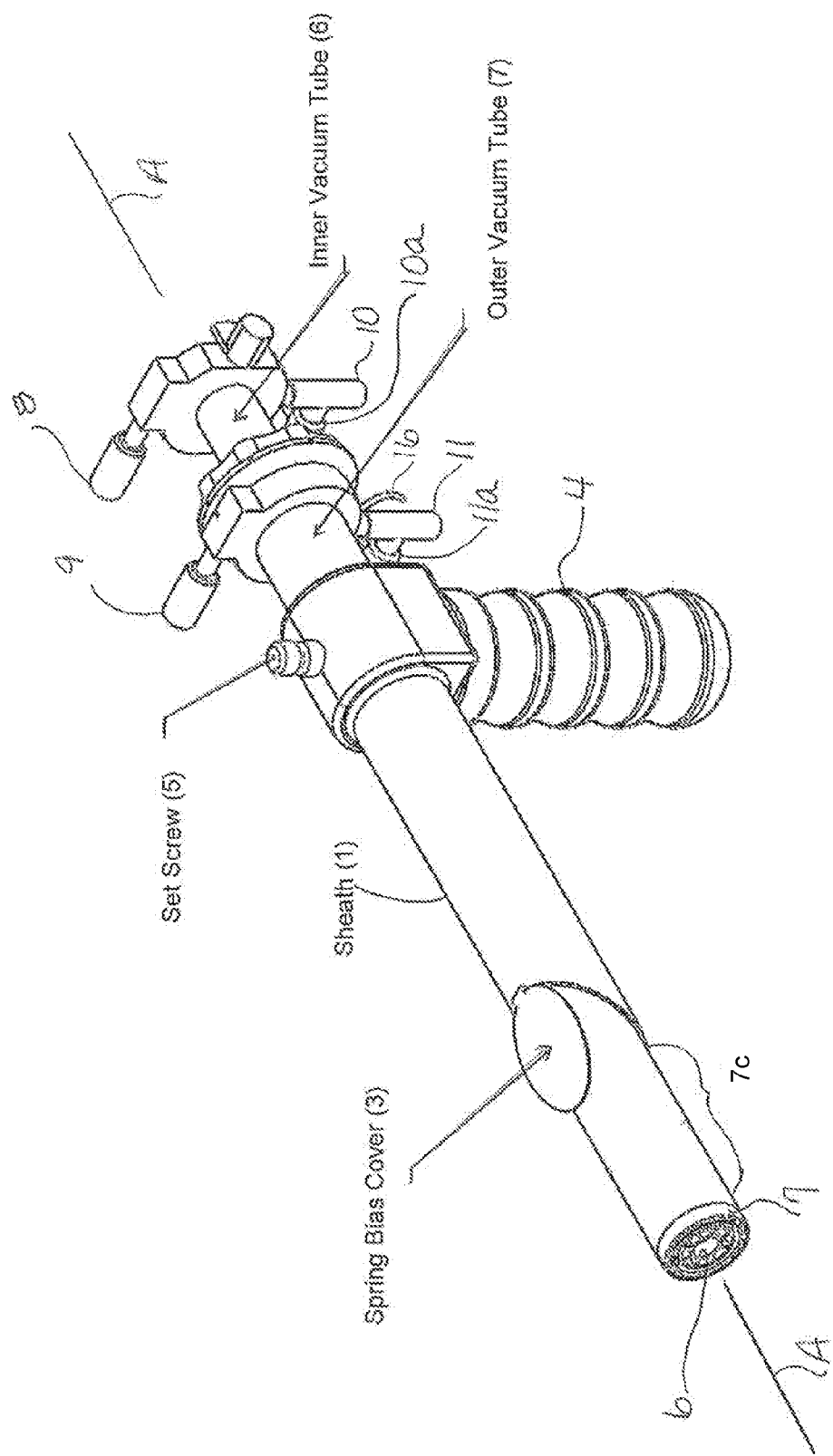
FIG. 2 is a first side lateral perspective view of an entire device in accordance with one embodiment of the present invention, showing the inner and outer tubular lead conduit or guide with respective actuators, and the electrocautery part, in place in the elongated sheath body.

FIG. 2 is a first side lateral perspective view of a device in accordance with one embodiment of the present invention, showing the inner tubular lead conduit or guide 6 and outer tubular lead conduit or guide 7 nested within one another so as to present an even co-terminus suction foot surface on the distal end thereof, with respective actuators 8 and 9, in place in the elongated sheath body 1. The outer tubular lead conduit or guide 7 or outer vacuum tube (OVT) has a length of approximately 30 cms as measured from the handle towards the patient end. The distal or patient end has a suction surface with multiple suction cups formed by the co-terminally aligned suction foot surfaces of the inner tubular lead conduit or guide 6 and outer tubular lead conduit or guide 7, referred to respectively as the inner and outer suction foot portions. The main body of the outer tubular lead conduit or guide 7 preferably is made of a relatively rigid material, while the terminal portion, typically about 4 cms of the distal end thereof (i.e., next to the suction surface) of outer tubular lead conduit or guide 7, is sufficiently flexible to allow it to articulate with respect to the longitudinal axis. This can be achieved by building it with a flat spring with tension cords or hinges or other forms of equivalent articulating mechanical arrangement. The articulating and working lengths may vary.

The proximal or operator end has a connector 11 with a stopcock 11*a* to connect to an outside vacuum tubing to supply vacuum to the outer tubular lead conduit or guide 7. The vacuum or suction or negative pressure is transmitted through the hollow shell of the outer tubular lead conduit or guide 7 to the articulating portion thereof 7A, whereupon it is propagated to the suction cups (comprised by the outer suction foot portion 13) through flexible (plastic) tubing (not shown). The proximal end also has a knob 9 to manipulate articulation of the distal end in one plane. Articulation can be achieved by one, two or more tension cords or other mechanical arrangements to transmit torsional force to the outer tubular lead conduit or guide 7 to bring about articulation. The maximum articulating angle is about 60-70 degrees. Plane of articulation is at right angles to the long axis of the elongated sheath body 1, toward the dorsal-ventral aspect/plane.

Figure 3:
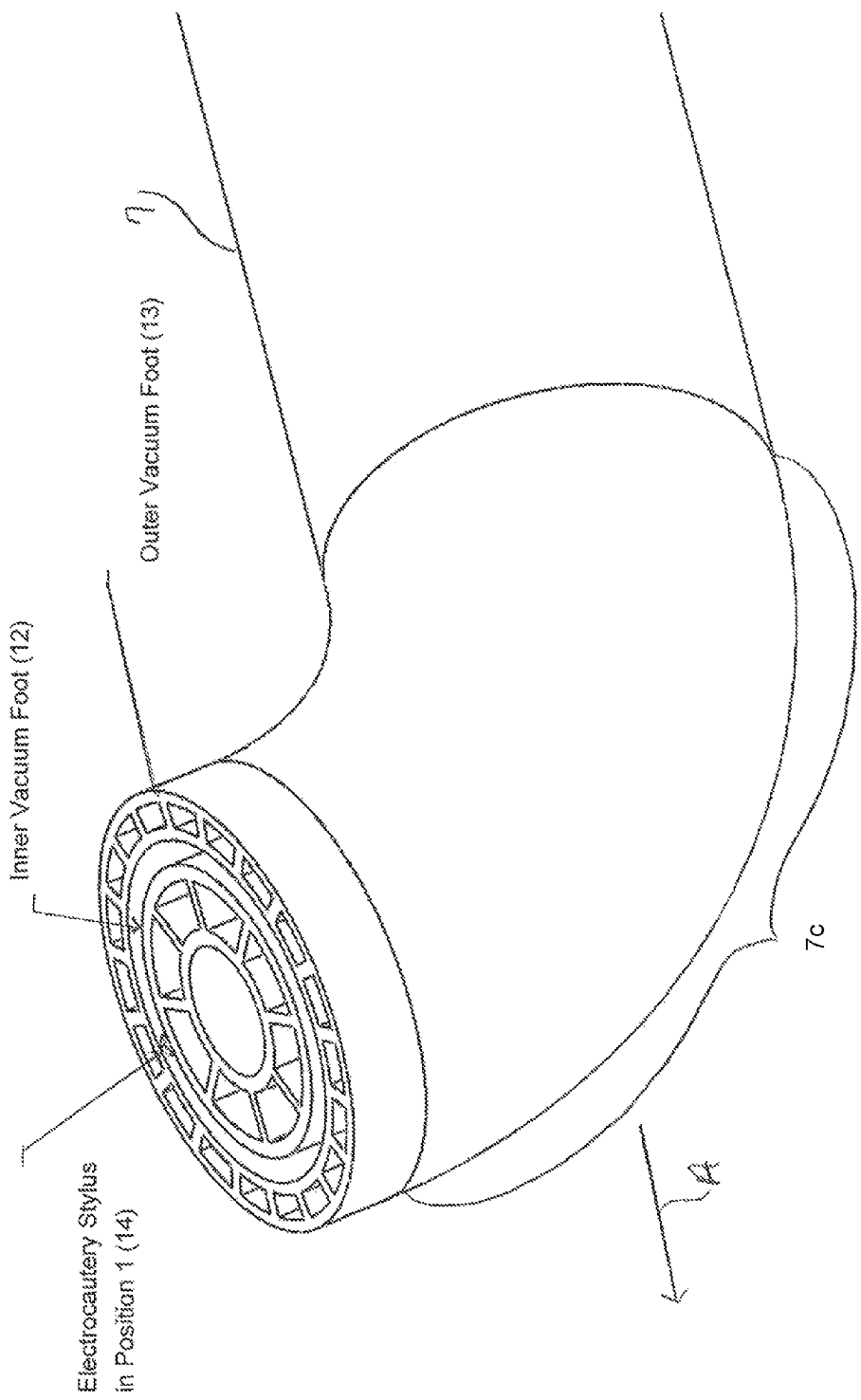
FIG. 3 is a detailed distal end perspective view of a device in accordance with one embodiment of the present invention, and showing the inner and outer tubular lead conduit or guide with respective inner and outer vacuum feet, with the electrocautery blade in a first, recessed position within the inner vacuum foot, and with the articulating distal end of outer tubular lead conduit or guide, bearing with the inner tubular lead conduit or guide, bent at an angle.

FIG. 3 is a detailed distal end perspective view of a device in accordance with one embodiment of the present invention, and showing the inner and outer tubular lead conduits or guides 6 and 7 respectively, with respective inner and outer vacuum feet 12 and 13 respectively, and with the electrocautery blade 14 in a first, recessed position between the inner suction foot portion 12 and the outer suction foot portion 13.

Figure 3A:
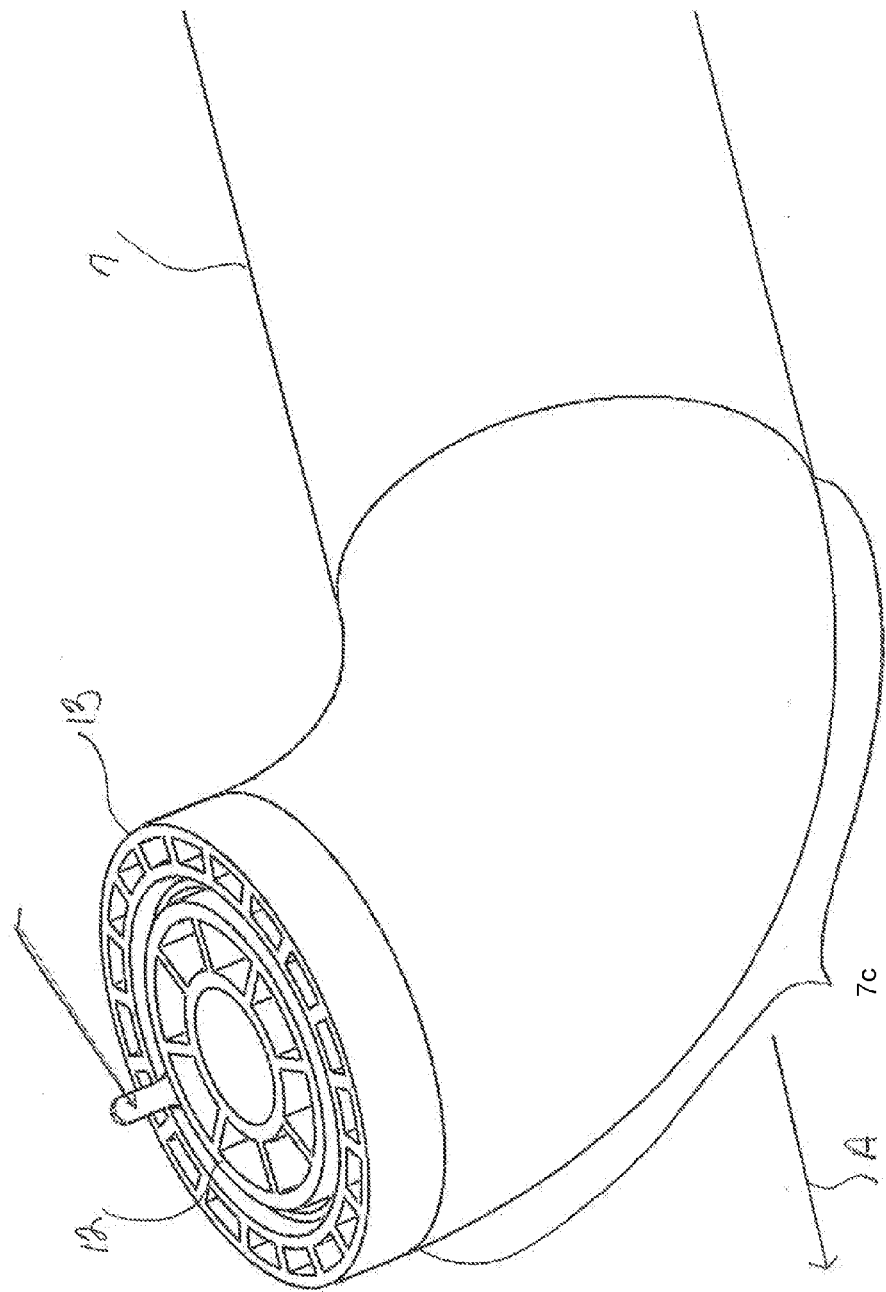
FIG. 3A is a detailed distal end perspective view of a device in accordance with one embodiment of the present invention, and showing the inner and outer tubular lead conduit or guide with respective inner and outer vacuum feet, and with the electrocautery blade in a second position, extending from the inner vacuum foot.

FIG. 3A is a detailed distal end perspective view of a device in accordance with one embodiment of the present invention, and showing the inner and outer tubular lead conduits or guides 6 and 7 respectively, with respective inner and outer vacuum feet 12 and 13 respectively, and with the electrocautery blade 14 in a second position, extending from between the inner suction foot portion 12 and the outer suction foot portion 13.

An external electrical wire 16 connects at the proximal end of the outer tubular lead conduit or guide 7 to a "spring biased contact."

The electrocautery device (EC) is a tube of electrically conducting material that extends from the proximal end of the outer tubular lead conduit or guide 7 to the distal end.

Figure 15:
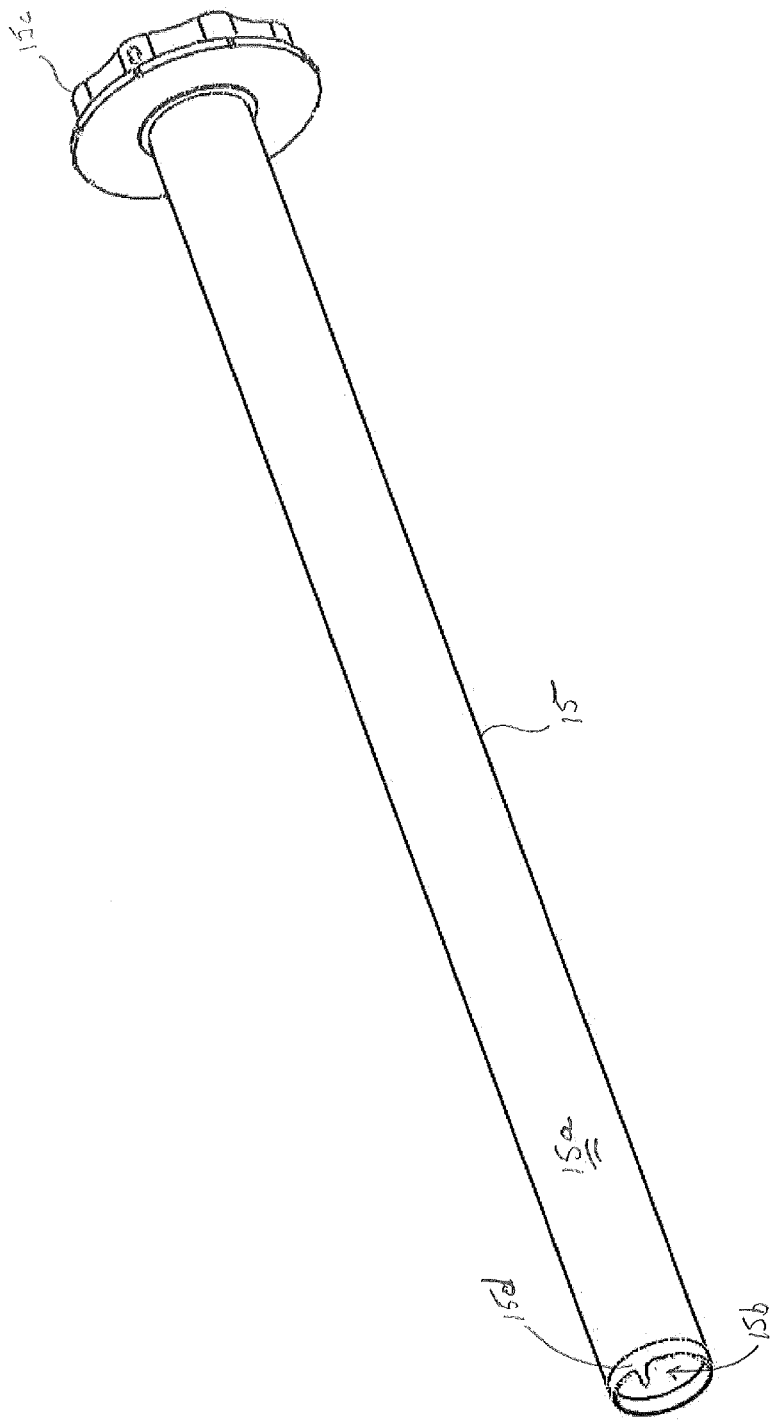
FIG. 15 is a first side lateral perspective view of the control knob and the electrocautery blade portion of a device in accordance with one embodiment of the present invention.
Figure 15A:
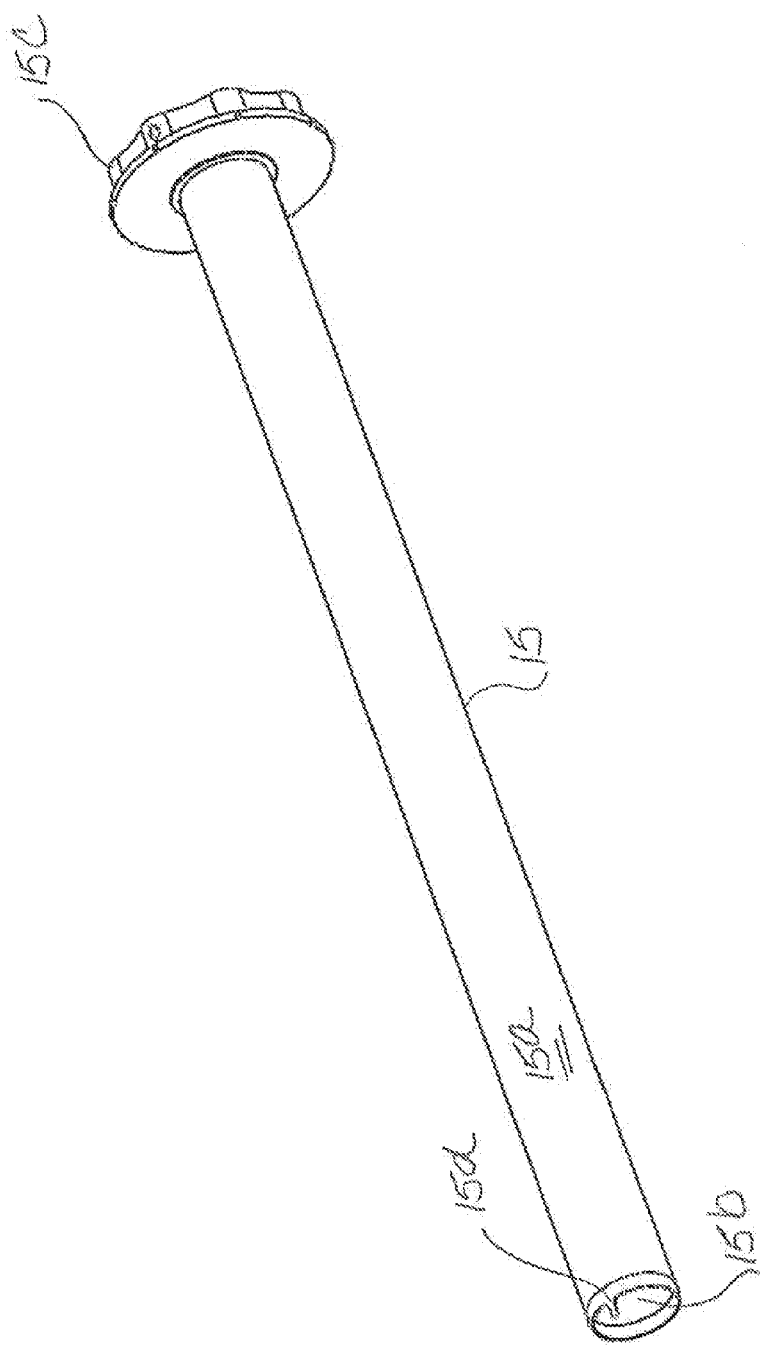
FIG. 15A is another first side lateral perspective view of the control knob and the electrocautery blade portion of a device in accordance with one embodiment of the present invention.

FIGS. 15 and 15A are first side lateral perspective views of the control knob and the electrocautery blade portion 15 of a device in accordance with one embodiment of the present invention.

Figure 16:
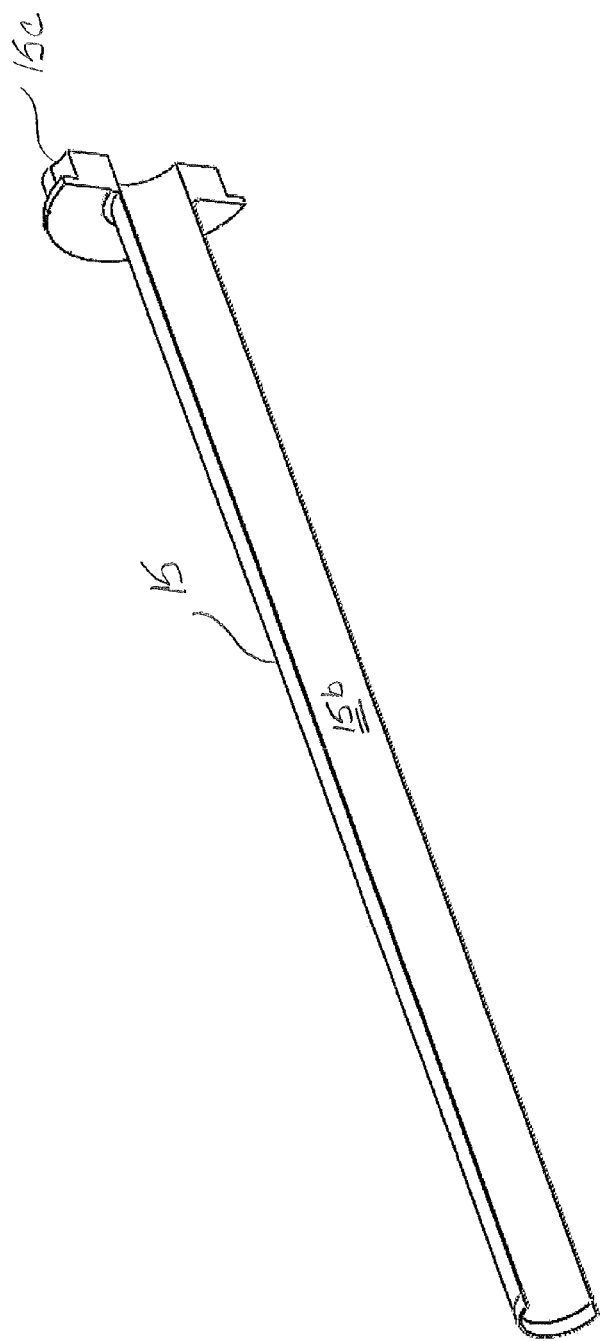
FIG. 16 is a partial first side lateral cross-sectioned perspective view of the control knob and the electrocautery blade portion of a device in accordance with one embodiment of the present invention.
Figure 17:
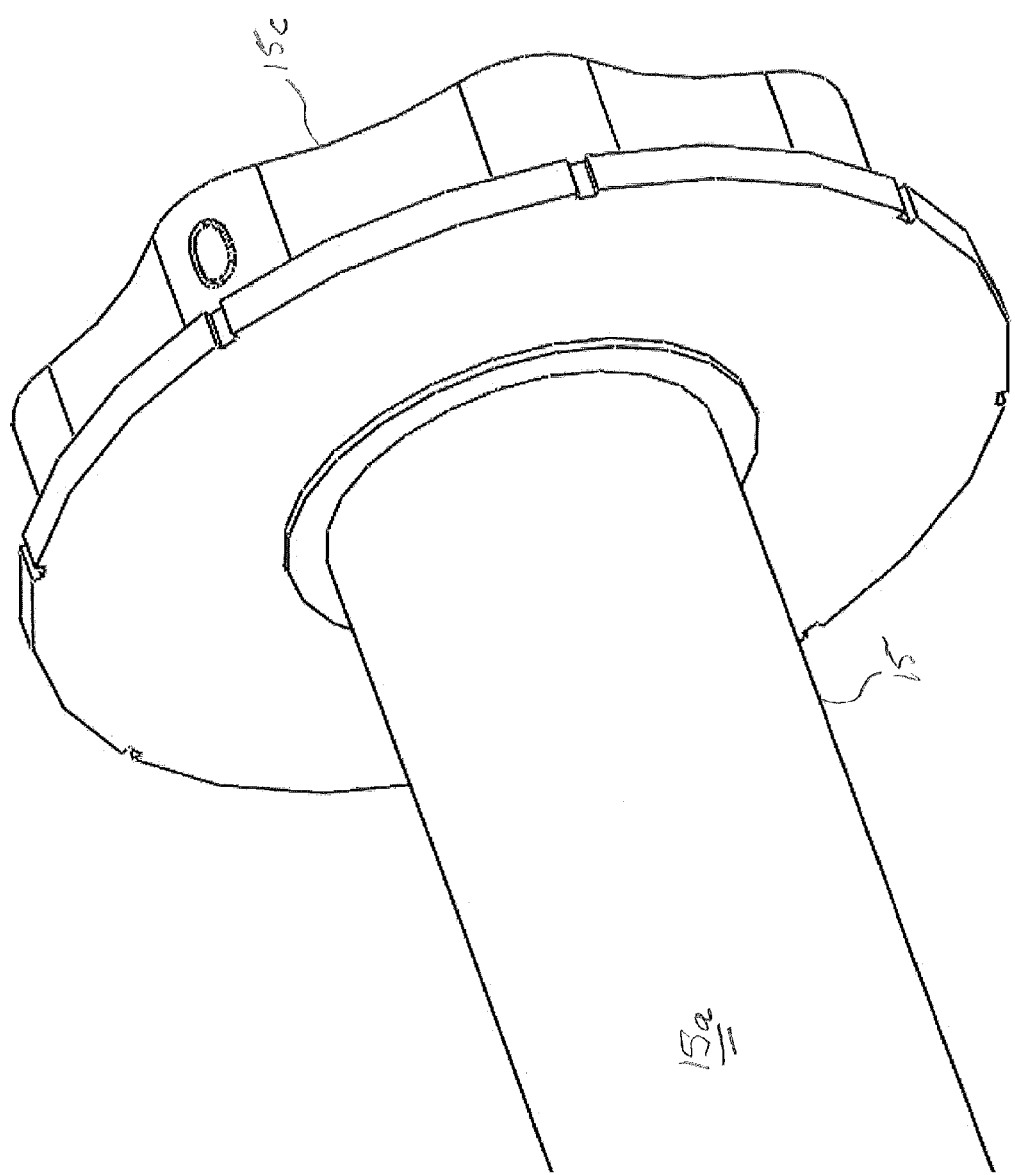
FIG. 17 is a partial first side lateral perspective view of the control knob for the electrocautery blade portion of a device in accordance with one embodiment of the present invention.

FIG. 16 is a partial first side lateral and longitudinally cross-sectioned perspective view of the control knob and the electrocautery blade portion. FIG. 17 is a partial first side lateral perspective view of the control knob for the electrocautery blade portion.

FIGS. 15, 15A, 16 and 17 show the electrocautery device in greater detail, and in which like reference numerals refer to corresponding portions thereof. Its inner surface 15*b* and outer surface 15*a* are insulated. The distal end has an un-insulated stylus 15*d* that is 3 mm long and 1.5 to 2 mm wide. This stylus 15*d* can be pushed out and rotated 360 degrees with cutting electric energy by action of control wheel 15*c*.

Figure 4:
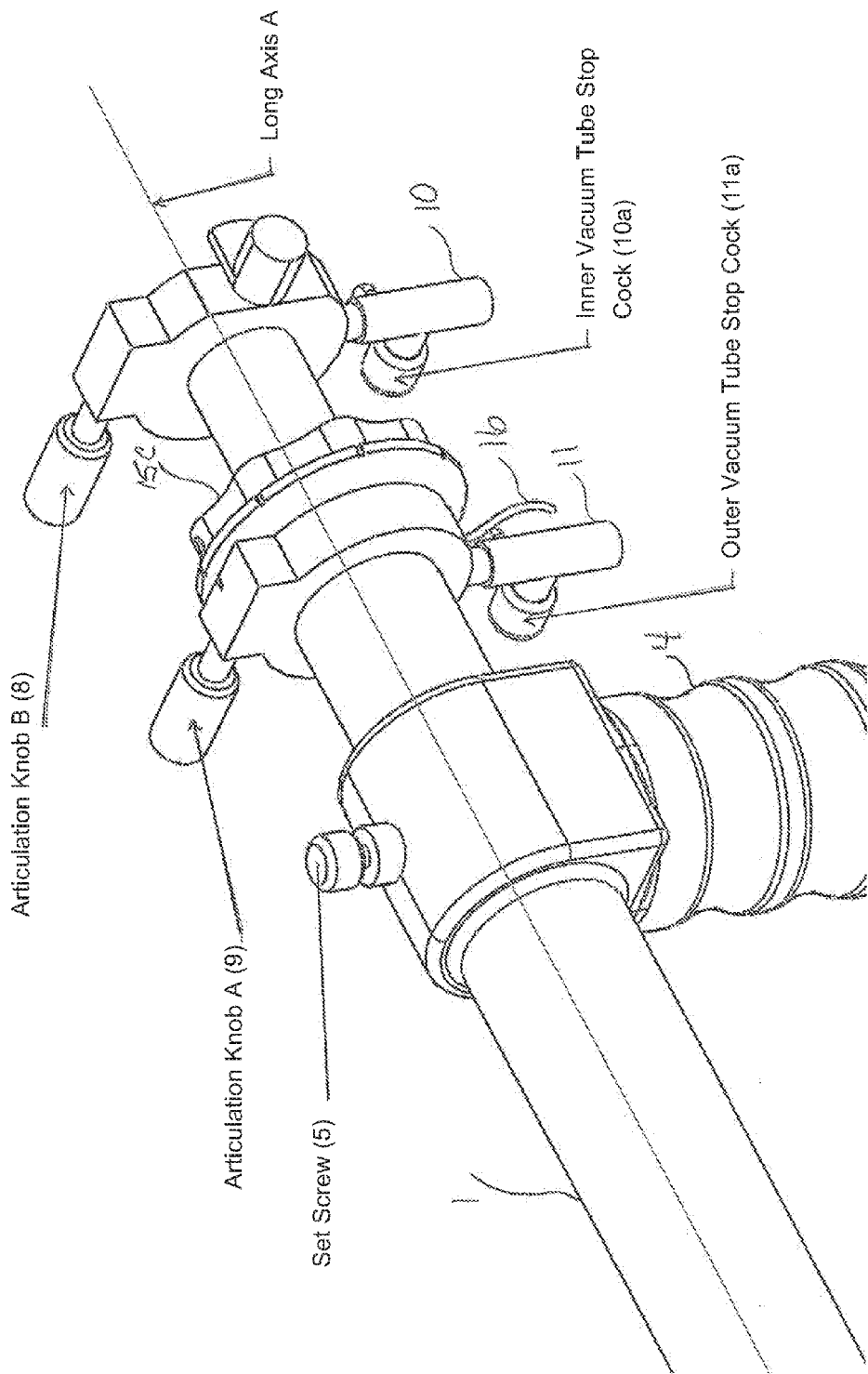
FIG. 4 is a detailed distal end perspective view of a device in accordance with one embodiment of the present invention, and showing the inner and outer tubular lead conduit or guide with respective actuators in the form of articulation knobs, as well as respective inner and outer vacuum tube stopcocks.

FIG. 4 is a detailed distal end perspective view of the proximal end of the device in accordance with one embodiment of the present invention. This view shows the inner and outer tubular lead conduits or guides 6 and 7 assembled within the elongated sheath body 1, with respective actuators in the form of articulation knobs 8 and 9, respectively, as well as respective connection to inner and outer vacuum tubes 10 and 11 with associated stopcocks 10*a* and 11*a*. This view shows set screw 5 holding outer tubular lead conduit or guide 7 in place within elongated sheath body 1, and with electrocautery device nested in between the inner and outer tubular lead conduits or guides 6 and 7, and control wheel 15*c* exposed.

Figure 5:
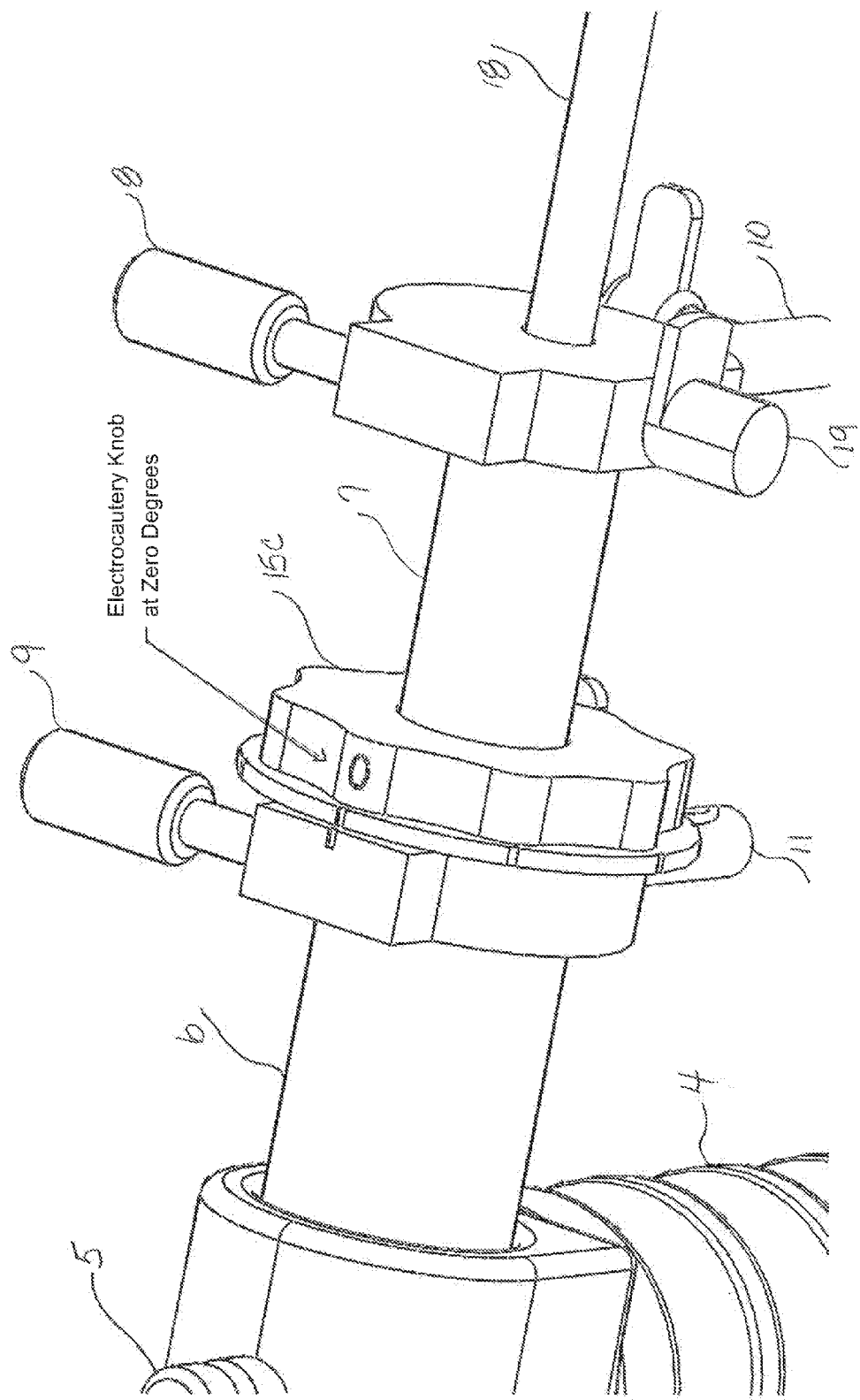
FIG. 5 is a detailed proximal end perspective view of a device in accordance with one embodiment of the present invention, and showing the inner and outer tubular lead conduit or guide with respective actuators in the form of articulation knobs and connection for suction with a stopcock, and showing the control knob for the electrocautery blade in-between the proximal ends of outer and the inner vacuum tubes/tubular lead conduit. The electrocautery knob is in the form of a wheel that may be turned clockwise. It preferably has markings on it to record a full 360 degree turn of the electrocautery blade.

FIG. 5 is a detailed proximal end perspective view of a device in accordance with one embodiment of the present invention, and showing the inner and outer tubular lead conduits or guides 6 and 7 assembled within the elongated sheath body 1 as shown in FIG. 4. This view also shows the position of lead drive 18 as it would be inserted along axis A of the device during the lead insertion and placement operation.

Figure 6:
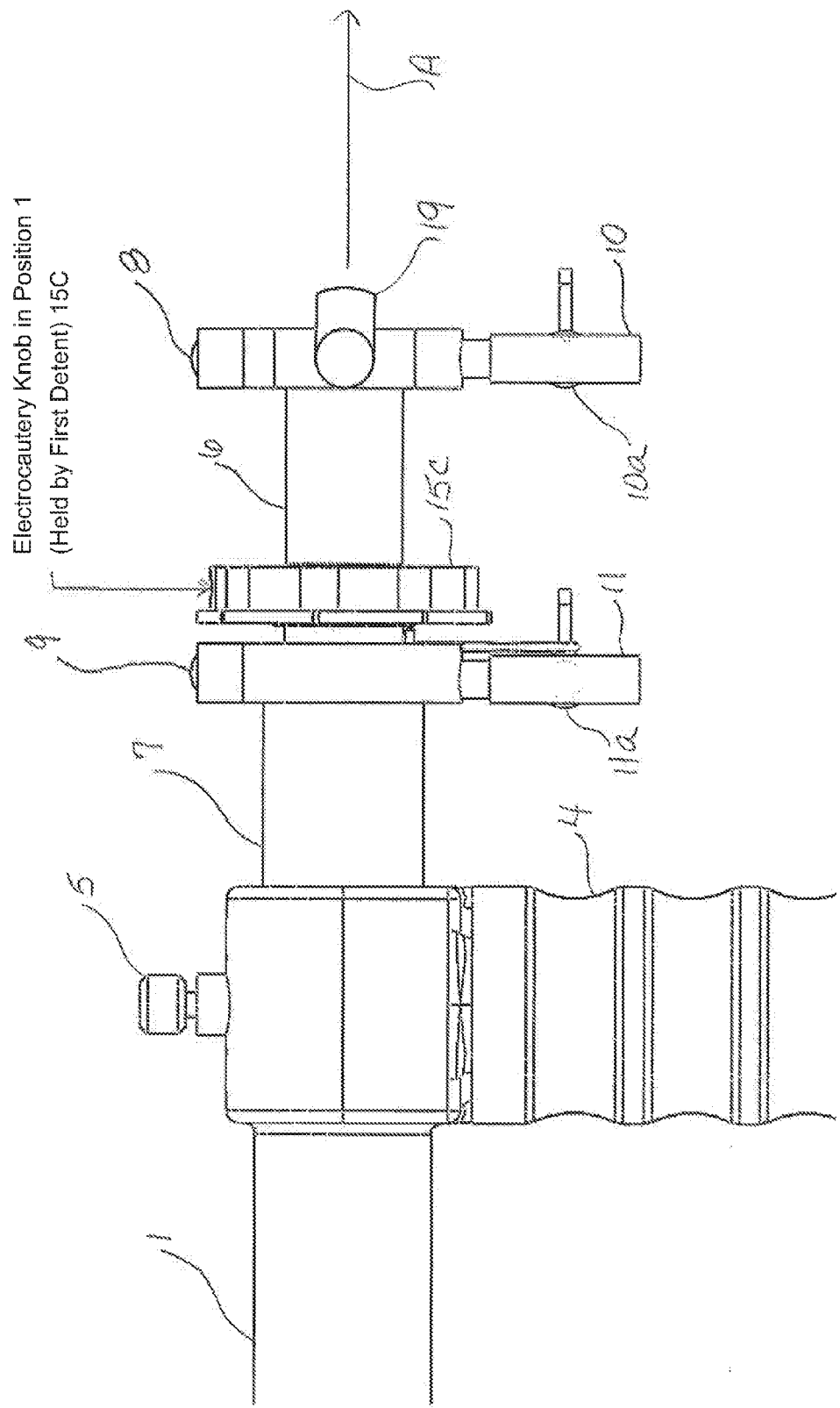
FIG. 6 is a detailed proximal end elevation view of a device in accordance with one embodiment of the present invention, and showing the inner and outer tubular lead conduits or guides with respective actuators in the form of articulation knobs and connection for suction with a stopcock, and showing the control knob for the electrocautery blade extending from the inner vacuum foot held in a first position by a first detent.
Figure 7:
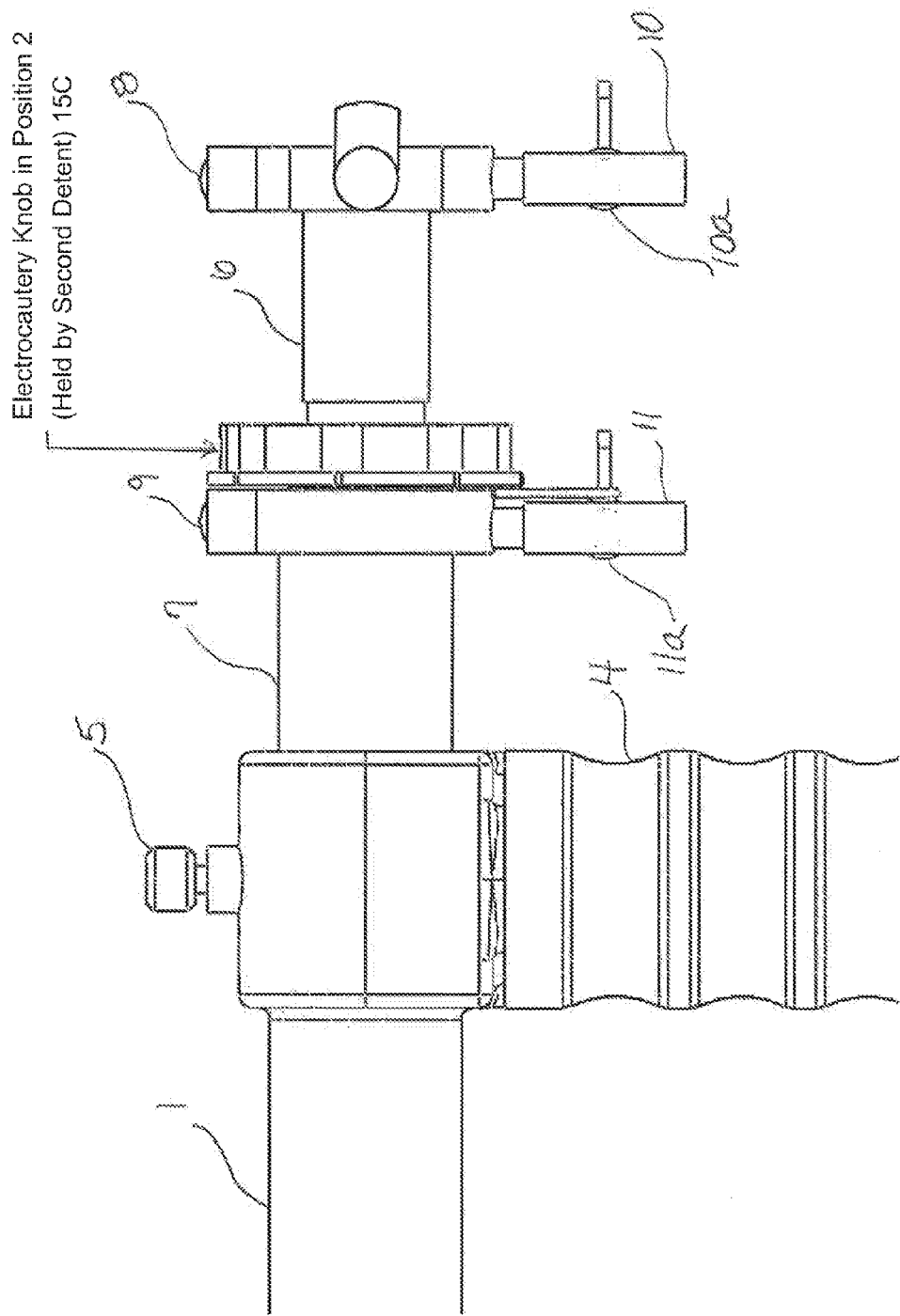
FIG. 7 is a detailed proximal end elevation view of a device in accordance with one embodiment of the present invention, and showing the inner and outer tubular lead conduits or guides with respective actuators in the form of articulation knobs, and showing the control knob for the electrocautery blade extending from the inner vacuum foot held in a second position by a second detent.

FIGS. 6 and 7 show the proximal end of the device and show the two positions (stylus protruded FIG. 6 and withdrawn FIG. 7) held by a detent on control wheel 15*c*. The proximal end has an electrocautery contact ring on the distal surface of the proximal wheel. When the electrocautery contact is pushed into the "stylus protruded position" on the detent, the electrocautery contact ring comes in contact with the spring biased contact on outer tubular lead conduit or guide 7 and the electrocautery contact becomes energized. The proximal end also has a control wheel 15*c* that allows the electrocautery contact with stylus to rotate 360 degrees to cut the pericardium. There is a zero mark on the wheel which coincides with a zero mark on the proximal end of the outer tubular lead conduit or guide 7.

Figure 8:
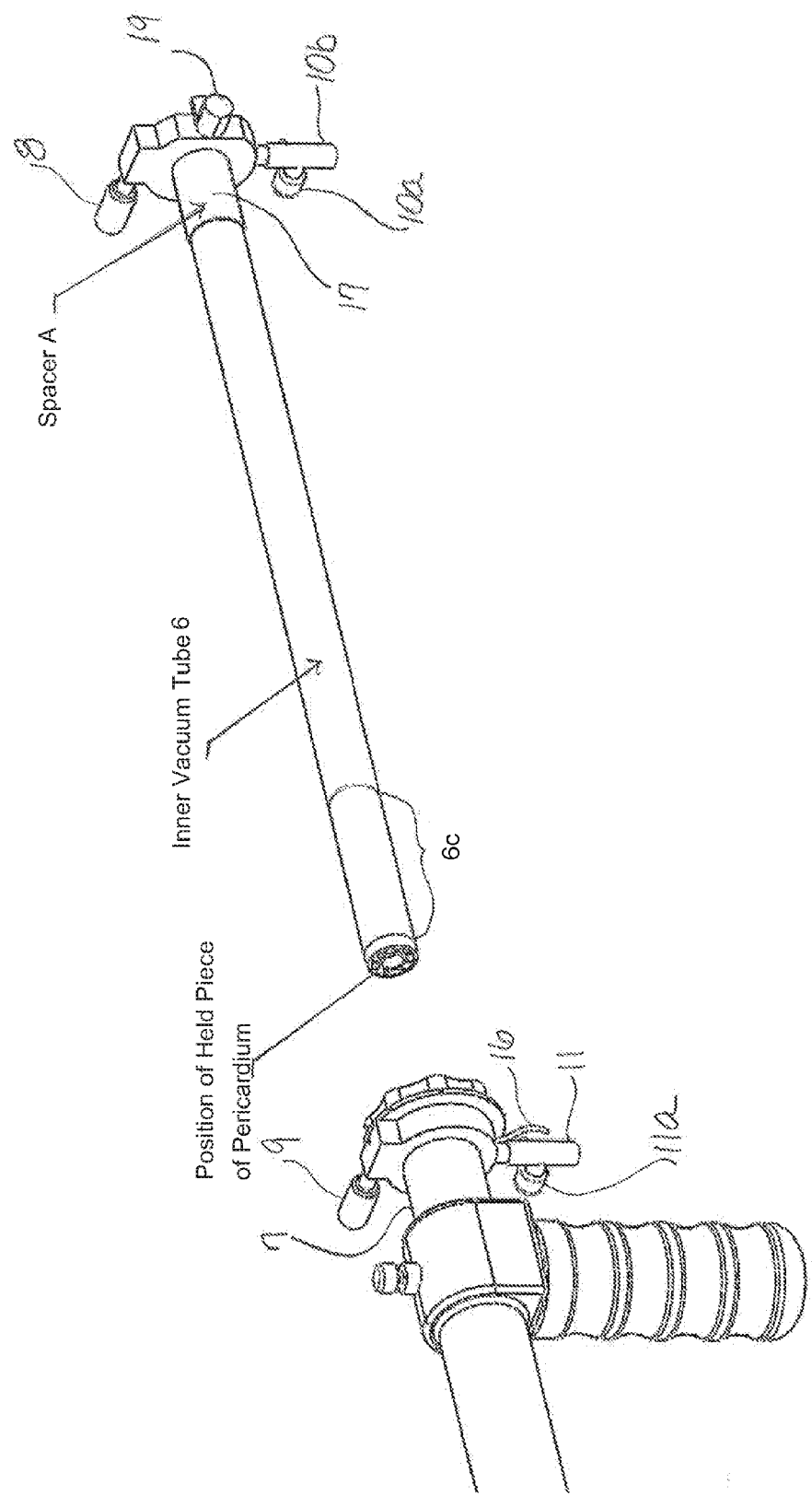
FIG. 8 is a first side lateral exploded perspective view of a device in accordance with one embodiment of the present invention, showing the inner tubular lead conduit, with extension-restricting spacer in place, and withdrawn from the outer tubular lead conduit or guide residing in the elongated body sheath, and showing with respective actuators for the tubular guides.

FIG. 8 is a first side lateral exploded perspective view of a device in accordance with one embodiment of the present invention in which like reference numerals refer to corresponding portions thereof, showing the inner tubular lead conduit or guide 6, with extension-restricting spacer 17 in place, and withdrawn from the outer tubular lead conduit or guide 7 residing in the elongated body sheath 1, and showing with respective actuators 8 and 9 for the inner and outer tubular guides 6 and 7.

The inner tubular guide 6 or inner vacuum tube (IVT) fit inside the electrocautery contact device and has a suction surface in the distal end, made of multiple suction cups in the form of inner suction foot portion 12. The main body of the inner tubular guide 6 is made of hard material and 7 cms of distal end of the inner tubular guide 6 (i.e., that nearest to the suction surface) are flexible, allowing it to articulate with respect to the longitudinal axis A. This can be achieved, for instance, by building it with a flat spring with tension cords or hinges or other forms of articulation through equivalent mechanical arrangements. The width and specification of the springs preferably will be adjusted so that there is no hindrance of one spring articulating inside the other. The articulating and working lengths can vary. The proximal or operator end of the inner tubular guide 6 has a connector 10 with a stopcock 10*a* to connect to outside vacuum tubing. The vacuum or suction or negative pressure is transmitted through the hollow shell of the inner tubular guide 6 to the articulating portion 6*a*, whereupon it is propagated to the suction cups of inner suction foot portion 12 through flexible (plastic) tubing. The proximal end of the inner tubular guide 6 also has a knob 8 to manipulate articulation of the distal end in one plane. Articulation can be achieved by 1, 2 or more tension cords or other methods. Maximum articulating angle is about 30 degrees. The plane of articulation is at right angles to the long axis A of the elongated sheath body 1, toward the right-left aspect/plane. At the proximal end, there is a spacer 17 of about 3 cm length, that prevents the inner tubular guide 6 from protruding beyond the outer tubular guide 7, and maintains both suction surfaces of inner suction foot portion 12 and outer suction foot portion 13 in the same plane. Once the cut piece of pericardium has been removed, the spacer is removed from the inner tubular guide 6, the lead drive 18 with lead 20 is then loaded into the device.

Figure 9:
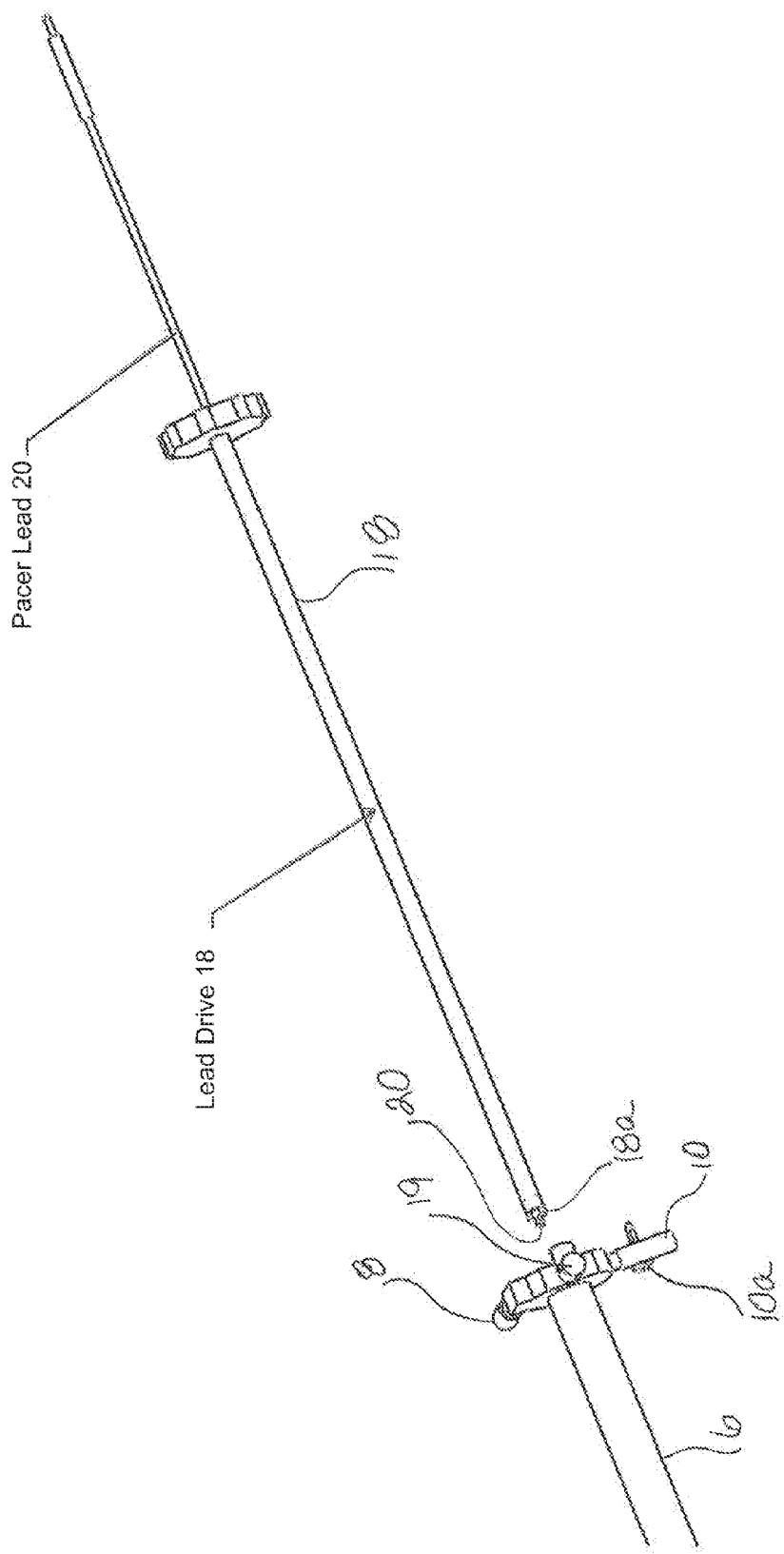
FIG. 9 is a first side lateral exploded perspective view of portions of a device in accordance with one embodiment of the present invention, showing the cardiac lead drive engaged over the cardiac lead, and not yet inserted into the inner tubular lead conduit.

FIG. 9 is a first side lateral exploded perspective view of portions of a device in accordance with one embodiment of the present invention, showing the cardiac lead drive 18 engaged over the cardiac lead 20, and not yet inserted into the inner tubular lead conduit or guide 6. The position lock 19 is in the engaged position.

Figure 9A:
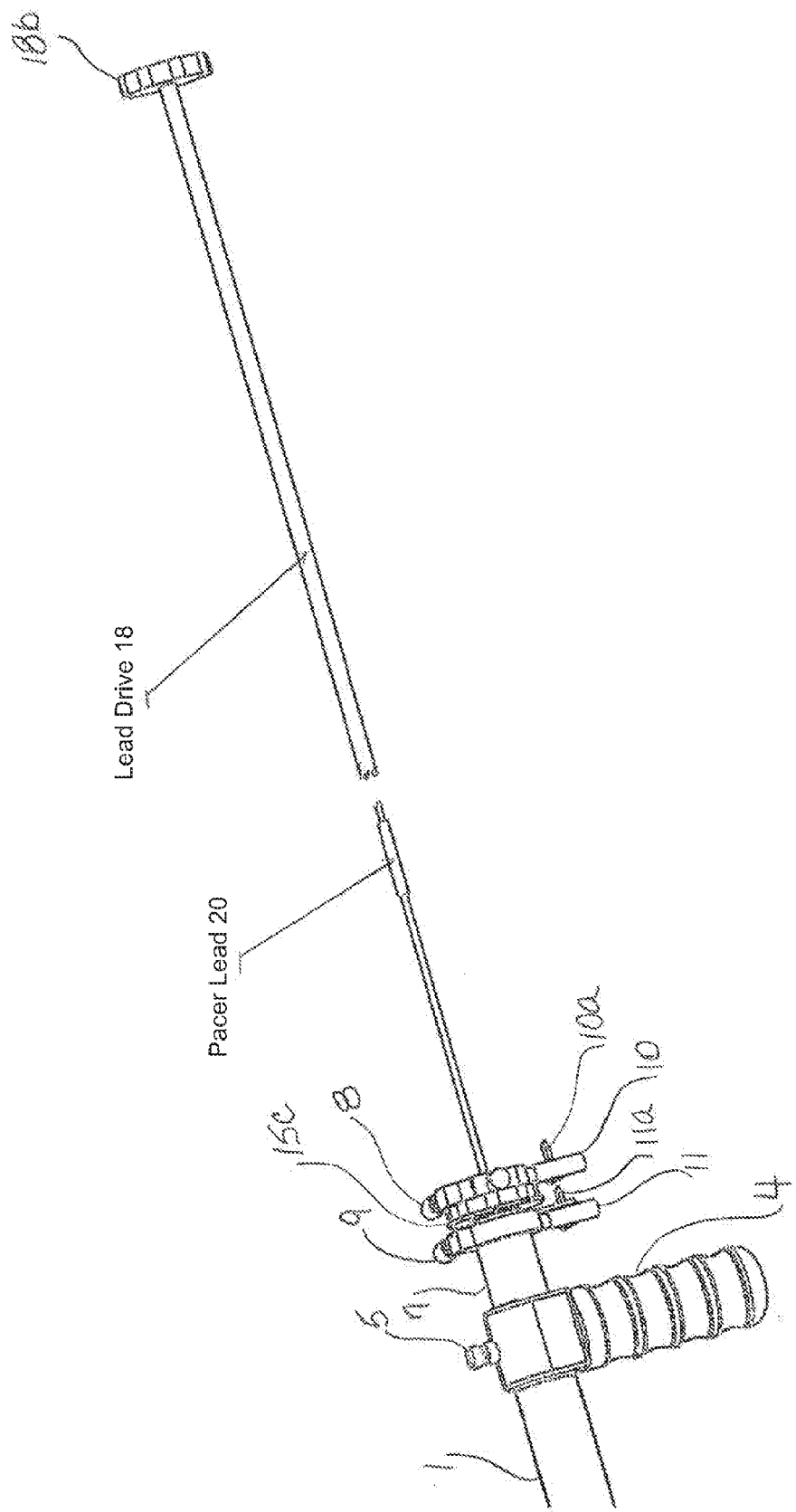
FIG. 9A is a first side lateral exploded perspective view of portions of a device in accordance with one embodiment of the present invention, showing the cardiac lead drive further withdrawn from over the cardiac lead, after placement through inner tubular lead conduit.

FIG. 9A is a first side lateral exploded perspective view of portions of a device in accordance with one embodiment of the present invention, showing the cardiac lead drive 18 further withdrawn from over the cardiac lead 20, after placement through inner tubular lead conduit or guide 6. The position lock 19 is in the disengaged position.

Figure 9B:
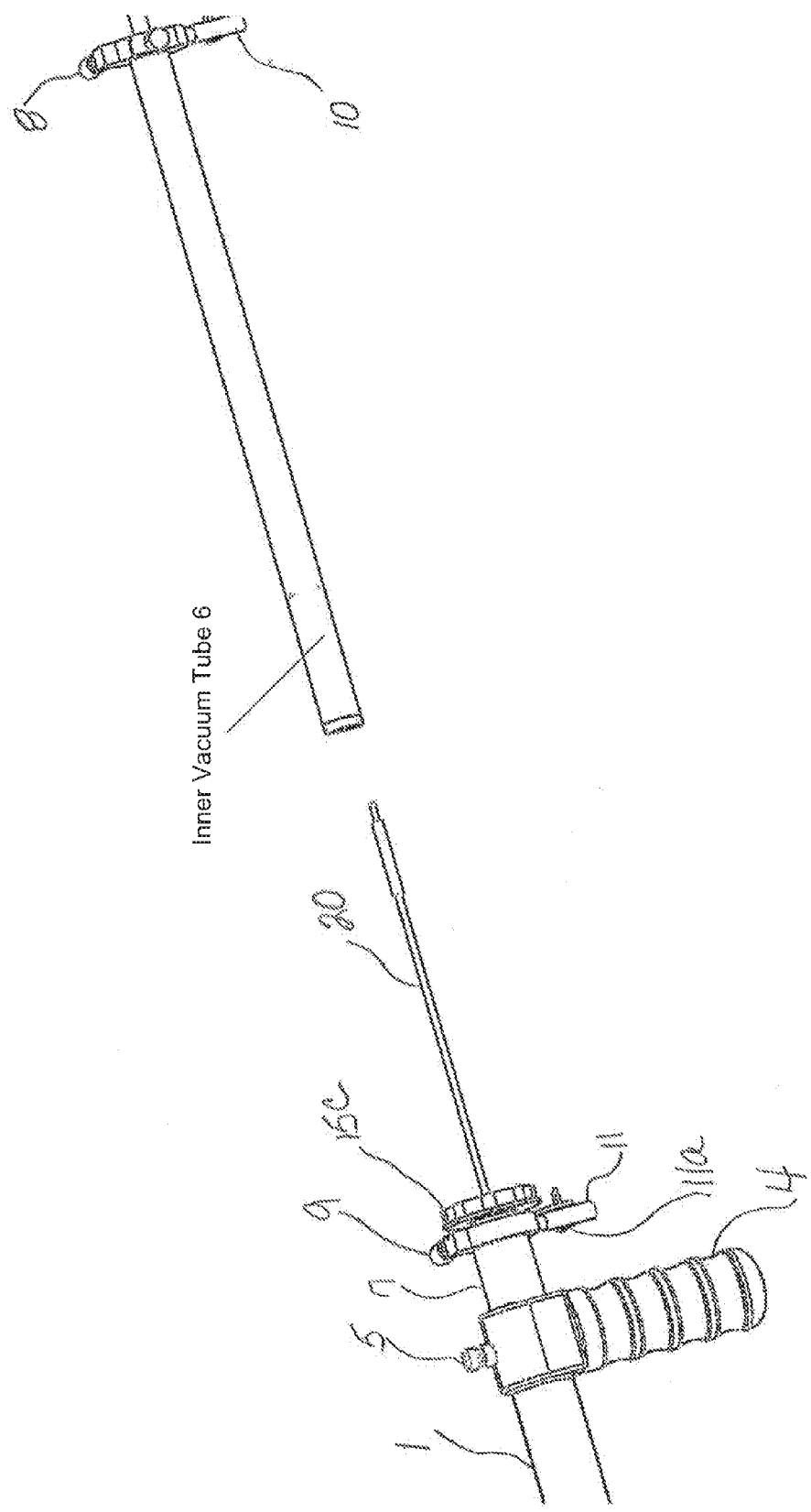
FIG. 9B is a first side lateral exploded perspective view of portions of a device in accordance with one embodiment of the present invention, showing the inner tubular lead conduit or guide further withdrawn from over the cardiac lead, after lead placement.

FIG. 9B is a first side lateral exploded perspective view of portions of a device in accordance with one embodiment of the present invention, showing the inner tubular lead conduit or guide 6 further withdrawn from over the cardiac lead 20, after placement thereof.

Figure 9C:
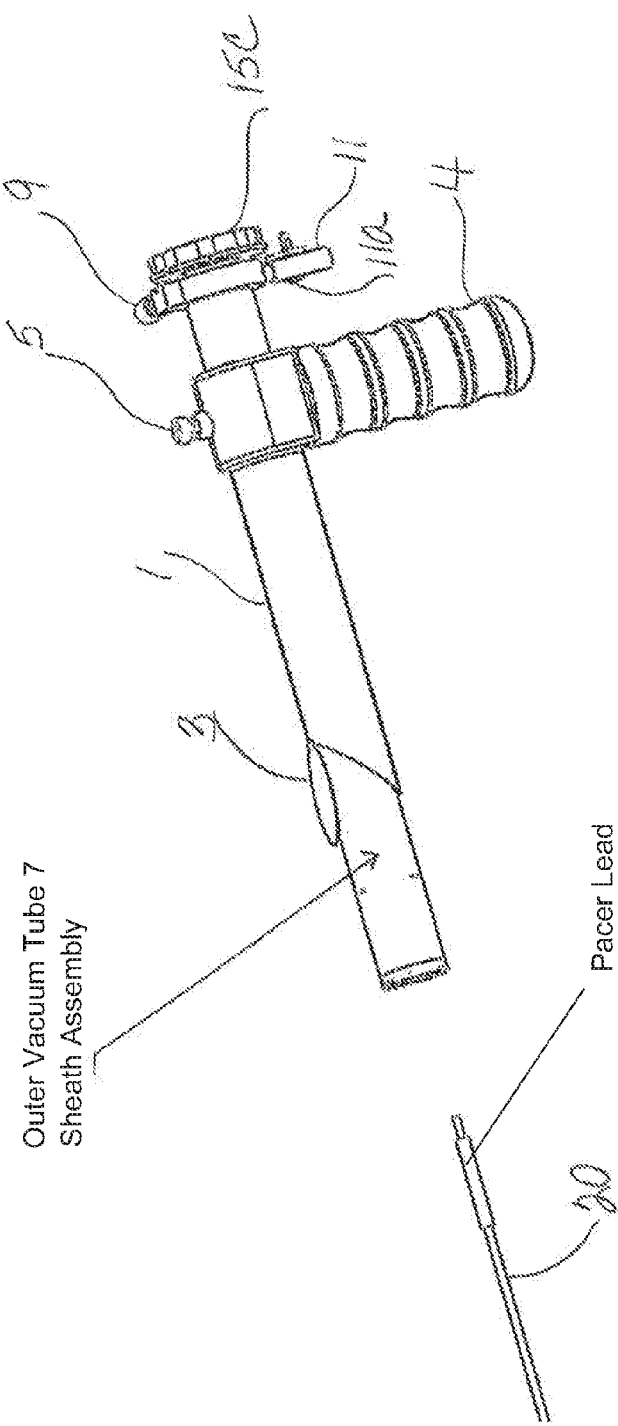
FIG. 9C is a first side lateral exploded perspective view of portions of a device in accordance with one embodiment of the present invention, showing the elongated sheath body with outer tubular lead conduit or guide further withdrawn from over the cardiac lead, after placement.

FIG. 9C is a first side lateral exploded perspective view of portions of a device in accordance with one embodiment of the present invention, showing the elongated sheath body 1 with outer tubular lead conduit or guide further withdrawn from over the cardiac lead 20, after placement thereof.

Figure 10:
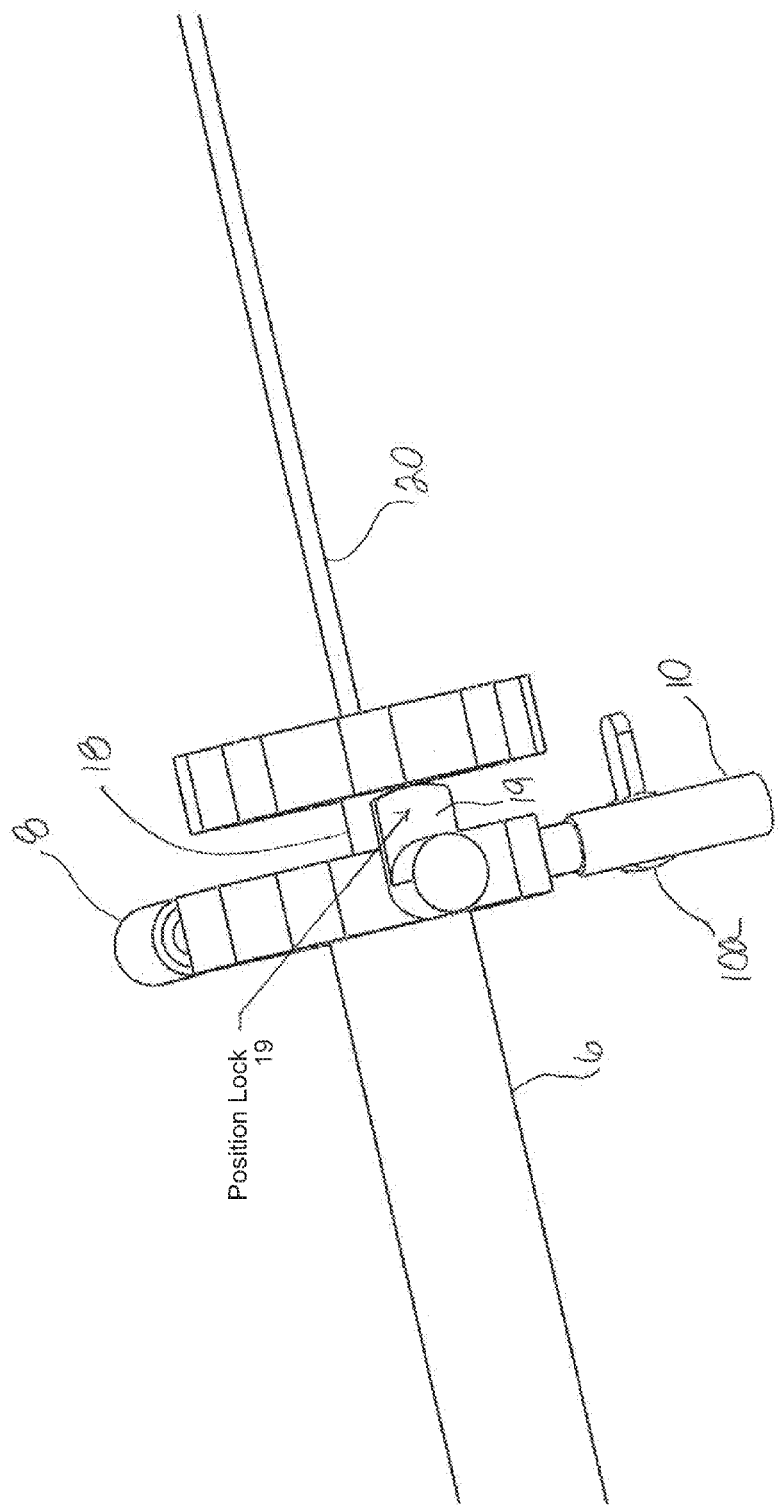
FIG. 10 is a detailed first side lateral perspective view of portions of a device in accordance with one embodiment of the present invention, showing the cardiac lead drive (with the lead inside it) extending into the inner tubular lead conduit, and showing the position lock to hold the cardiac lead drive in position with respect to the inner tubular guide.

FIG. 10 is a detailed first side lateral perspective view of portions of a device in accordance with one embodiment of the present invention, showing the cardiac lead drive 18 extending into the inner tubular lead conduit or guide 6, and showing the position lock 19 to hold the cardiac lead drive 18 in position with respect to the inner tubular guide 6.

Figure 10B:
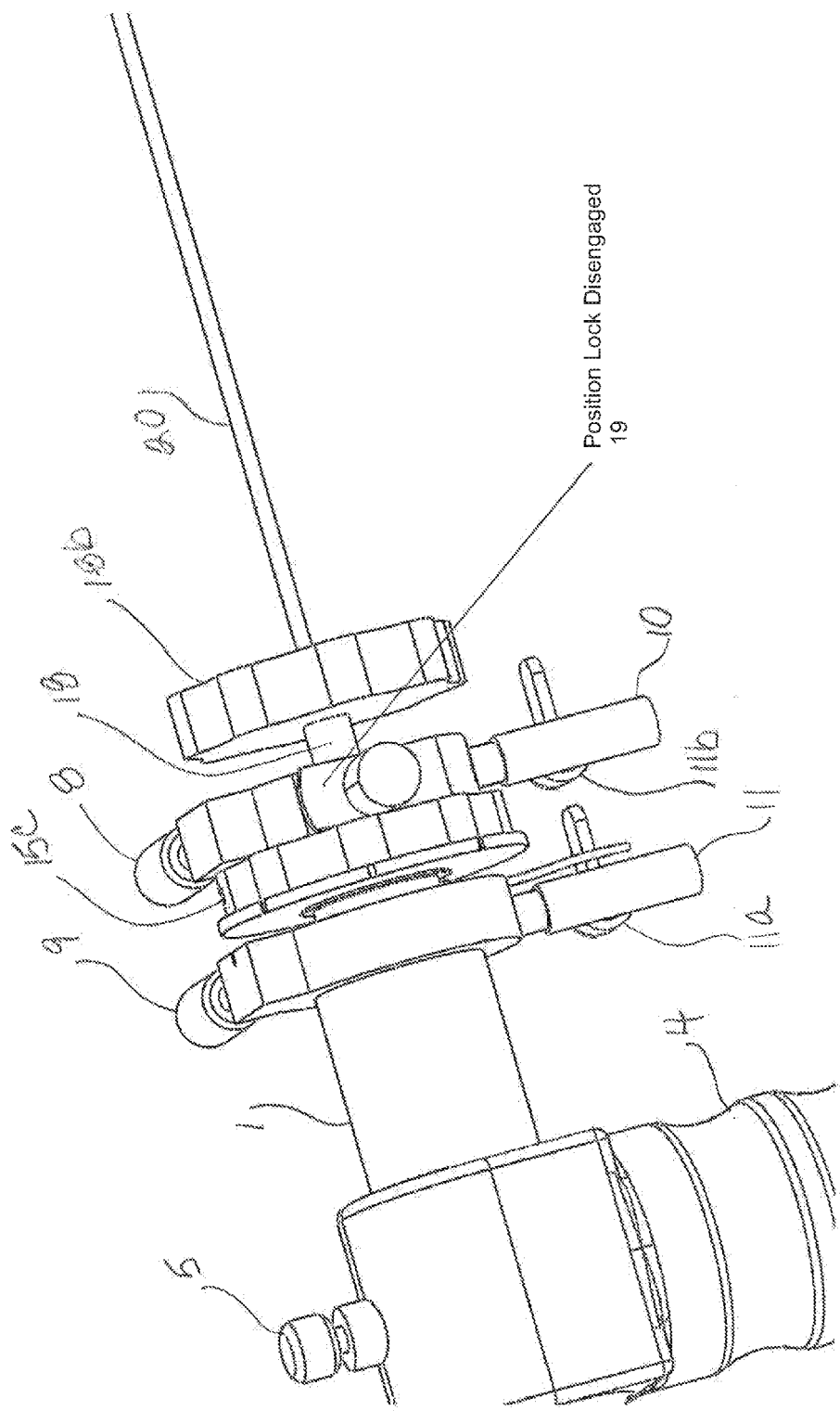

FIGS. 10A, 10B and 10C are progressive detailed views showing the operation of a device in accordance with one embodiment of the present invention, showing a detailed view of the lead placement series. The action of the position lock 19 may be appreciated by comparing FIGS. 10A and 10B, showing the position lock 19 in the engaged and disengaged positions respectively. FIG. 10C shows the position lock 19 in the disengaged position, and further show the direction of axial force brought about by rotational movement of lead drive wheel 18b for lead placement.

Figure 11:
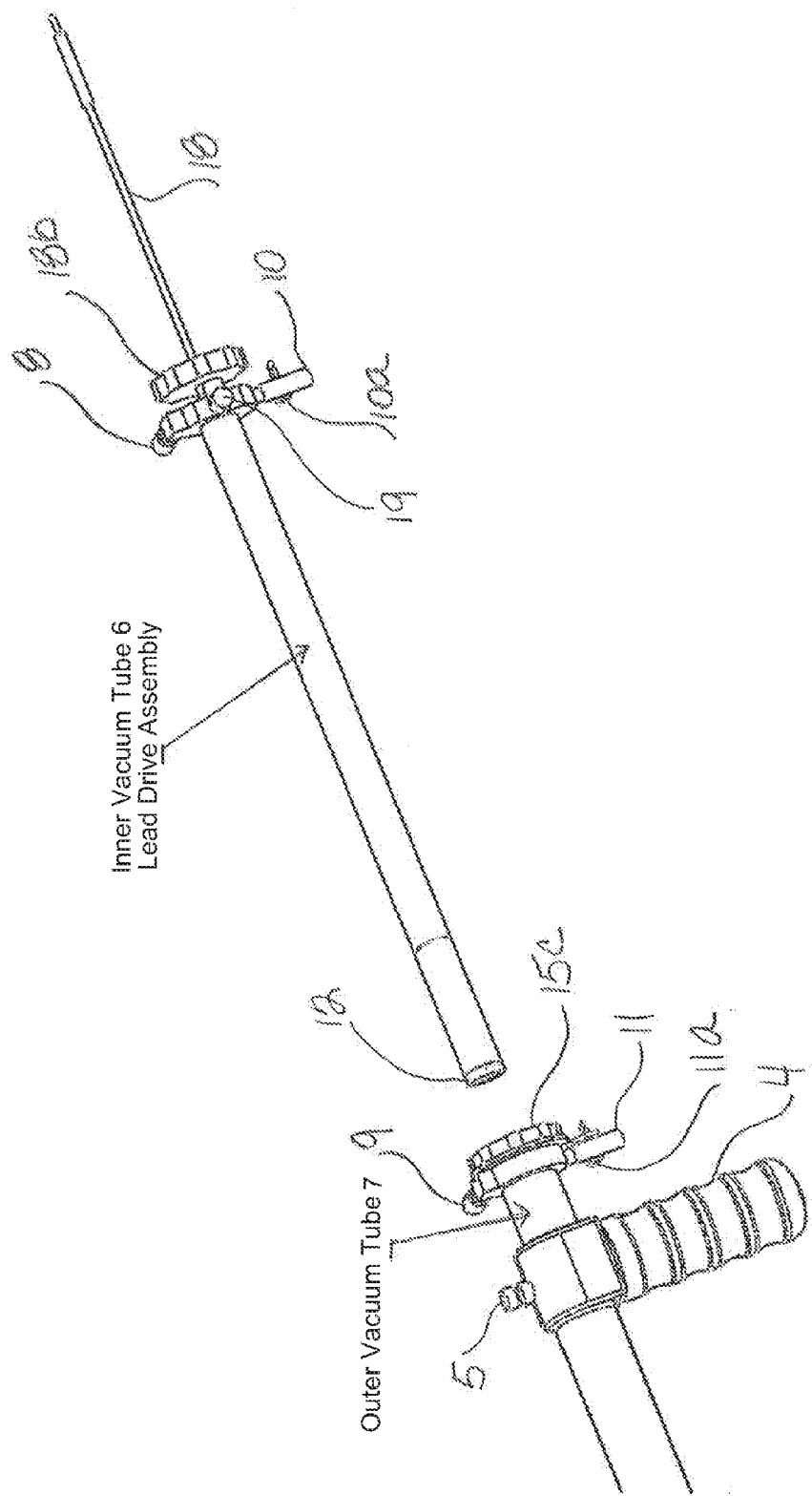
FIG. 11 is a first side lateral exploded perspective view of portions of a device in accordance with one embodiment of the present invention, showing the inner tubular lead conduit or guide withdrawn from the outer tubular lead conduit or guide residing in the elongated body sheath, and showing the cardiac lead drive locked in a position with respect to the inner tubular lead conduit.
Figure 11A:
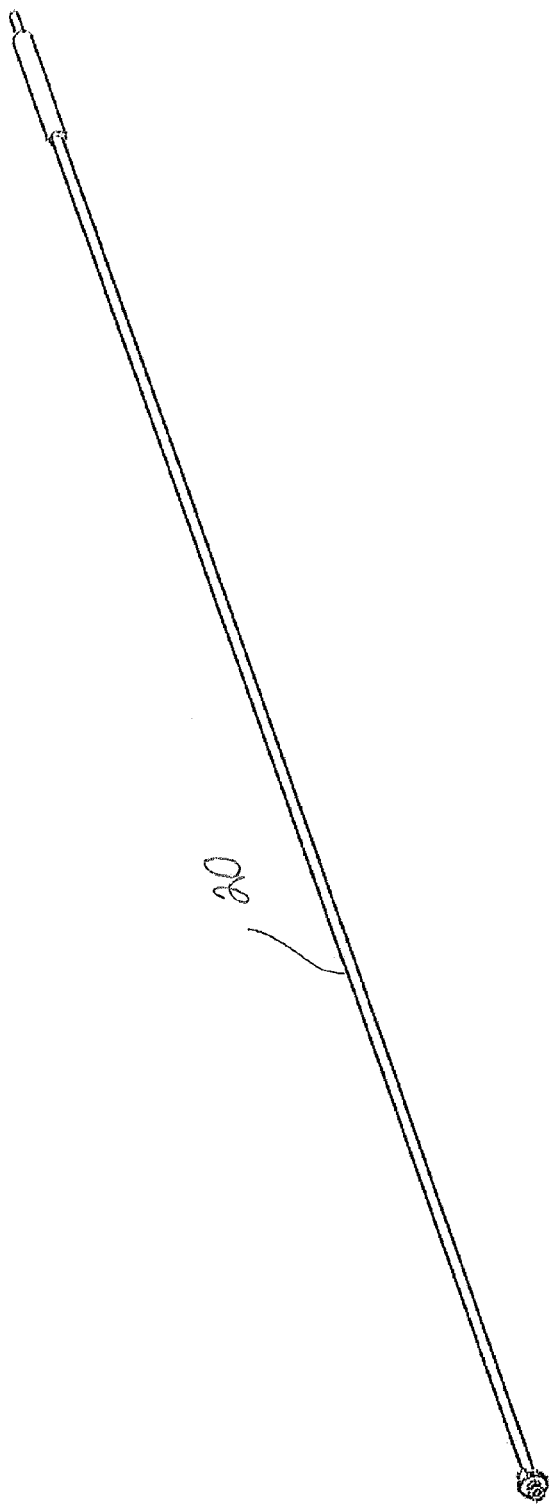
FIG. 11A is a detailed first side lateral perspective view of the cardiac lead withdrawn from the lead drive.

FIG. 11 is a first side lateral exploded perspective view of portions of a device in accordance with one embodiment of the present invention, showing the inner tubular lead conduit or guide 6 withdrawn from the outer tubular lead conduit or guide 7 residing in the elongated body sheath 1, and showing the cardiac lead drive 18 locked in a position with respect to the inner tubular lead conduit or guide 6. FIG. 11A is a detailed first side lateral perspective view of the cardiac lead 20 withdrawn from the inner tubular lead conduit or guide 6.

Figure 12:
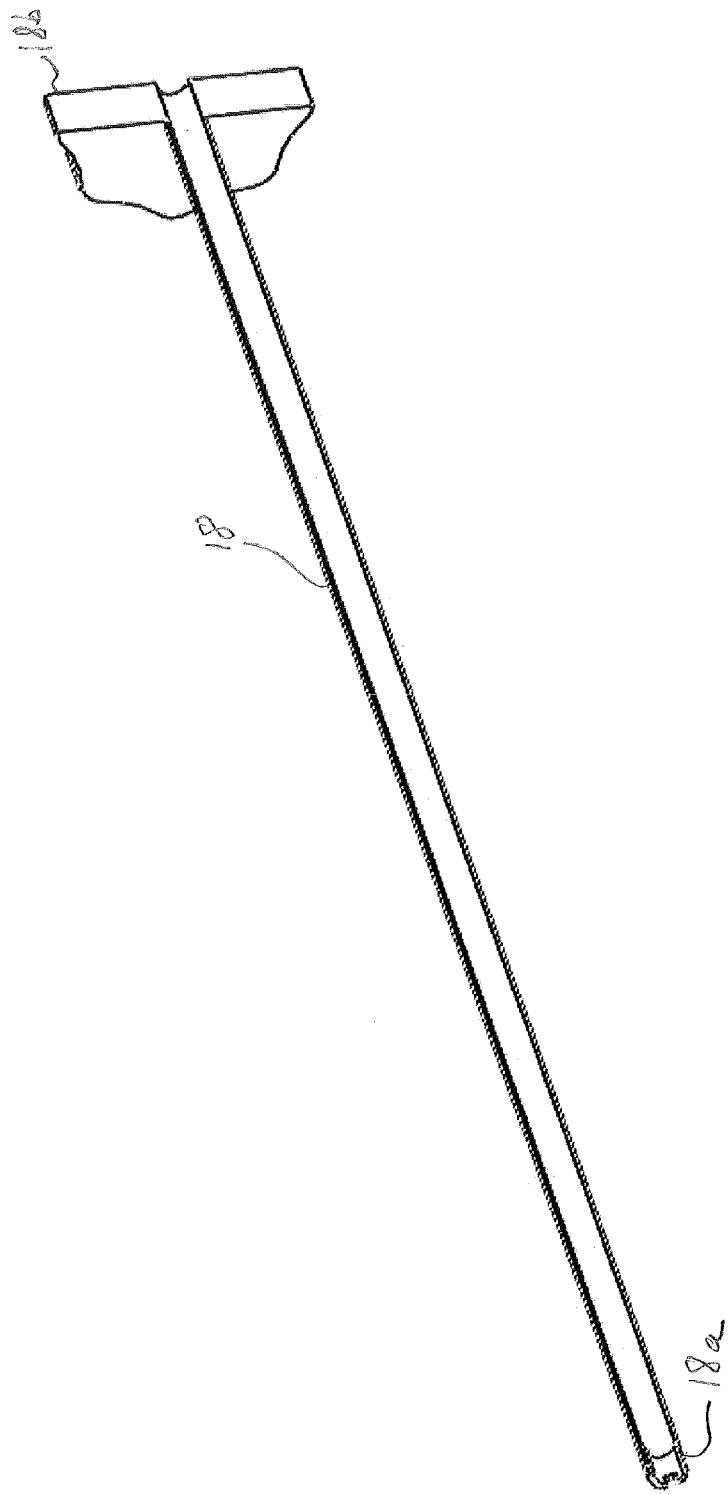
FIG. 12 is a first side lateral cross-section perspective view of a cardiac lead drive portion of a device, in accordance with one embodiment of the present invention.

FIG. 12 is a first side lateral cross-section perspective view of a cardiac lead drive 18 portion of a device, in accordance with one embodiment of the present invention.

Figure 13:
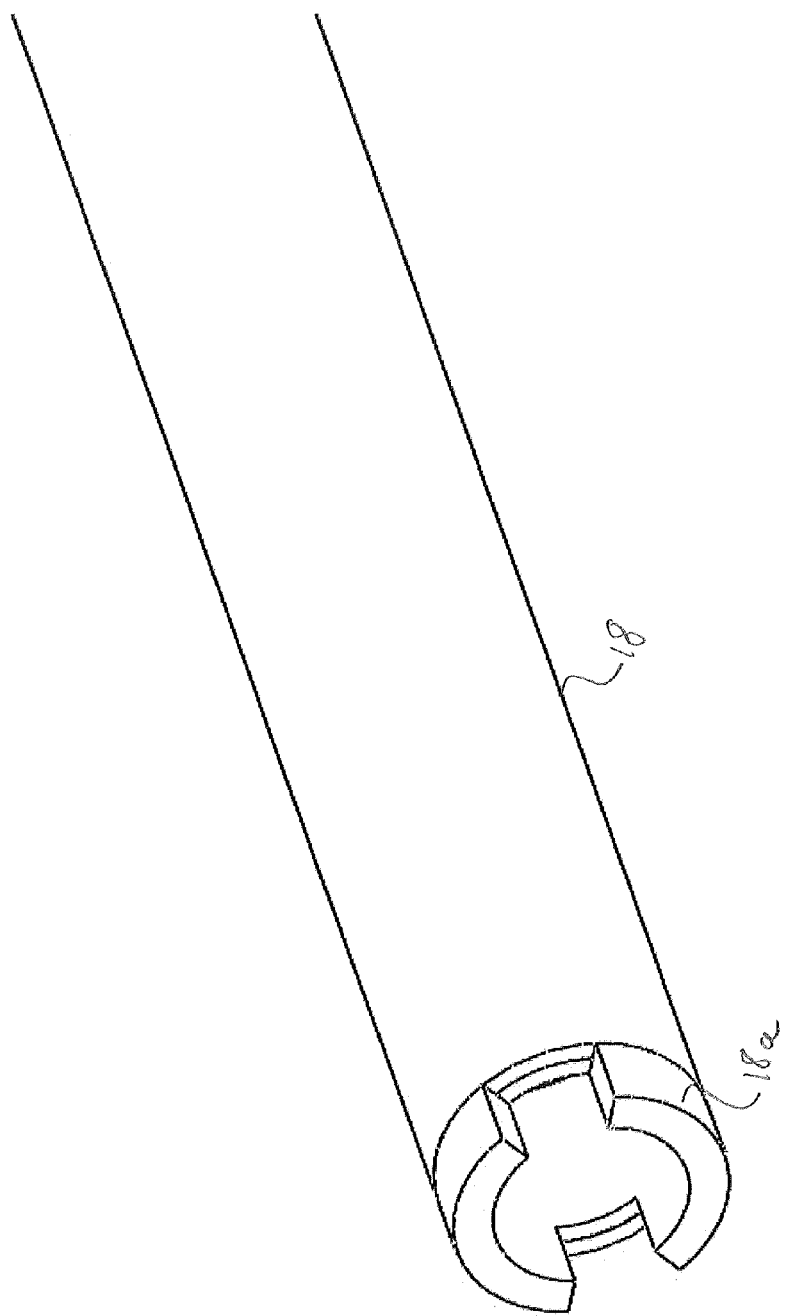
FIG. 13 is a first side lateral perspective view of the distal end of the cardiac lead drive portion of a device which engages the distal end of the lead, in accordance with one embodiment of the present invention.

FIG. 13 is a first side lateral perspective view of the distal end cardiac lead drive portion 18 of a device in accordance with one embodiment of the present invention. This view shows distal end 18A of the lead drive configured correspondingly to engage with a reciprocating end 20A of the cardiac lead.

Figure 14:
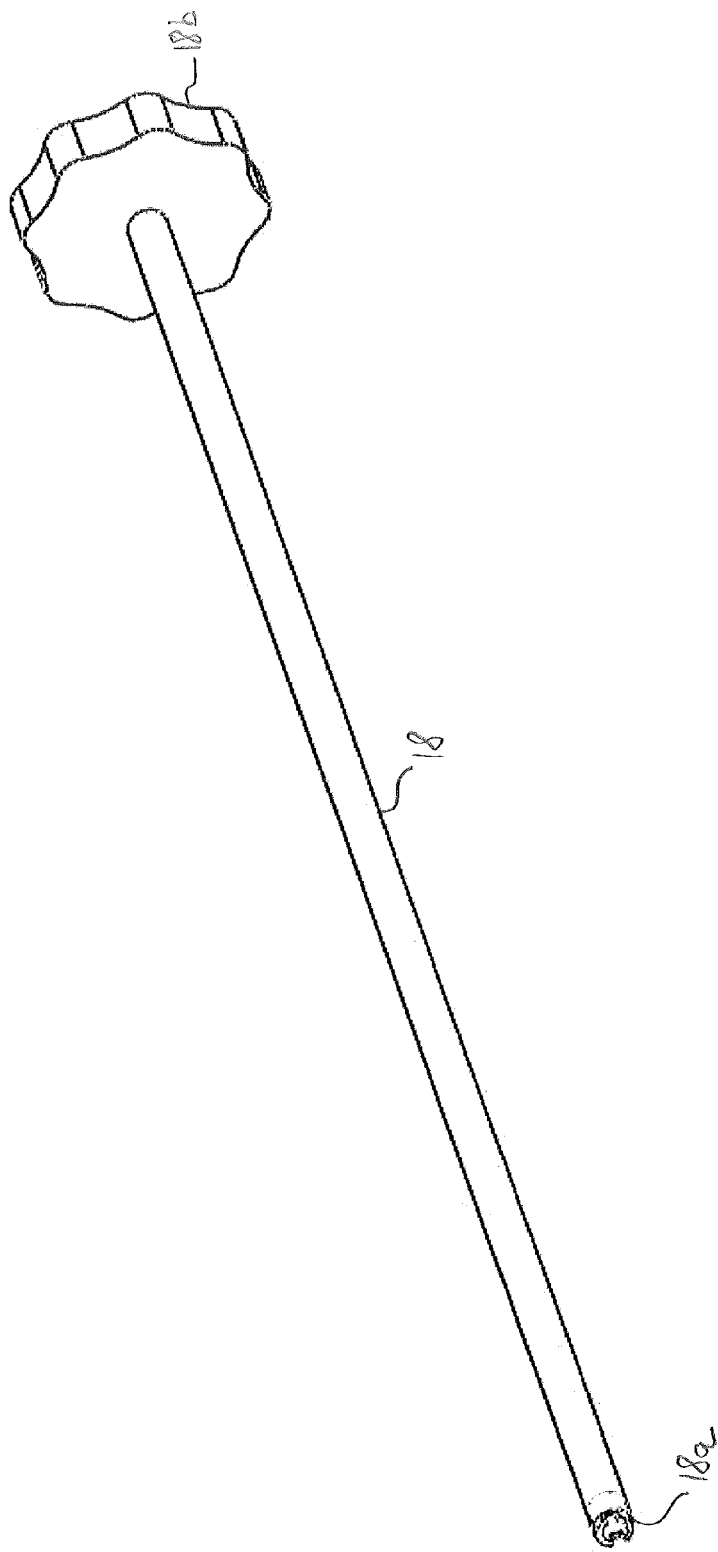
FIG. 14 is a first side lateral perspective view of the cardiac lead drive portion of a device, in accordance with one embodiment of the present invention.

FIG. 14 is a first side lateral perspective view of the cardiac lead drive portion 18 of a device, in accordance with one embodiment of the present invention.

At the very proximal end of inner tubular guide 6, there is a position lock 19 that in engaged position (see FIG. 10) holds the lead drive 18 with lead 20 such that the screw of the lead 20 is not protruding beyond the suction surface of the of inner suction foot portion 12. Once the inner suction foot portion 12 suction surface is in full contact with the heart muscle, the position lock 19 is disengaged to allow the lead drive 18 to implant the lead 20 to be implanted into heart muscle by screwing lead drive 18 to implant the lead 20 by use of lead drive wheel 18b. The lead drive 18 preferably is in the form of a hollow tube that houses the lead 20, and is made of solid, unyielding material except for about 7 cms of distal end which is compliant allowing it to be positioned by the inner tubular lead conduit or guide 6, by allowing it to conform to its articulation. The length of the lead drive 18 is such that, in loaded position, with the position lock 19 in the inner tubular lead conduit or guide 6 engaged, the screw end of the lead 20 is at the same plane as the co-terminally aligned suction foot surfaces 12 and 13 of the inner tubular lead conduit or guide 6 and outer tubular lead conduit or guide 7. The articulating and working lengths can vary.

The distal end of the lead drive 18 preferably has a special socket 18a into which the distal end 20A of the lead 20 fits in order to prevent displacement. The proximal end has a wheel 18b which allows the operator to screw in the lead into the heart muscle when the position lock 19 is disengaged. The length of the lead 20 preferably is in the range of about 52-58 cms (or length of current leads in the commercial market), and the proximal end of the lead 20 protrudes beyond the proximal end of the lead drive 18.

Figure 18:
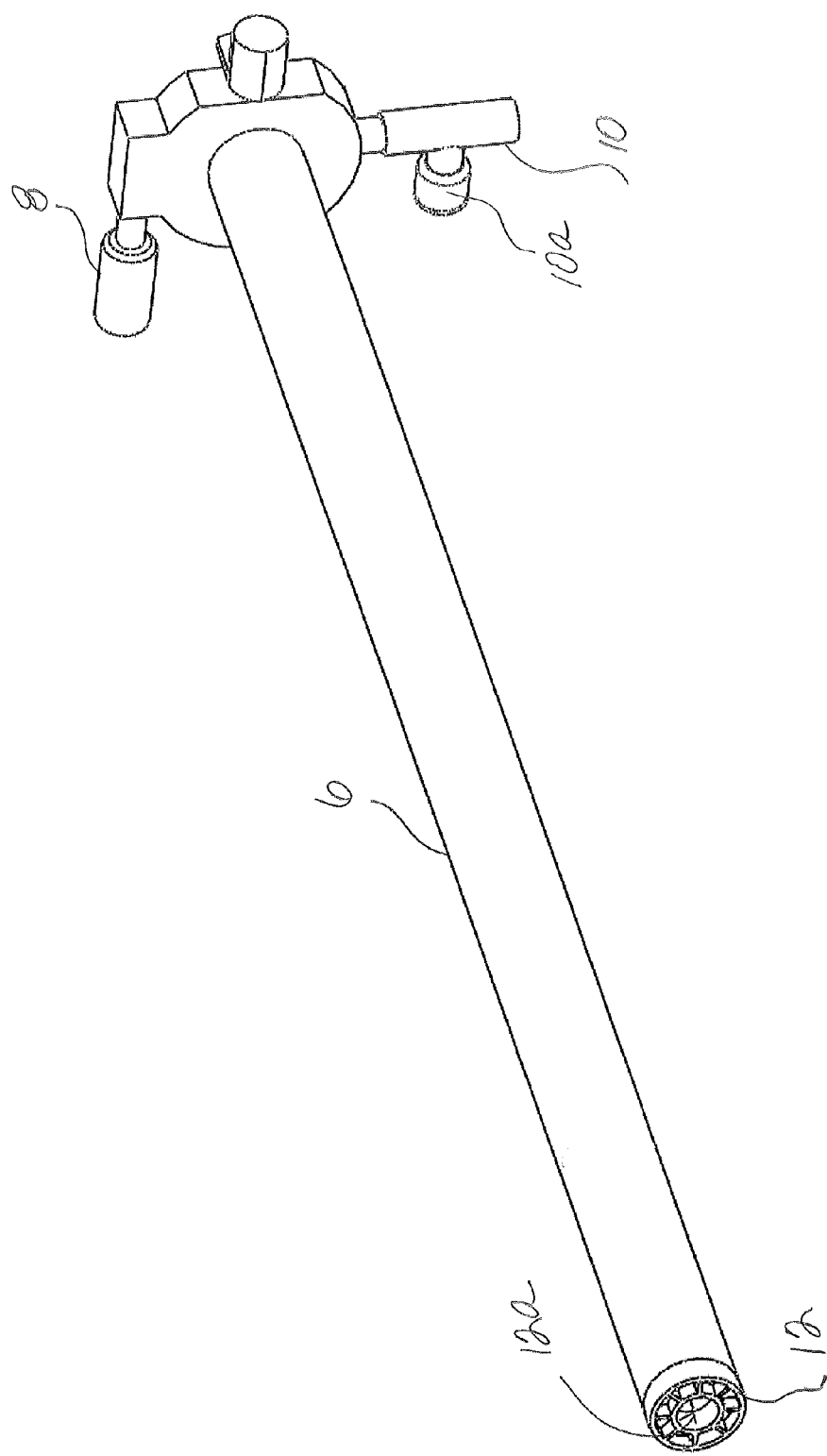
FIG. 18 is a partial first side lateral perspective view of the inner tubular lead guide with inner vacuum foot and associated actuator with the electrocautery part in place, in a device in accordance with one embodiment of the present invention.

FIG. 18 is a partial first side lateral perspective view of the inner tubular lead conduit or guide 6 with inner vacuum foot 12 and associated actuator knob 8.

Figure 19:
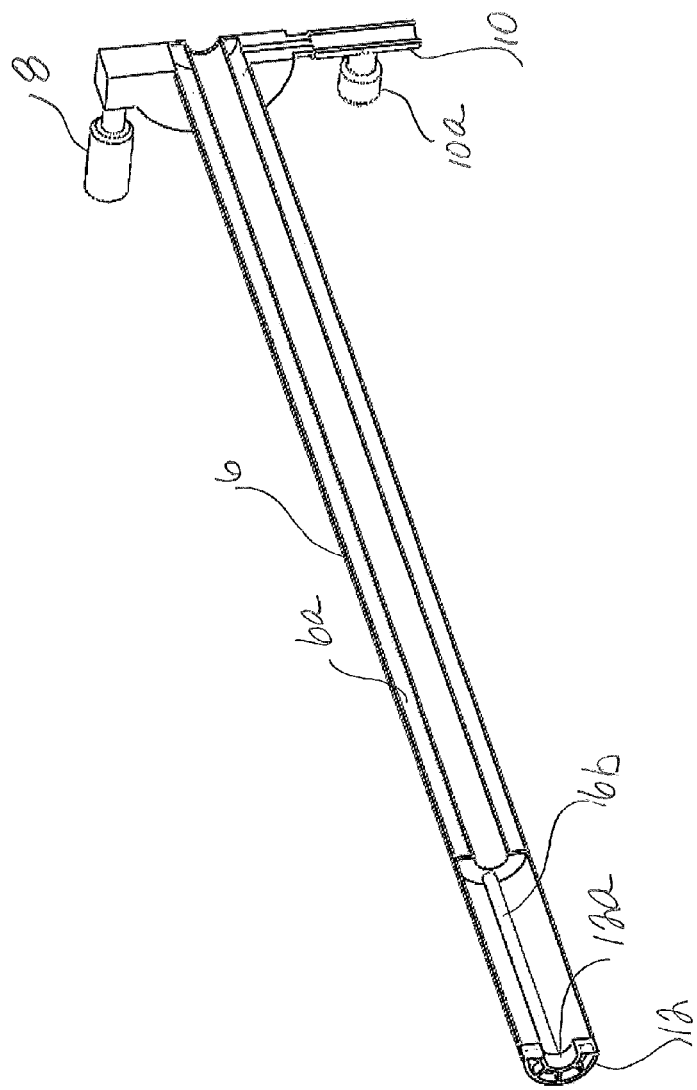
FIG. 19 is a partial first side cross-sectional lateral perspective view of the inner tubular lead conduit or guide with inner vacuum foot and associated actuator, of a device in accordance with one embodiment of the present invention.

FIG. 19 is a partial first side longitudinally cross-sectional lateral perspective view of the inner tubular lead conduit or guide 6 with inner vacuum foot 12 and associated actuator knob 8 controlling the articulation of the inner tubular lead conduit or guide 7. This view also shows the use of an internal vacuum chamber 6a that extends through the rigid portion of the inner tubular lead conduit or guide 6 up to a point where it is made flexible to form flexible portion 6c, and where there is provided a flexible tube or tubular portion 6b that communicates the vacuum to the inner vacuum foot 12 while allowing flexion/articulation of the distal end of the inner tubular lead conduit or guide 6, in accordance with a preferred embodiment of the present invention. These views show the aperture 12a through which the lead drive 18 and lead 20 may be passed during the operation of the device.

Figure 20:
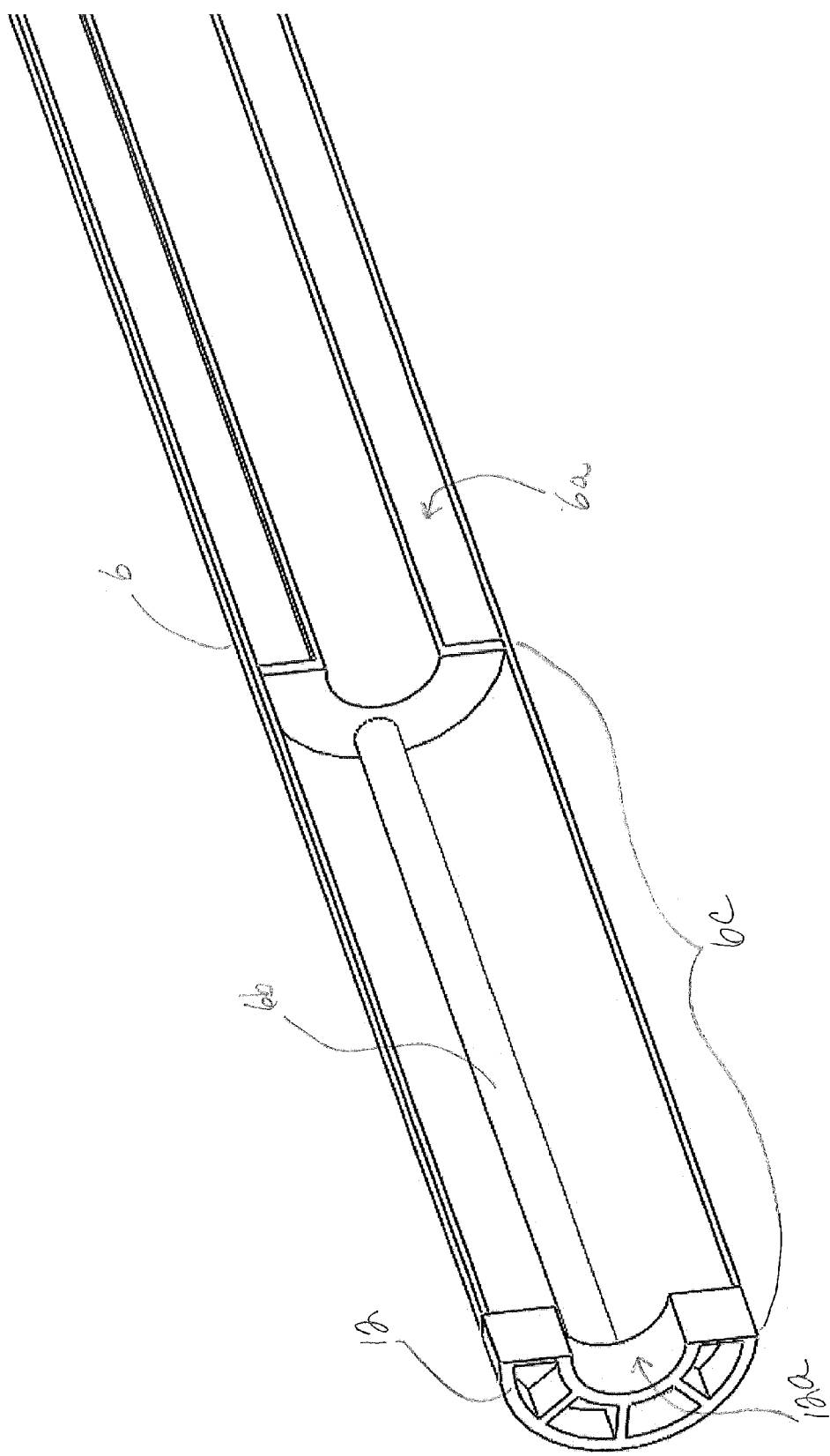
FIG. 20 is a detailed distal end partial first side cross-sectional lateral perspective view of the inner tubular lead conduit or guide with inner vacuum foot of a device in accordance with one embodiment of the present invention.

FIG. 20 is a partial first side longitudinally cross-sectional lateral perspective view of the inner tubular lead conduit or guide 6 with inner vacuum foot 12 showing the distal end in greater detail, and showing internal vacuum chamber 6a that extends through the rigid portion of the inner tubular lead conduit or guide 6 up to a point where it is made flexible to form flexible portion 6c, and flexible tube or tubular portion 6b that communicates the vacuum to the inner vacuum foot 12 while allowing flexion/articulation of the distal end of the inner tubular lead conduit or guide 6.

Figure 21:
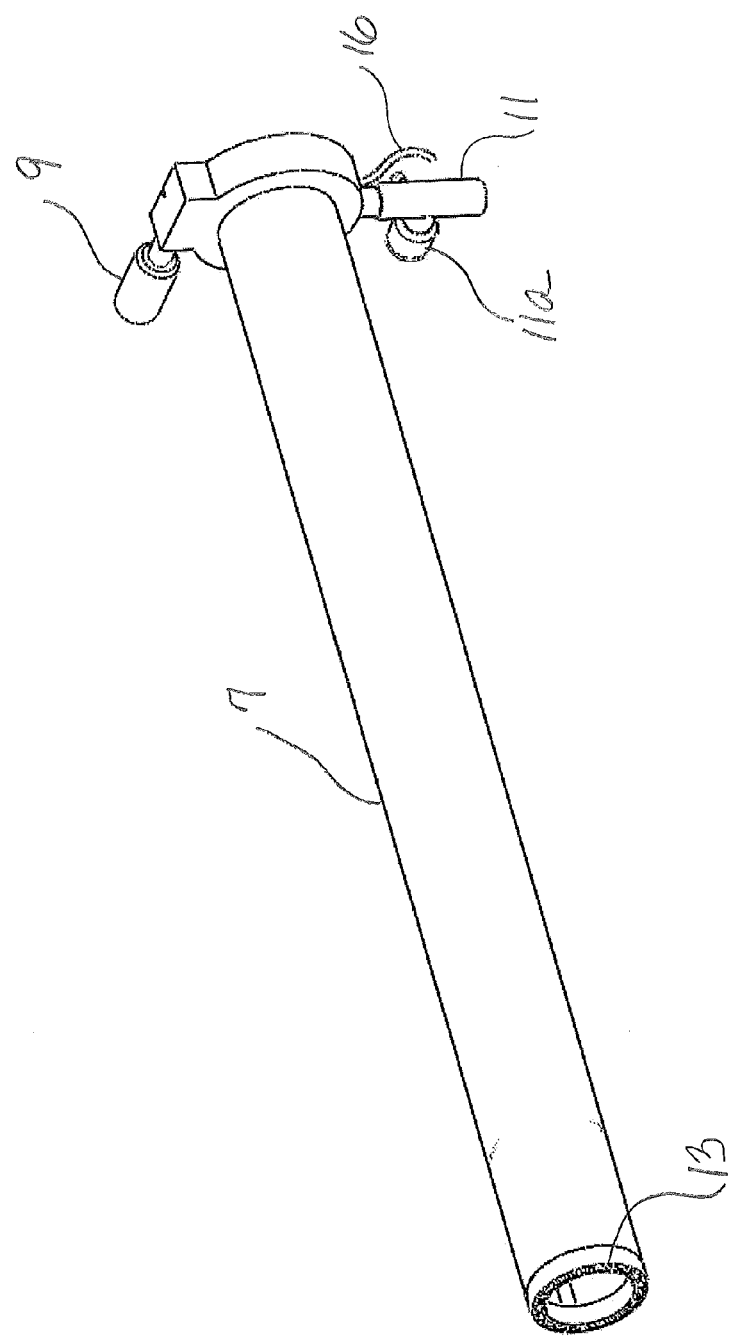
FIG. 21 is a detailed proximal end partial first side cross-sectional lateral perspective view of the outer tubular lead conduit or guide with outer vacuum foot and associated actuator, of a device in accordance with one embodiment of the present invention.

FIG. 21 is a first perspective lateral view of the outer tubular lead conduit or guide 7 of a device in accordance with one embodiment of the present invention, and showing outer vacuum foot 13.

Figure 22:
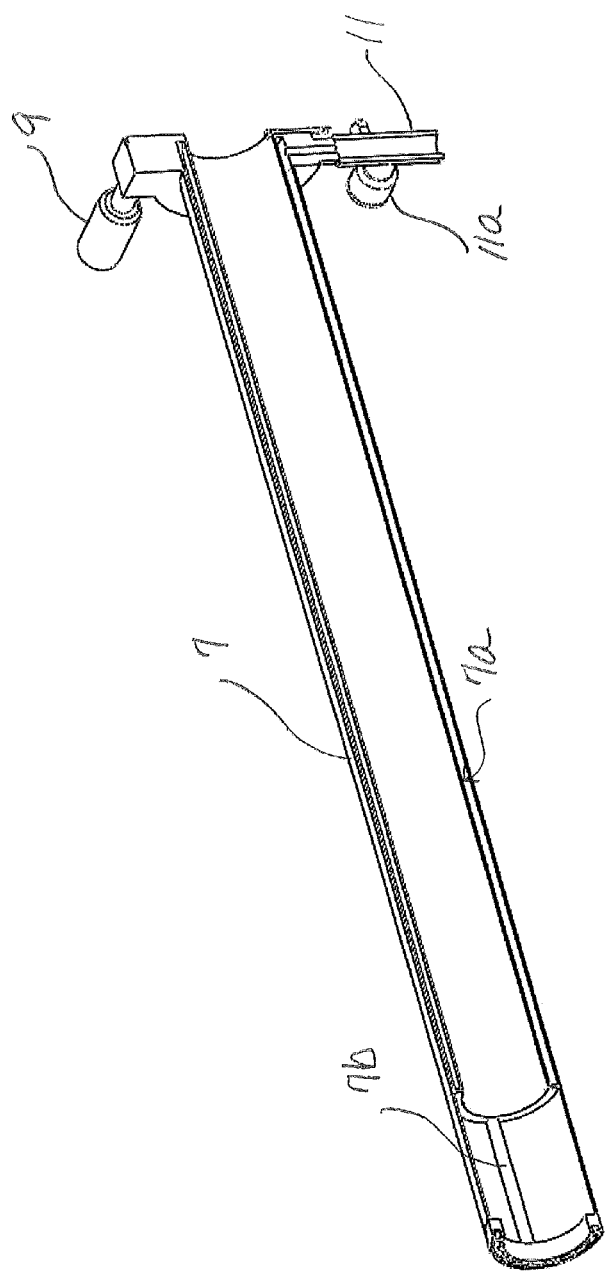
FIG. 22 is a partial first side longitudinally cross-sectional lateral perspective view of the outer tubular lead conduit or guide with outer vacuum foot of a device in accordance with one embodiment of the present invention.

FIG. 22 is a partial first side longitudinally cross-sectional lateral perspective view of the outer tubular lead conduit or guide 7 with outer vacuum foot 13 showing the proximal end in greater detail.

Figure 23:
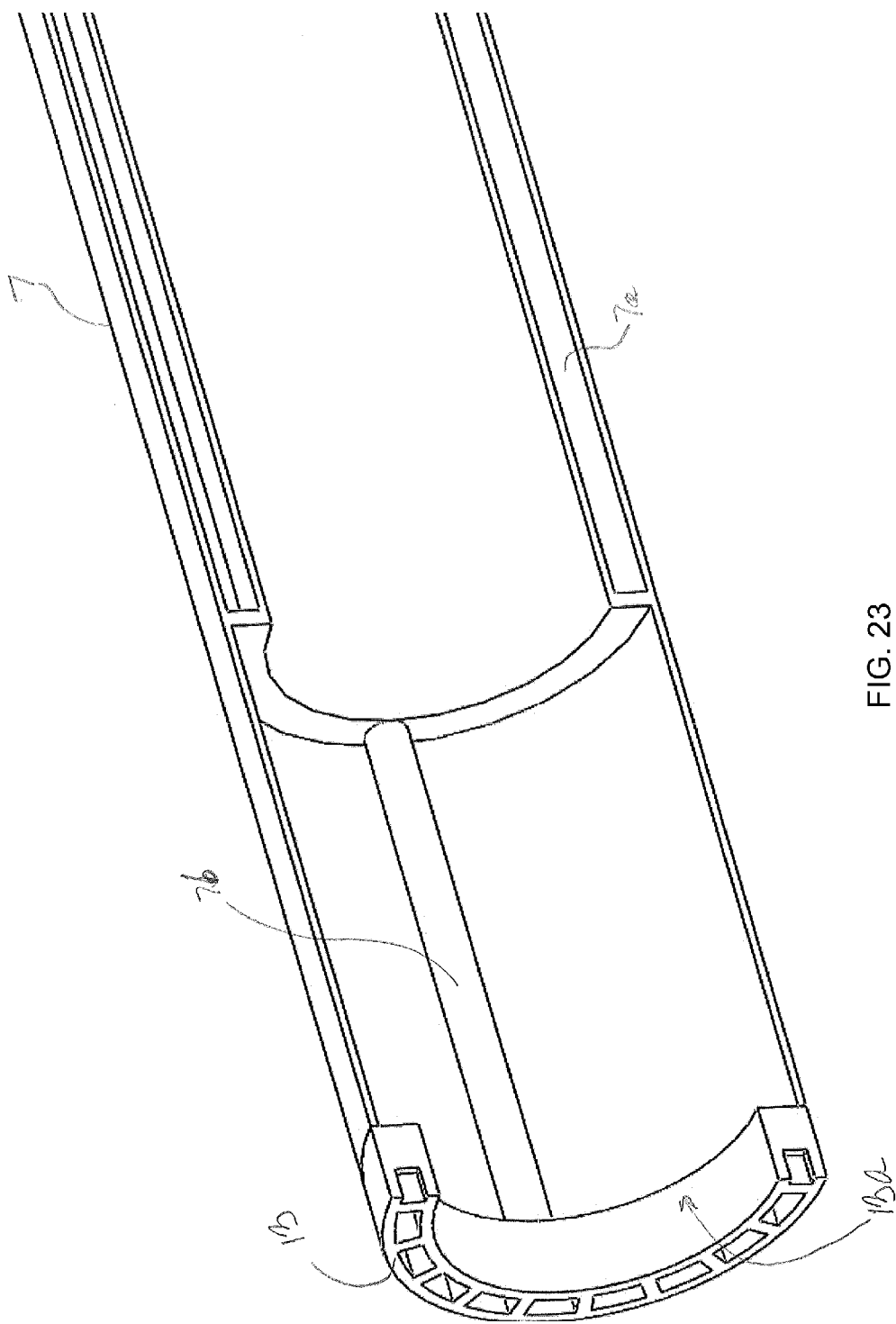
FIG. 23 is a first longitudinally cross-sectioned perspective lateral view of the distal portion of the outer tubular lead conduit or guide of a device in accordance with one embodiment of the present invention.

FIG. 23 is a partial first side longitudinally cross-sectional lateral perspective view of the outer tubular lead conduit or guide 7 with outer vacuum foot 13 showing the distal end in greater detail, and showing internal vacuum chamber 7a that extends through the rigid portion of the outer tubular lead conduit or guide 7 up to a point where it is made flexible to form flexible portion 7c, and flexible tube or tubular portion 7b that communicates the vacuum to the outer vacuum foot 13 while allowing flexion/articulation of the distal end of the outer tubular lead conduit or guide 7. These views show the aperture 13a through which the inner tubular lead conduit or guide 6 may be passed during the operation of the device, to allow lead drive 18 and lead 20 to be inserted therethrough.

Figure 24:
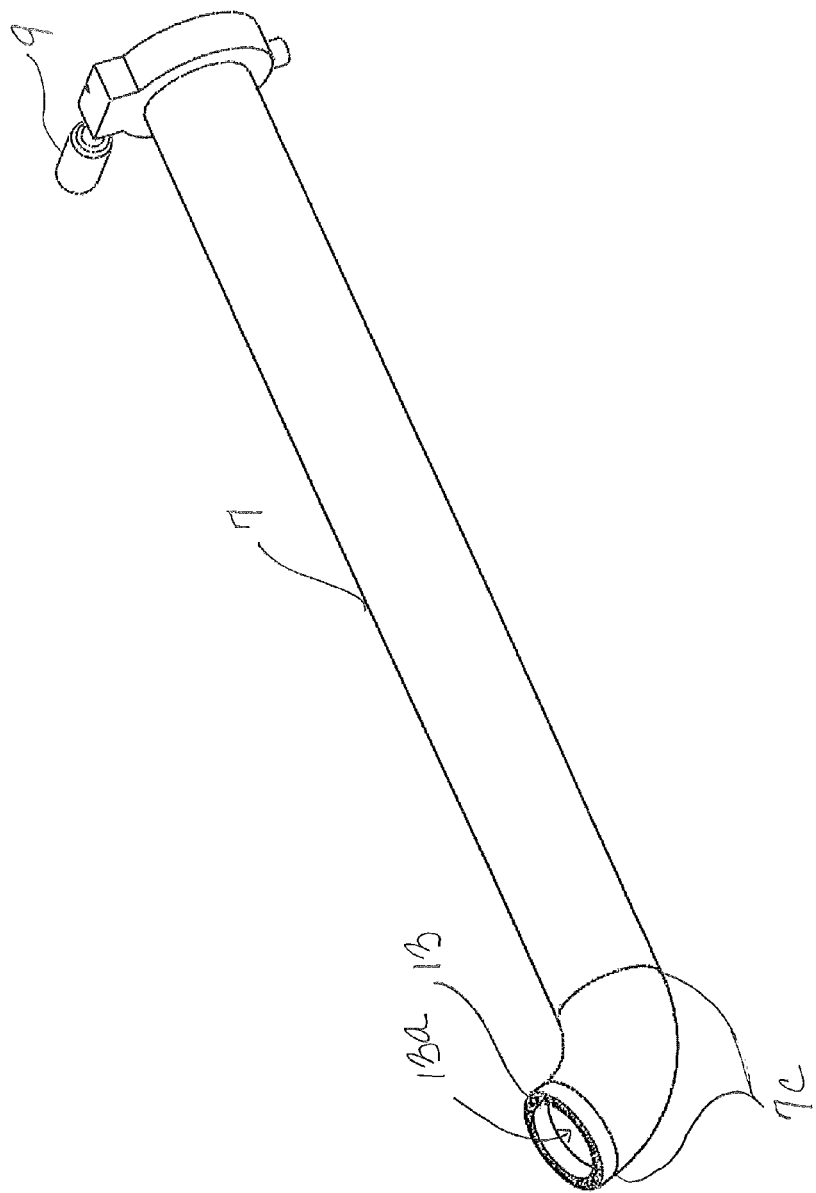
FIG. 24 is a first perspective lateral view of the outer tubular lead conduit or guide of a device shown in an articulated position, in accordance with one embodiment of the present invention.

FIG. 24 is a first perspective lateral view of the outer tubular lead conduit or guide 7 of a device shown in an articulated position, in accordance with one embodiment of the present invention.

Figure 25:
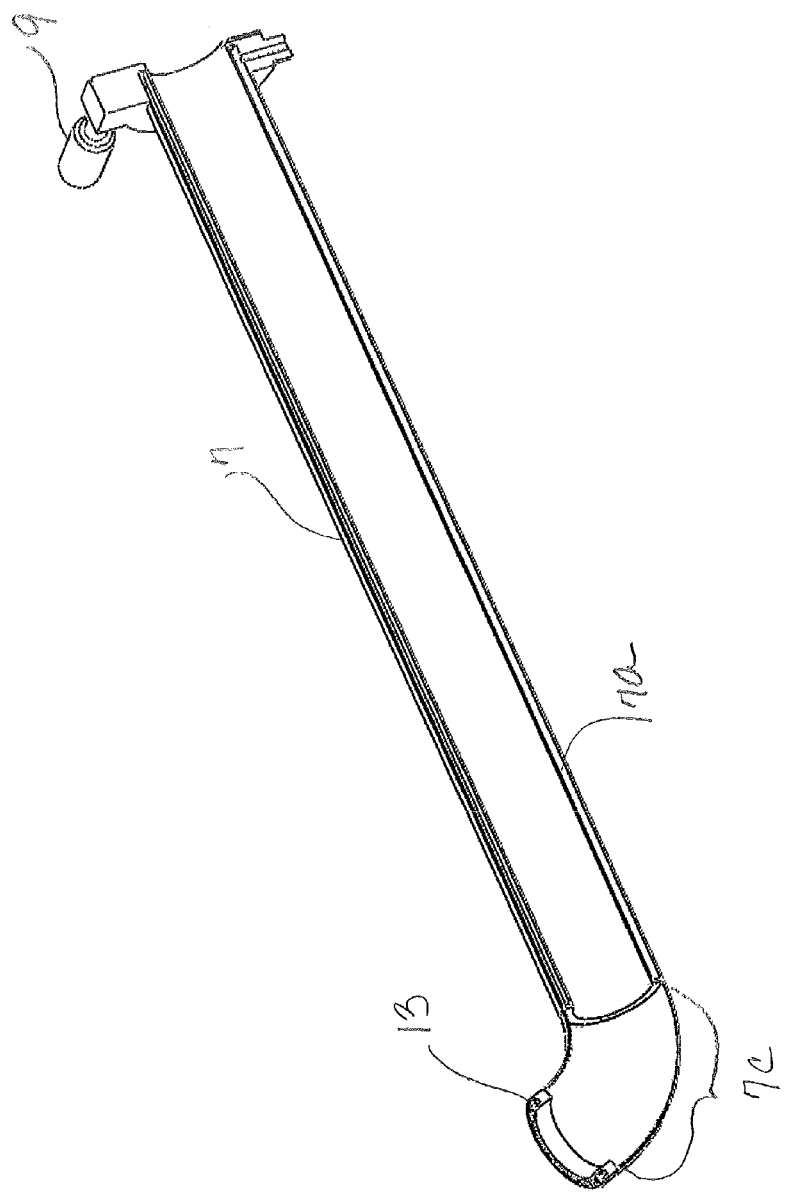
FIG. 25 is a first perspective lateral longitudinally cross-sectional view of the outer tubular lead conduit or guide of a device shown in an articulated position, in accordance with one embodiment of the present invention.

FIG. 25 is a first perspective lateral longitudinally cross-sectional view of the outer tubular lead conduit or guide 7 of a device shown in an articulated position, in accordance with one embodiment of the present invention. These views show outer tubular lead conduit or guide 7 articulated to deflect at a point where it is made flexible to form flexible portion 7c, so as to change the planar positioning of the outer vacuum foot 13.

Figure 26:
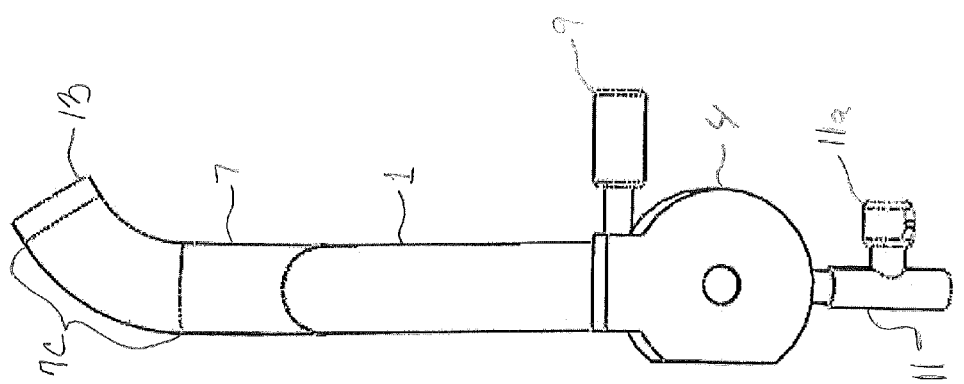
FIG. 26 is a bottom view of the cooperating inner and outer tubular lead conduits or guides in place in the elongated sheath body of a device in accordance with one embodiment of the present invention.

FIG. 26 is an upper perspective view of the cooperating-outer tubular lead conduit or guide 7 of a device as seen from the proximal end, in accordance with one embodiment of the present invention.

Figure 27:
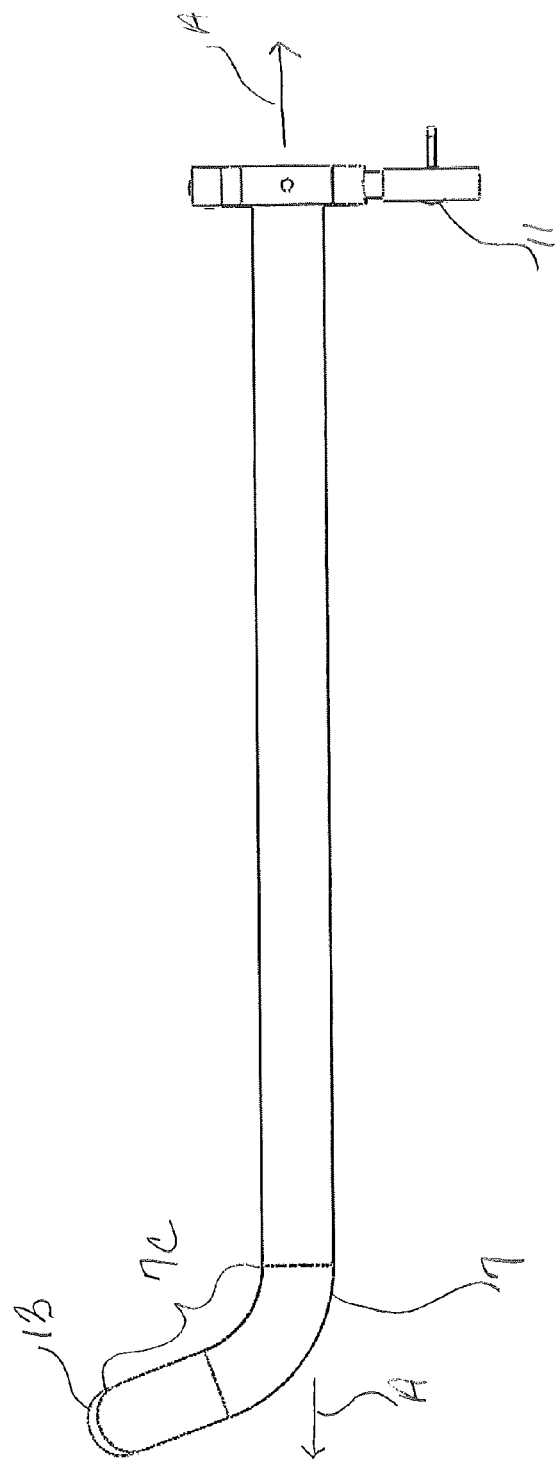
FIG. 27 is a lateral elevation view of the cooperating inner tubular lead conduit or guide and outer tubular lead conduit or guide of a device as seen from the proximal end, in accordance with one embodiment of the present invention.

FIG. 27 is a first lateral view of the cooperating outer tubular lead conduit or guide 7 of a device in accordance with one embodiment of the present invention shown in an articulated position. This view shows the articulation of flexible portion 7c so as to change the planar positioning of the outer vacuum foot 13.

Figure 27A:
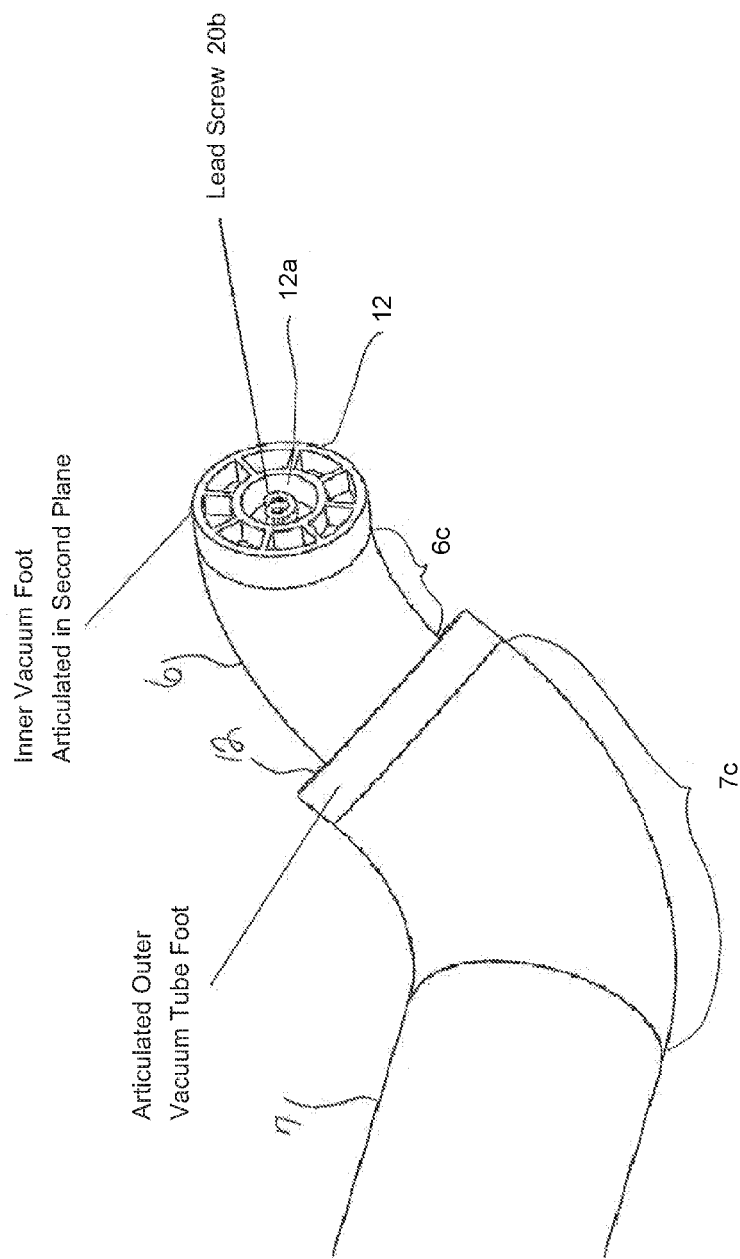
FIG. 27A is a perspective view of the cooperating outer tubular lead conduit or guide shown in an articulated position and the inner tubular lead conduit or guide articulated in a different angle, both in place in the elongated sheath body of a device in accordance with one embodiment of the present invention.

FIG. 27A is an additional perspective view of the cooperating inner tubular lead conduit or guide 6 shown in an articulated position with respect to and extending from outer tubular lead conduit or guide 7, in accordance with one embodiment of the present invention. This view shows the articulation of flexible portions 6c and 7c, so as to change the planar positioning of both the inner vacuum foot 12 and outer vacuum foot 13. This view shows the lead screw portion 20b in an unextended position within aperture 12a.

Figure 27B:
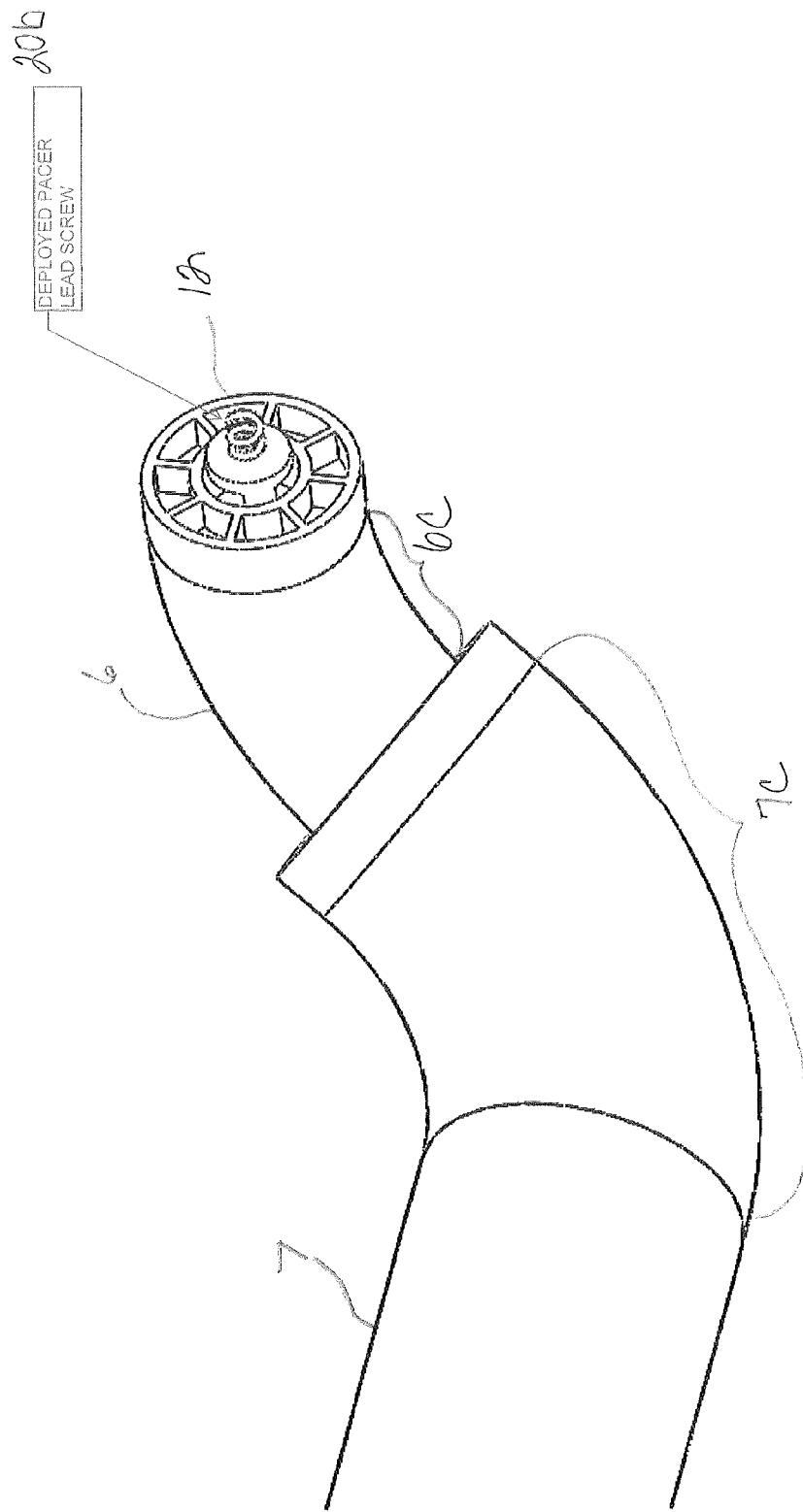
FIG. 27B is a perspective view of the cooperating outer tubular lead conduit or guide shown in an articulated position and the inner tubular lead conduit or guide articulated in a different angle, both in place in the elongated sheath body of a device in accordance with one embodiment of the present invention. This diagram also shows the lead with the lead drive engaged at the suction surface of the inner tubular lead conduit.

FIG. 27B is an additional perspective view of the cooperating inner tubular lead conduit or guide 6 shown in an articulated position with respect to and extending from outer tubular lead conduit or guide 7 in accordance with one embodiment of the present invention. This view shows the articulation of flexible portions 6c and 7c, so as to change the planar positioning of both the inner vacuum foot 12 and outer vacuum foot 13. This view shows the lead screw portion 20b in a deployed position extending from aperture 12a.

Figure 28:
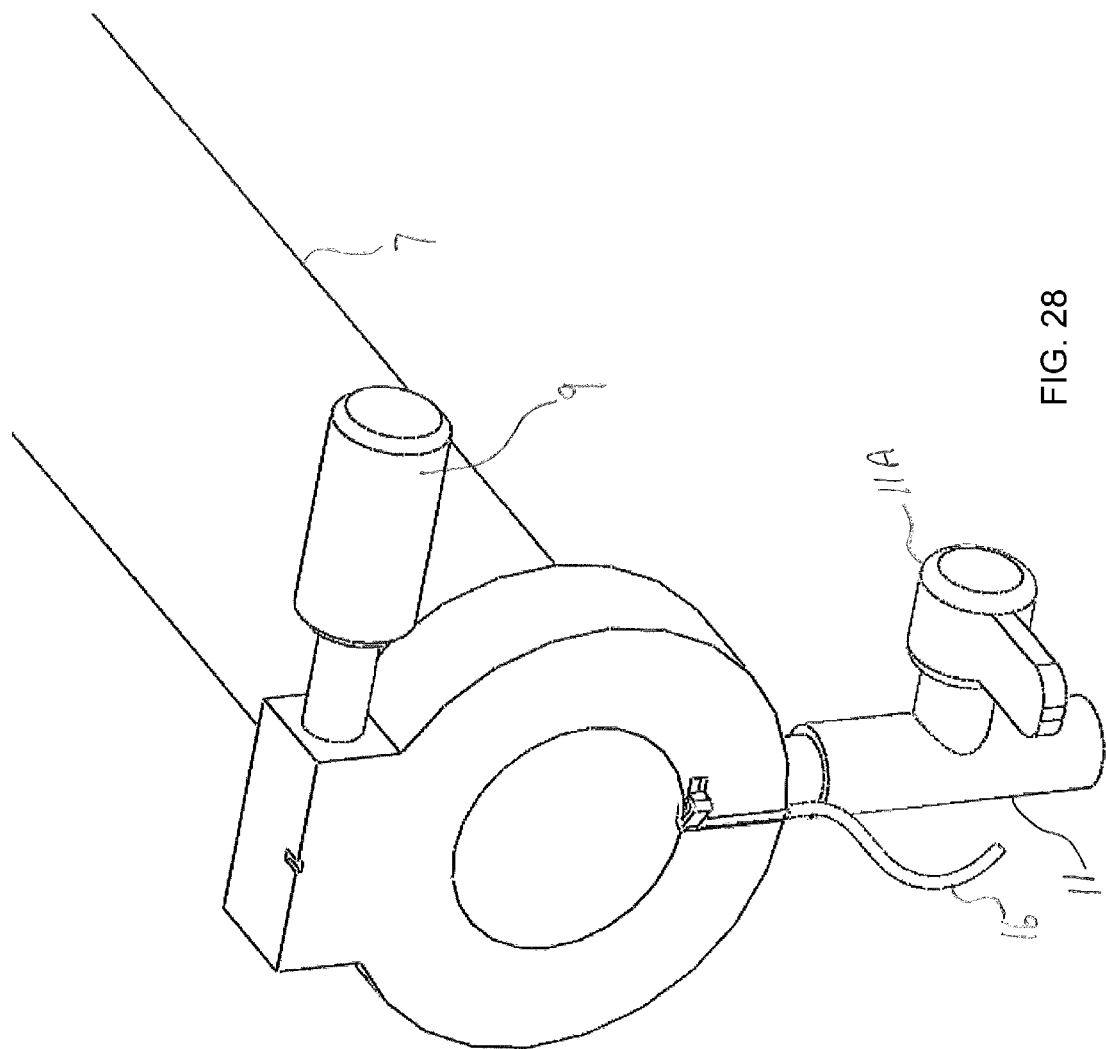
FIG. 28 is a proximal end perspective view of the outer tubular lead conduit or guide of a device in accordance with one embodiment of the present invention. This also shows the electrical connection and switch that will energize the electrocautery blade once in its engaged position.

FIG. 28 is a proximal end perspective view of the outer tubular lead conduit or guide 7 of a device in accordance with one embodiment of the present invention. This view shows the external electrical wire 16 connecting to a "spring biased contact" at the proximal end of the outer tubular lead conduit or guide 7, showing the stopcock 11A for the suction tube 11.

Figure 28A:
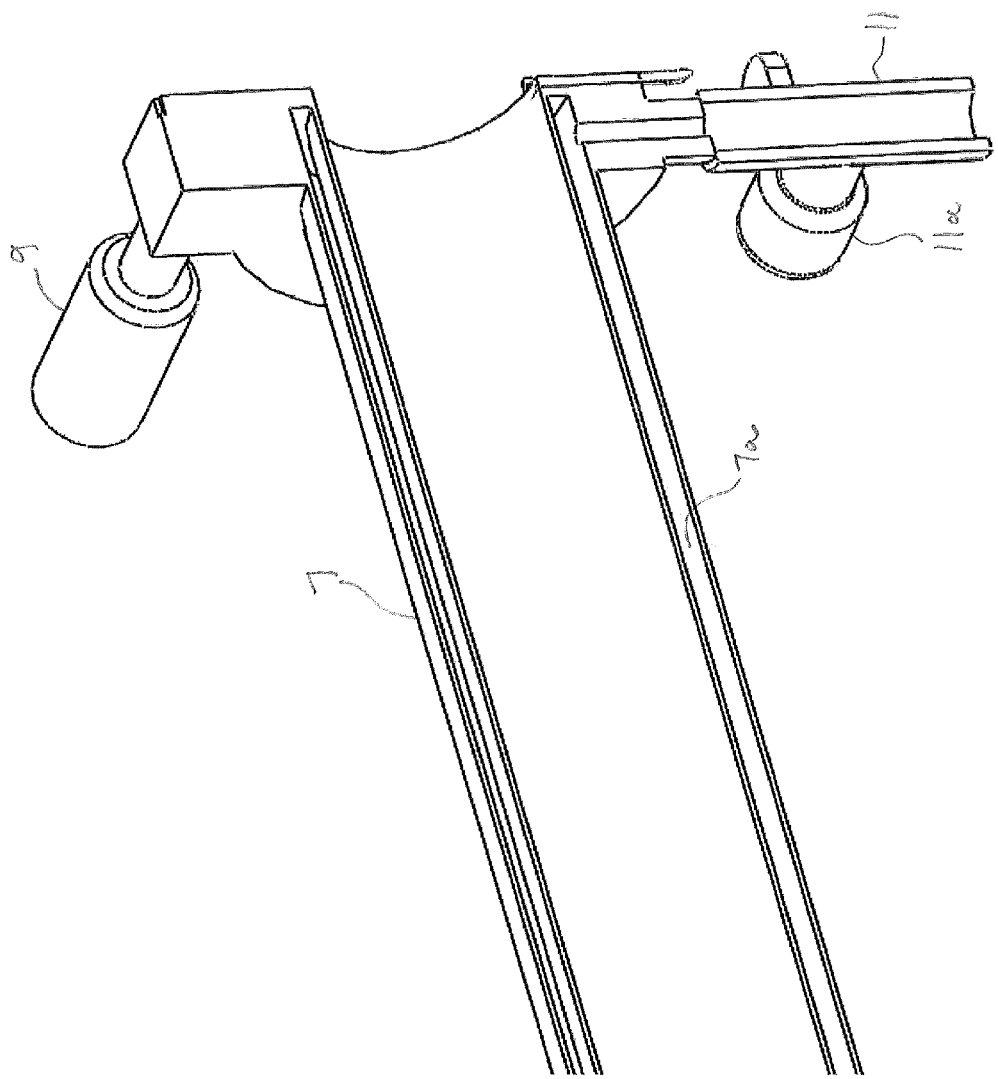
FIG. 28A is a proximal lateral perspective longitudinally cross-sectioned view of the outer tubular lead conduit or guide of a device in accordance with one embodiment of the present invention.

FIG. 28A is a proximal lateral perspective longitudinally cross-sectioned view of the outer tubular lead conduit or guide 7 of a device in accordance with one embodiment of the present invention showing internal vacuum chamber 7a that extends through the rigid portion of the outer tubular lead conduit or guide 7.

Figure 29:
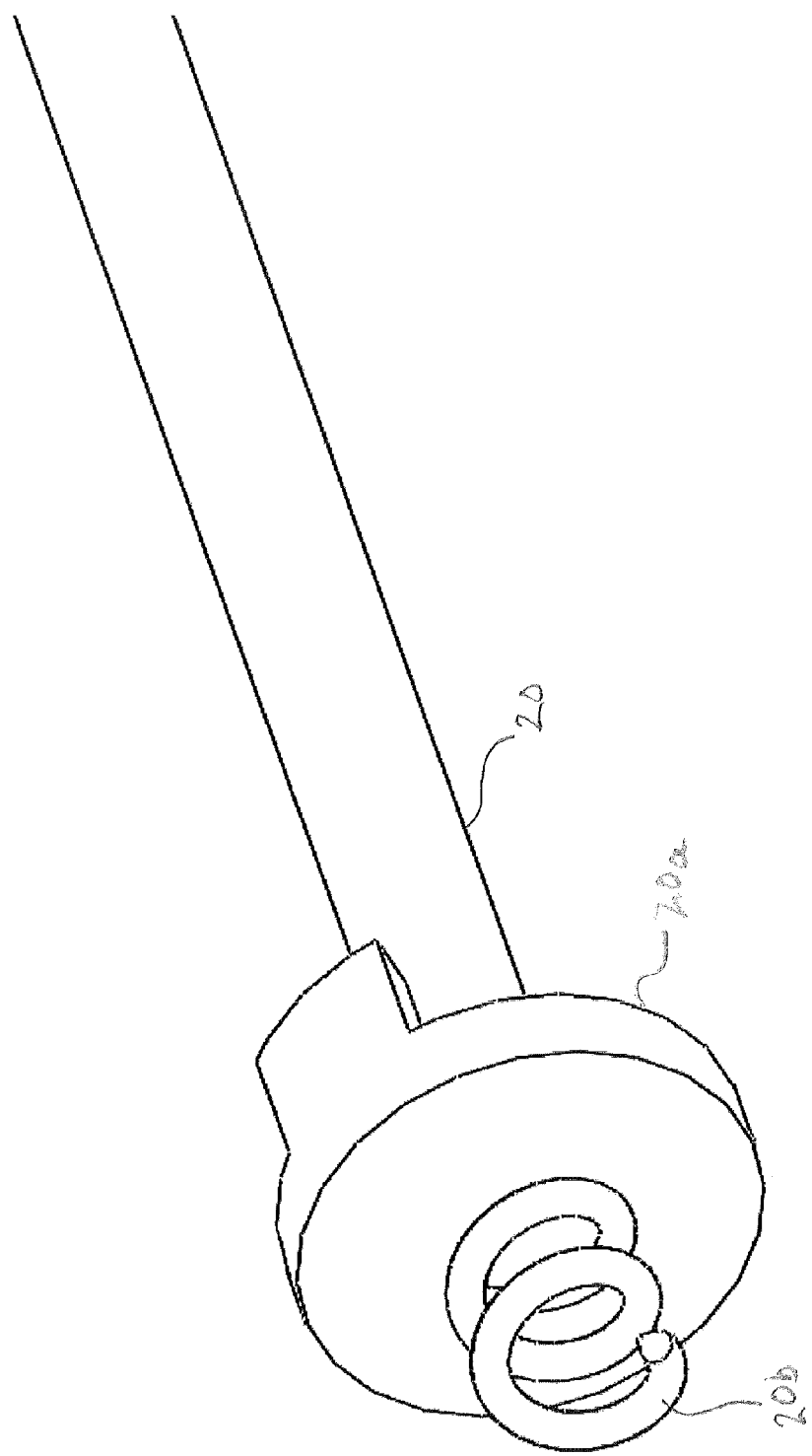
FIG. 29 is a proximal end perspective view of the cardiac lead distal end with associated head portion, the end that engages with the heart muscle in accordance with one embodiment of the present invention.

FIG. 29 is a proximal end perspective view of the cardiac lead 20 extending from lead head portion 20a of a device in accordance with one embodiment of the present invention. This view shows the lead 20 and the shaped lead head portion 20a that is adapted to cooperate with special socket 18a of the lead drive 18, into which the shaped lead head portion 20a of the lead 20 fits to secure its position and allow the lead drive 18 to screw the lead into place through action of corkscrew (or other fixable shape) lead end 20b; i.e., the pacing or conducting end.

Figure 30:
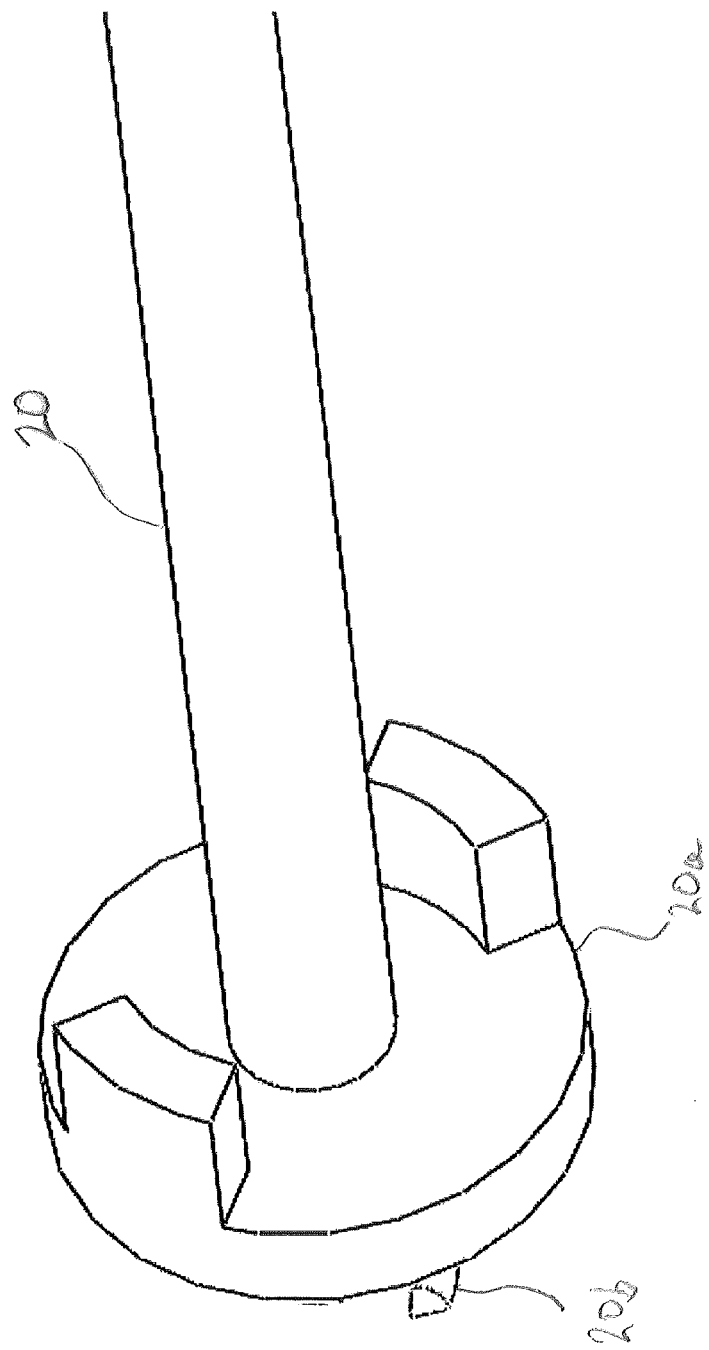
FIG. 30 is a distal end perspective view of the cardiac lead distal end with associated head portion, the end that engages with the heart muscle in accordance with one embodiment of the present invention.

FIG. 30 is a distal end perspective view of the cardiac lead 20 extending from lead head portion 20a, as shown in FIG. 29, and in which like reference numerals refer to corresponding portions thereof.

As to the procedure for using the device of the present invention and otherwise to practice its method, the following steps may be used:

An access incision is first made in the left chest wall, with a 3 to 4 cm diameter maximum.

The left lung is then decompressed and collapsed, thereby exposing the pericardial sac, using the standard thoracoscopic, single lung ventilation technique.

As may be appreciated with reference to FIG. 1, the elongated sheath body 1 is inserted by passing its distal end through the chest wall via the access.

As may be appreciated with reference to FIG. 2, the distal ends of the coterminous inner and outer vacuum lead conduits or guides 6 and 7 (i.e., presenting inner and outer vacuum suction feet 12 and 13) and are urged through the elongated sheath body 1, opening the spring biased cover 3 of the introducing distal end of the sheath.

As may be appreciated with reference to FIGS. 3 and 4, the faces of the inner and outer vacuum suction feet 12 and 13 are placed on the pericardium by articulating with knob 9 with or without rotating along its long axis. Once in place, the set screw 5 is tightened against the outer vacuum lead conduit or guide 7. At this point, the elongated sheath body 1 may be rotated by the operator about its longitudinal axis A for fine positioning. The vacuum for inner and outer vacuum lead conduits or guides 6 and 7 is controlled via respective stopcocks 10a and 11a to govern vacuum to inner and outer vacuum suction feet 12 and 13 respectively. Using the handle 4 of the elongated sheath body 1, the operator may place slight traction to pull the yielding pericardium away from the subjacent myocardium or heart muscle.

As may be appreciated with reference to FIG. 7, electrocautery knob or wheel 15c is then urged to position 2.

As may be appreciated with reference to FIGS. 4, 5 and 3A, electrocautery knob or wheel 15c is then rotated 360 degrees or more (making reference to the degree indicator thereupon, thereby cutting the pericardium, which is then held captive between outer and inner suction ring by vacuum action from inner vacuum suction foot 12, the cut piece of pericardium held by inner vacuum foot 12 secured for removal.

As may be appreciated with reference to FIG. 6, the electrocautery knob or wheel 15c may then be returned to position 1. As may be appreciated with reference to FIG. 8, the inner vacuum lead conduit or guide 6 is then removed from outer vacuum lead conduit or guide 7 (with the held piece of cut pericardial tissue). The vacuum to inner vacuum lead conduit or guide 6 is turned off and the cut pericardial tissue is removed from inner vacuum suction foot 12. Spacer 17 is also taken out from around inner vacuum lead conduit or guide 6.

Referring to FIGS. 9 and 10, the lead 20 and lead drive 18 assembly is inserted into inner vacuum lead conduit or guide 6 until drive assembly contacts position lock 19.

As may be appreciated from FIG. 11, the inner vacuum lead conduit or guide 6 is reintroduced into the outer vacuum lead conduit or guide 7/electrocautery assembly 15, during which time, the outer vacuum suction foot 13 is still attached to the pericardium with suction, keeping it taut and splayed with a central hole, and through which the inner vacuum lead conduit or guide 6 with its inner vacuum suction foot 12 may be further advanced, the spacer 17 having been removed.

As may be appreciated from FIG. 11, this Figure shows the Position inner vacuum suction foot 12 as it would be advanced against the left ventricular wall through the pericardial hole created in the procedure.

As may be appreciated with reference to FIG. 4, the second plane of articulation is made possible by rotating articulation knob 8. The operator may rotate inner vacuum lead conduit or guide 6 along its long axis for fine positioning. At this point, the vacuum for inner vacuum lead conduit or guide 6 may be engaged to attach itself to the myocardium or heart muscle; and the loaded lead drive 18 (with lead 20) is positioned inside the inner vacuum lead conduit or guide 6 in such a way that it is in touch with the myocardium with the distal end of the pacer lead screw at the end of the lead 20. At this point, the lead 20 may be tested for sensing and pacing parameters by seeking various attachment points and testing the lead 20, prior to final placement of the lead 20 in the heart tissue.

Referring to FIGS. 10A and 10B, the position lock 19 may be disengaged from the lead drive 18, to allow special socket 18a, into which the distal end of the lead 20 (i.e. cooperatively shaped lead head 20a) fits, to permit the lead 20 to be advanced and attached to the heart wall. This attachment is effected by rotating the lead 20 (by use of lead drive wheel 18b) clockwise while applying slight axial force along axis A. This may be further appreciated from reference to FIGS. 10C and 27B. At this point, the lead 20 again may be tested for sensing and pacing parameters.

As shown in FIG. 9A, the lead drive 18 may be removed from within inner vacuum lead conduit or guide 6, after which the vacuum serving inner vacuum suction foot 12 may be turned off in order to effect its release from the tissue site.

A summary of the preferred procedure is presented in table form in Appendix A hereto.

From this point, the balance of the surgical operation and energizes of the pacing lead made be completed in accordance with methods and apparatus known and used in the art.

It will be appreciated that the mechanical arrangements in the device and the logical order of the steps in the described methods are used for purposes of illustration only, and that the steps may be varied where not otherwise inconsistent with the purpose and result obtained in the practice of the invention.

The invention may be embodied in other specific forms without departing from the spirit or essential characteristics thereof. The foregoing embodiments are therefore to be considered in all respects illustrative rather than limiting on the invention described herein. The scope of the invention is thus indicated by the appended claims rather than by the foregoing description, and all changes that come within the meaning and range of equivalency of the claims are intended to be embraced therein.

The present invention may be used in accordance with other methods and devices relating to lead and conduit placement, such as those described in the following references that are hereby incorporated herein by reference:

REFERENCES

| Patent or Patent Application Number |
| --- |
| U.S. 2004/0153098 |
| U.S. Pat. No. 7,526,342 |
| U.S. 2003/0187461 |
| U.S. 2010/0312256 |
| U.S. Pat. No. 7,544,197 |
| U.S. Pat. No. 7,890,192 |
| U.S. Pat. No. 7,930,040 |
| U.S. 2005/0004644 |
| U.S. Pat. No. 6,132,456 |
| U.S. Pat. No. 5,902,331 |
| U.S. 2004/0215139 |
| U.S. Pat. No. 6,868,291 |
| U.S. Pat. No. 5,882,333 |
| U.S. Pat. No. 5,203,772 |
| U.S. Pat. No. 6,697,677 |
| U.S. 2006/0009827 |
| U.S. 2009/0182347 |
| U.S. 2009/0198251 |
| WO 2008058265 |
| WO 2004058326 |
| WO 9906104 |
| EP 452278 |
| U.S. Pat. No. 5,139,033 |
| U.S. Pat. No. 4,146,037 |
| U.S. Pat. No. 4,972,847 |
| U.S. Pat. No. 5,342,413 |
| U.S. Pat. No. 7,270,669 |
| U.S. 2006/0161238 |
| U.S. Pat. No. 4,271,846 |
| U.S. Pat. No. 5,972,013 |
| U.S. 2003/0187461 |
| U.S. 2010/0312256 |
| U.S. Pat. No. 7,544,197 |
| U.S. Pat. No. 7,890,192 |
| U.S. Pat. No. 7,930,040 |
| U.S. 2005/0004644 |
| U.S. Pat. No. 6,132,456 |
| U.S. Pat. No. 5,902,331 |
| U.S. 2004/0215139 |
| U.S. Pat. No. 6,868,291 |
| U.S. Pat. No. 5,882,333 |
| U.S. Pat. No. 5,203,772 |
| U.S. Pat. No. 6,697,677 |
| U.S. 2006/0009827 |
| U.S. 2009/0182347 |
| U.S. 2009/0198251 |
| WO 2008058265 |
| WO 2004058326 |
| WO 9906104 |
| EP 452278 |
| U.S. Pat. No. 5,139,033 |
| U.S. Pat. No. 4,146,037 |
| U.S. Pat. No. 4,972,847 |
| U.S. Pat. No. 5,342,413 |
| U.S. Pat. No. 7,270,669 |
| U.S. 2006/0161238 |
| U.S. Pat. No. 4,271,846 |

Appendix A

PLAD Procedure
1. Make access in left chest wall
    a. Circular or oblong
        1. 3 cm dia. maximum
        2. 3 cm×4 cm maximum
2. Decompress/collapse left lung thereby exposing pericardial sac (Standard thoracoscopic, single lung ventilation technique)
3. Pass distal end of sheath through chest wall via access
4. Push distal end of outer and inner vacuum tubes through sheath, opening the spring biased cover of the introducing sheath
5. Position faces of outer and inner vacuum feet on pericardium by rotating articulation knob A
    a. Tighten set screw for outer vacuum tube
    b. May rotate sheath around its long axis for fine positioning
6. Turn on vacuum for outer and inner vacuum tubes via stop cocks on outer and inner heads respectively
7. Using handle of sheath, place slight traction to pull the yielding pericardium away from the subjacent myocardium or heart muscle
8. Push Electrocautery knob to position 2
9. Rotate Electrocautery knob >360 degrees thereby cutting pericardium held captive between outer and inner suction ring
    a. Cut piece of pericardium held by inner vacuum foot
10. Pull Electrocautery knob back to position 1
11. Remove inner vacuum tube (with the held piece of cut pericardial tissue) and spacer A
12. Turn off vacuum to inner vacuum tube
13. Remove cut pericardial tissue
14. Remove spacer A from inner vacuum tube
15. Load lead and drive assembly into inner tube until drive assembly contacts position lock
16. Reintroduce inner vacuum tube into outer vacuum tube/electrocautery assembly
    a. All this time, the outer vacuum foot is still attached to the pericardium with suction, keeping it taut and splayed with a central hole
17. Position inner vacuum foot against left ventricular wall through the pericardial hole created in Step 9
    a. Second plane of plane of articulation possible by rotating articulation knob B
        1. May rotate inner vacuum tube along its long axis for fine positioning
18. Turn on vacuum for inner vacuum tube
    a. Loaded Lead is positioned inside inner suction tube in such a way that it is in touch with myocardium with the distal end of the pacer lead screw
19. Test sensing and pacing parameters
20. Disengage position lock for drive
21. Attach lead to heart wall by rotating drive clockwise while applying slight axial force
22. Test sensing and pacing parameters
23. Withdraw lead drive
24. Turn off vacuum for inner vacuum tube
25. Remove inner vacuum tube in a direction axial to lead (to prevent dislodgement of lead) by simultaneously relaxing articulation and withdrawing inner vacuum tube from outer vacuum tube
26. Turn off vacuum for outer vacuum tube
27. Remove outer tube in a direction axial to lead (to prevent dislodgement of lead) by simultaneously relaxing articulation and withdrawing outer vacuum tube and sheath together from chest cavity
28. The proximal end of the lead can now be channeled and connected with the pacemaker/defibrillator device
29. Close access site

What is claimed is:

1. A device adapted for the thoracoscopic placement of a lead at a target site on an epicardial surface of a heart, the device comprising:
    (a) an inner tubular lead conduit having a flexible inner tubular lead conduit distal end comprising an inner suction foot portion, said inner tubular lead conduit adapted to conduct a vacuum to said inner suction foot portion;
    (b) a lead drive head having a flexible distal end and inserted within said inner tubular lead conduit so as to extend to said flexible inner tubular lead conduit distal end;
    (c) a lead extending through said lead drive head and having a lead distal end portion, said lead distal end portion extending from said distal end of said lead drive head for contact with the epicardial surface of the heart;
    (d) an outer tubular lead conduit having a flexible outer lead conduit distal end comprising an outer suction foot portion, said outer tubular lead conduit adapted to conduct a vacuum to said outer suction foot portion while being adapted to slidingly conduct said inner tubular lead conduit, so as to permit said inner tubular lead conduit to be extended from said outer lead conduit distal end;
    (e) an elongated sheath body having a longitudinal axis, a proximal end portion and a distal end portion, and having a proximal inlet and a distal lead outlet for extending said inner and outer lead conduits therethrough, said elongated sheath body comprising a lead receiving passageway for receiving and conducting said inner and outer tubular lead conduits between said proximal inlet and said distal lead outlet; said lead drive head adapted to releasably engage said lead distal end portion such that said engagement is releasable such that said lead drive head may be released from said lead distal end portion once said lead is attached to said epicardial surface of a heart;
    (f) a first actuator adapted to articulate said inner suction foot portion and said outer suction foot portion while said inner suction foot portion is disposed within said outer suction foot portion; and
    (g) a second actuator adapted to articulate said inner suction foot portion when said inner suction foot portion is extended from said outer suction foot portion.

2. The device of claim 1 wherein said elongated sheath body has a handle portion extending laterally therefrom.

3. The device of claim 1 wherein said first actuator comprises a knob adapted to articulate said inner suction foot portion and said outer suction foot portion while said inner suction foot portion is disposed within said outer suction foot portion.

4. The device of claim 1 wherein said second actuator comprises a knob adapted to articulate said inner suction foot portion when said inner suction foot portion is extended beyond said outer suction foot portion.

5. The device of claim 1 additionally comprising an electrocautery blade extending from between said inner and outer suction foot portions.

6. The device of claim 5 wherein electrocautery blade is adapted to be rotated 360 degrees and is energized by a spring biased switch in an extended position.

7. The device of claim 1 wherein said inner suction foot portion comprises a plurality of air channels, so as to be capable of providing suction to said inner suction foot portion.

8. The device of claim 1 wherein said outer suction foot portion comprises a plurality of air channels, so as to be capable of providing suction to said outer suction foot portion.

9. The device of claim 1 wherein said lead distal end is held by said lead drive head so as to extend from the distal end of said lead drive head.

10. The device of claim 1 wherein said first actuator comprises at least one tension cord attached to a knob portion disposed on said proximal end portion, said knob adapted to move said at least one tension cord within said elongated sheath body so as to articulate said inner suction foot portion and said outer suction foot portion.

11. The device of claim 1 wherein said second actuator comprises at least one tension cord attached to a knob portion disposed on said proximal end portion, said knob adapted to move said at least one tension cord within said elongated sheath body so as to articulate said inner suction foot portion when said inner suction foot portion is extended from said outer suction foot portion.

12. The device of claim 1, additionally comprising a source of vacuum suction in fluid communication with said inner suction foot portion, said source of vacuum suction selected from the group consisting of a hand pump, or a syringe attached to said elongated sheath body, or a motorized pump supplying vacuum suction.

13. The device of claim 1, additionally comprising a source of vacuum suction in fluid communication with said outer suction foot portion, said source of vacuum suction selected from the group consisting of a hand pump, or a syringe attached to said elongated sheath body, or a motorized pump supplying vacuum suction.

14. The device of claim 1, additionally comprising a removable spacer adapted to maintain the position of said inner suction foot portion with respect to said outer suction foot portion.

15. The device of claim 1, said distal end portion of said elongated sheath body additionally comprises a moveable cover.

16. The device of claim 1, wherein said elongated sheath body comprises a closure lid adapted to reversibly open and close said distal lead outlet.

17. A device adapted for the thoracoscopic placement of a lead at a target site on an epicardial surface of a heart, the device comprising:
(a) an inner tubular lead conduit having a flexible inner lead conduit distal end comprising an inner suction foot portion, said inner tubular lead conduit adapted to conduct a vacuum to said inner suction foot portion;
(b) an outer tubular lead conduit having a flexible outer lead conduit distal end comprising an outer suction foot portion, said outer tubular lead conduit adapted to conduct a vacuum to said outer suction foot portion while being adapted to slidingly conduct said inner tubular lead conduit, so as to permit said inner tubular lead conduit to be extended from said outer lead conduit distal end;
(c) a locking mechanism adapted to restrict the axial movement of said inner tubular lead conduit with respect to said outer tubular lead conduit;
(d) an elongated sheath body having a longitudinal axis, a proximal end portion and a distal end portion, and having a proximal inlet and a distal lead outlet for extending said inner and outer lead conduits therethrough, said elongated sheath body comprising a lead receiving passageway for receiving and conducting said inner and outer lead conduits between said proximal inlet and said distal lead outlet;
(e) a first actuator adapted to articulate said inner suction foot portion and said outer suction foot portion while said inner suction foot portion is disposed within said outer suction foot portion; and
(f) a second actuator adapted to articulate said inner suction foot portion when said inner suction foot portion is extended from said outer suction foot portion.

18. The device of claim 17, additionally comprising a lead drive head having a flexible distal end and inserted within said inner tubular lead conduit so as to extend to said inner tubular lead conduit distal end, said flexible distal end bearing a lead extending through said lead drive head and having a lead distal end portion, said lead distal end portion extending from said distal end of said inner lead conduit for contact with the epicardial surface of the heart.

19. The device of claim 17, wherein said inner tubular lead conduit is longer than said outer tubular lead conduit, and additionally comprising a spacer adapted to maintain inner suction foot portion within said outer suction foot portion.

20. The device of claim 17 additionally comprising an electrocautery blade extending from between said inner and outer suction foot portions.

21. The device of claim 20 wherein electrocautery blade is adapted to be rotated 360 degrees and is energized by a spring biased switch in an extended position.

22. A device adapted for the thoracoscopic placement of a lead at a target site on an epicardial surface of a heart or other organ, the device comprising:
(a) an inner tubular lead conduit having a flexible inner lead conduit distal end comprising an inner suction foot portion, said inner tubular lead conduit adapted to conduct a vacuum to said inner suction foot portion;
(b) an outer tubular lead conduit having a flexible outer lead conduit distal end comprising an outer suction foot portion, said outer tubular lead conduit adapted to conduct a vacuum to said outer suction foot portion while being adapted to slidingly conduct said inner tubular lead conduit, so as to permit said inner tubular lead conduit to be extended from said outer lead conduit distal end and so as to be moveable from a first position wherein said inner suction foot portion is substantially coplanar with said outer suction foot portion to a second position wherein said inner suction foot portion extends beyond the plane of said outer suction foot portion;
(c) a handle adapted to support said inner tubular lead conduit;
(d) a first actuator adapted to articulate said inner suction foot portion and said outer suction foot portion while said inner suction foot portion is disposed within said outer suction foot portion; and
(e) a second actuator adapted to articulate said inner suction foot portion when said inner suction foot portion is extended from said outer suction foot portion.

23. The device of claim 22, additionally comprising a lead drive head having a flexible distal end and inserted within said inner tubular lead conduit so as to extend to said inner tubular lead conduit distal end, said flexible distal end bearing a lead or probe or other attachment extending through said lead drive head and having a lead distal end portion, said lead distal end portion extending from said distal end of said lead drive head for contact with the epicardial surface of the heart or other organ.

24. The device of claim 22 additionally comprising an electrocautery blade extending from between said inner and outer suction foot portions.

25. A device adapted for the thoracoscopic placement of a lead at a target site on an epicardial surface of a heart, the device comprising:
   (a) an inner tubular lead conduit having a flexible inner lead conduit distal end comprising an inner suction foot portion, said inner tubular lead conduit having a lead aperture, and being adapted to conduct a vacuum to said inner suction foot portion;
   (b) an outer tubular lead conduit having a flexible outer lead conduit distal end comprising an outer suction foot portion, said outer tubular lead conduit adapted to conduct a vacuum to said outer suction foot portion while being adapted to slidingly conduct said inner tubular lead conduit, so as to permit said inner tubular lead conduit to be extended from said outer lead conduit distal end; and
   (c) a lead extending through said inner tubular lead conduit into said lead aperture and adapted to be moved from a position within said lead aperture to a position beyond said inner lead conduit distal end.

26. The device of claim 25 additionally comprising a first actuator adapted to articulate said inner suction foot portion and said outer suction foot portion while said inner suction foot portion is disposed within said outer suction foot portion; and a second actuator adapted to articulate said inner suction foot portion when said inner suction foot portion is extended from said outer suction foot portion.

\* \* \* \* \*